US012145976B2

(12) United States Patent
Kim et al.

(10) Patent No.: US 12,145,976 B2
(45) Date of Patent: Nov. 19, 2024

(54) MODIFIED A1-A2 DOMAINS OF NON-NATURAL NKG2D LIGANDS THAT BIND NON-NATURAL NKG2D RECEPTORS

(71) Applicant: XYPHOS BIOSCIENCES INC., South San Francisco, CA (US)

(72) Inventors: Kaman C. Kim, San Bruno, CA (US); Kyle E. Landgraf, Alameda, CA (US)

(73) Assignee: XYPHOS BIOSCIENCES INC., South San Francisco, CA (US)

( * ) Notice: Subject to any disclaimer, the term of this patent is extended or adjusted under 35 U.S.C. 154(b) by 850 days.

(21) Appl. No.: 16/366,320

(22) Filed: Mar. 27, 2019

(65) Prior Publication Data

US 2019/0300594 A1    Oct. 3, 2019

Related U.S. Application Data

(60) Provisional application No. 62/648,636, filed on Mar. 27, 2018.

(51) Int. Cl.
| C07K 14/74 | (2006.01) |
| A61K 35/17 | (2015.01) |
| A61P 35/00 | (2006.01) |
| C07K 14/705 | (2006.01) |
| C07K 16/28 | (2006.01) |
| C07K 16/46 | (2006.01) |
| C07K 19/00 | (2006.01) |

(52) U.S. Cl.
CPC .......... *C07K 14/7056* (2013.01); *A61K 35/17* (2013.01); *A61P 35/00* (2018.01); *C07K 14/70539* (2013.01); *C07K 16/2833* (2013.01); *C07K 16/2851* (2013.01)

(58) Field of Classification Search
None
See application file for complete search history.

(56) References Cited

U.S. PATENT DOCUMENTS

| 10,259,858 B2* | 4/2019 | Landgraf | C07K 16/28 |
| 11,440,948 B2* | 9/2022 | Kim | A61K 39/001102 |
| 2003/0036159 A1 | 2/2003 | Baker et al. | |
| 2016/0159882 A1 | 6/2016 | Landgraf et al. | |

FOREIGN PATENT DOCUMENTS

| WO | WO-1999/031241 A1 | 6/1999 |
| WO | 2017/024131 A1 | 2/2017 |
| WO | WO-2019/028027 A1 | 2/2019 |
| WO | WO-2020/033587 A1 | 2/2020 |

OTHER PUBLICATIONS

Wittenbrink et al (Eur. J. Immunol. 2009, 39: 1642-1651) (Year: 2009).*
Dictionary.com (2021, pp. 1-6) (Year: 2021).*
Emboss needle alignments for 11440948, 2023, 3 pages (Year: 2023).*
Emboss needle alignments for 10258858, 2023, 3 pages (Year: 2023) (Year: 2023).*
Communication, dated Oct. 8, 2020, issued by the International Bureau in International Application No. PCT/US2019/024298.
Belting et al., "Critical role of the NKG2D Receptor for NK cell mediated control and immune escape of B-cell lymphoma", Eur. J. Immunol., vol. 45, p. 2593-2601 (2015).
Communication dated Jul. 3, 2019, issued by European Patent Office in International Application No. PCT/US2019/024298, 6 pages.
Lengyel et al., "Mutations Designed to Destabilize the Receptor-Bound Conformation Increase MICA-NKG2D Association Rate and Affinity", Journal of Biological Chemistry, vol. 282, No. 42, Oct. 19, 2007 (Oct. 19, 2007), pp. 30658-30666.
Culpepper et al., "Systematic mutation and thermodynamic analysis of central tyrosine pairs in polyspecific NKG2D receptor interactions", Molecular Immunology, Pergamon, GB, vol. 48, No. 4, Jan. 1, 2011 (Jan. 1, 2011), pp. 516-523.
Zingoni et al., "NKG2D and Its Ligands: "One for All, All for One"", Frontiers in Immunology, vol. 9, Mar. 12, 2018 (Mar. 12, 2018), entire document pp. 1-12.

* cited by examiner

Primary Examiner — Michael Szperka
Assistant Examiner — Marianne DiBrino
(74) Attorney, Agent, or Firm — MARSHALL, GERSTEIN & BORUN LLP

(57) ABSTRACT

This present disclosure relates generally to the production of polypeptides comprised of modified α1-α2 domains of NKG2D ligands which bind specifically to a non-natural ectodomain of a non-natural NKG2D receptor and wherein heterologous molecules are attached to the modified α1-α2 domains of NKG2D ligands. The present disclosure further relates to modified α1-α2 domains of NKG2D ligands attached to heterologous molecules including polypeptides, and in some embodiments, antibodies or fragments of antibodies. The present disclosure also relates to modified forms of the NKG2D receptor engineered to provide a combination of enhanced and diminished binding to non-natural and natural versions of NKG2D ligands, respectively.

10 Claims, 19 Drawing Sheets

Specification includes a Sequence Listing.

Figure 1A

```
NKG2D.wt    FLNSLFNQEVQIPLTESYCGPCPKNWICYKNNCYQFFDESKNWYESQASCMSQNASLLKV
NKG2D.YA    FLNSLFNQEVQIPLTESYCGPCPKNWICYKNNCYQFFDESKNWYESQASCMSQNASLLKV
NKG2D.AF    FLNSLFNQEVQIPLTESYCGPCPKNWICYKNNCYQFFDESKNWYESQASCMSQNASLLKV

Y152
                              |
NKG2D.wt    YSKEDQDLLKLVKSYHWMGLVHIPTNGSWQWEDGSILSPNLLTIIEMQKGDCALYASSFK
NKG2D.YA    YSKEDQDLLKLVKSAHWMGLVHIPTNGSWQWEDGSILSPNLLTIIEMQKGDCALYASSFK
NKG2D.AF    YSKEDQDLLKLVKSAHWMGLVHIPTNGSWQWEDGSILSPNLLTIIEMQKGDCALYASSFK

Y199
             |
NKG2D.wt    GYIENCSTPNTYICMQRTV
NKG2D.YA    GYIENCSTPNTYICMQRTV
NKG2D.AF    GFIENCSTPNTYICMQRTV
```

Figure 1B

```
ULBP2α1α2   DPHSLCYDITVIPKFRPGPRWCAVQGQVDEKTFLHYDCGNKTVTPVSPLGKKLNVTTAWK
ULBP2.R80W  EPHSLSYDITVIPKFRPGPRWCAVQGQVDEKTFLHYDCGNKTVTPVSPLGKKLNVTTAWK
ULBP2.S3    EPHSLSYDITVIPKFRPGPRWCAVQGQVDEKTFLHYDCGNKTVTPVSPLGKKLNVTTAWK
ULBP2.C     EPHSLSYDITVIPKFRPGPRWCAVQGQVDEKTFLHYDCGNKTVTPVSPLGKKLNVTTAWK
ULBP2.R     EPHSLSYDITVIPKFRPGPRWCAVQGQVDEKTFLHYDCGNKTVTPVSPLGKKLNVTTAWK
ULBP2.AA    EPHSLSYDITVIPKFRPGPRWCAVQGQVDEKTFLHYDCGNKTVTPVSPLGKKLNVTTAWK
ULBP2.AB    EPHSLSYDITVIPKFRPGPRWCAVQGQVDEKTFLHYDCGNKTVTPVSPLGKKLNVTTAWK

R80
                               |
ULBP2α1α2   AQNPVLREVVDILTEQLRDIQLENYTPKEPLTLQARMSCEQKAEGHSSGSWQFSFDGQIF
ULBP2.R80W  AQNPVLREVVDILTEQLWDIQLENYTPKEPLTLQARMSCEQKAEGHSSGSWQFSFDGQIF
ULBP2.S3    AQNPVLREVVDILTEQLWDIQLENYTPKEPLTLQARMSCEQKAEGHSSGSWQFSFDGQIF
ULBP2.C     AQNPVLREVVDILTEQLWDIQLENYTPKEPLTLQARMSCEQKAEGHSSGSWQFSFDGQIF
ULBP2.R     AQNPVLREVVDILTEQLWDIQLENYTPKEPLTLQARMSCEQKAEGHSSGSWQFSFDGQIF
ULBP2.AA    AQNPVLREVVDILTEQLWDIQLENYTPKEPLTLQARMSCEQKAEGHSSGSWQFSFDGQIF
ULBP2.AB    AQNPVLREVVDILTEQLWDIQLENYTPKEPLTLQARMSCEQKAEGHSSGSWQFSFDGQIF

M154
                                    |
ULBP2α1α2   LLFDSEKRMWTTVHPGARKMKEKWENDKVVAMSFHYFSMGDCIGWLEDFLMGMDSTLEPS
ULBP2.R80W  LLFDSEKRMWTTVHPGARKMKEKWENDKVVAMSFHYFSMGDCIGWLEDFLMGMDSTLEPS
ULBP2.S3    LLFDSEKRMWTTVHPGARKMKEKWENDKVVA      SMGDCIGWLEDFLMGMDSTLEPS
ULBP2.C     LLFDSEKRMWTTVHPGARKMKEKWENDKVVA      SMGDCIGWLEDFLMGMDSTLEPS
ULBP2.R     LLFDSEKRMWTTVHPGARKMKEKWENDKVVA      SMGDCIGWLEDFLMGMDSTLEPS
ULBP2.AA    LLFDSEKRMWTTVHPGARKMKEKWENDKVVA      SMGDCIGWLEDFLMGMDSTLEPS
ULBP2.AB    LLFDSEKRMWTTVHPGARKMKEKWENDKVVA      SMGDCIGWLEDFLMGMDSTLEPS
```

Figure 2

| eNKG2D variant | SEQ ID NO (ectodomain) | SEQ ID NO (Fc-fusion) | Y152 substitution | Y199 substitution | Protein aggregation (Akta SEC) |
|---|---|---|---|---|---|
| wild-type | 17 | 40 | | | Low |
| Y152A | 18 | 41 | A | | Low |
| Y199A | 19 | 42 | | A | High |
| Y152A/Y199A | 20 | 43 | A | A | High |
| 1 | 21 | 44 | | F | Low |
| 2 | 22 | 45 | S | | Low |
| 3 | 23 | 46 | T | | Low |
| 4 | 24 | 47 | V | | Low |
| 5 | 25 | 48 | A | F | Low |
| 6 | 26 | 49 | L | F | Intermediate |
| 7 | 27 | 50 | S | F | Low |
| 8 | 28 | 51 | T | F | Low |
| 9 | 29 | 52 | V | F | Intermediate |
| 10 | 30 | 53 | | D | High |
| 11 | 31 | 54 | | E | High |
| 12 | 32 | 55 | D | D | High |
| 13 | 33 | 56 | E | E | High |
| 14 | 34 | 57 | L | | High |
| 15 | 35 | 58 | F | F | Low |

Figure 5

| eNKG2D variant | Y152 substitution | Y199 substitution | MICwed MicAbody binding | MIC2S MicAbody binding |
|---|---|---|---|---|
| wild-type | | | 100 | 100 |
| Y152A | A | | 50 | 100 |
| Y199A | | A | nt | nt |
| Y152A/Y199A | A | A | nt | nt |
| 1 | | F | 100 | 100 |
| 2 | S | | 50 | 100 |
| 3 | T | | 50 | 100 |
| 4 | V | | 50 | 100 |
| 5 | A | F | 0 | 50 |
| 6 | L | F | nt | nt |
| 7 | S | F | 0 | 50 |
| 8 | T | F | 0 | 50 |
| 9 | V | F | 0 | 50 |
| 10 | | D | nt | nt |
| 11 | | E | nt | nt |
| 12 | D | D | nt | nt |
| 13 | E | E | nt | nt |
| 14 | L | | nt | nt |
| 15 | F | F | nt | nt |

Figure 7

|  | Fc-eNKG2D | MicAbody | | |
|---|---|---|---|---|
|  |  | ULBP2.wt | MICwed | MIC25 |
| wt | NKG2D.wt Y\|Y | 1.41 | 0.0067 | ~0.0039 |
| Y152 | eNKG2D A\|Y | 27.86 | 4.30 | 0.0057 |
| Y152 | eNKG2D2 S\|Y | 34.78 | 4.16 | 0.0056 |
| Y152 | eNKG2D3 T\|Y | 31.14 | 4.33 | 0.0056 |
| Y152 | eNKG2D4 V\|Y | 35.78 | 4.84 | ~0.0043 |
| Y152 | eNKG2D14 L\|Y | 87.63 | 9.39 | 0.010 |
| Y199 | eNKG2D1 Y\|F | 23.08 | 0.32 | 0.0048 |
| Y199 | eNKG2D10 Y\|D | nt | nt | nt |
| Y199 | eNKG2D11 Y\|E | nt | nt | nt |
| Y152\|Y199 | eNKG2D5 A\|F | nb | 280.5 | 0.79 |
| Y152\|Y199 | eNKG2D6 L\|F | nb | nb | 0.37 |
| Y152\|Y199 | eNKG2D7 S\|F | nb | 347.3 | 20.94 |
| Y152\|Y199 | eNKG2D8 T\|F | nb | 570.6 | 4.51 |
| Y152\|Y199 | eNKG2D9 V\|F | nb | 90.0 | 0.43 |
| Y152\|Y199 | eNKG2D15 F\|F | 57.05 | 31.3 | 0.046 |
| Y152\|Y199 | eNKG2D12 D\|D | nb | nb | nb |
| Y152\|Y199 | eNKG2D13 E\|E | nb | nb | nb |

Figure 8
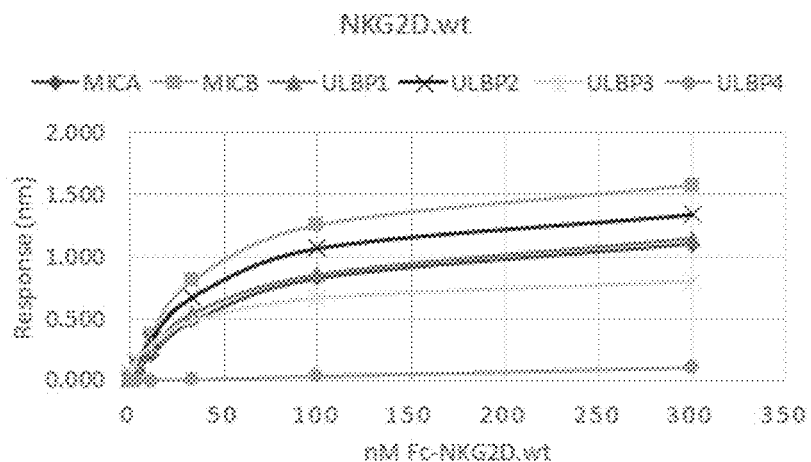
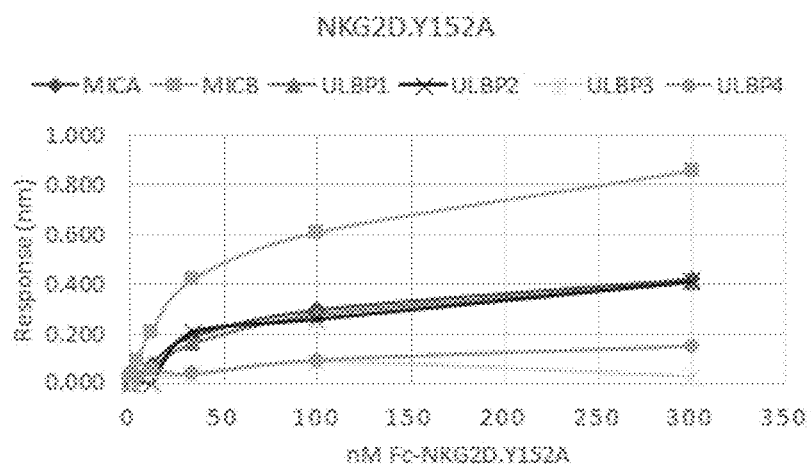
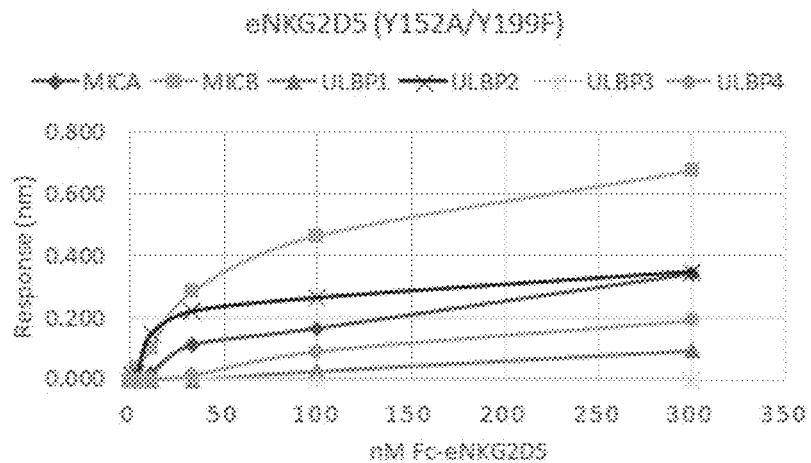

Figure 9

| Phage clone frequency (of the subset examined by spot ELISA) | ULBP2 residue | | | | | | | |
|---|---|---|---|---|---|---|---|---|
| | 8 | 80 | 154 | 155 | 156 | 157 | 158 | 159 |
| | C | R | M | S | F | H | Y | F |
| 83 | S | W | T | T | F | W | Q | I |
| 9 | S | W | T | M | L | R | Q | W |
| 8 | S | W | T | L | L | W | G | W |
| 4 | S | W | T | I | L | W | Q | T |
| 4 | S | W | T | M | L | R | Q | F |
| 3 | S | W | T | L | L | W | Q | A |
| 3 | S | W | T | L | L | W | H | W |
| 2 | S | W | T | L | L | W | Q | W |
| 2 | S | W | T | M | F | W | S | W |
| 2 | S | W | T | M | L | W | K | W |
| 2 | S | W | T | S | L | W | S | W |
| 2 | S | W | T | T | L | W | Q | V |
| 2 | S | W | T | V | L | W | Q | A |
| 2 | S | W | T | V | L | W | S | A |
| 1 | S | W | T | E | L | W | R | T |
| 1 | S | W | T | G | L | W | H | A |
| 1 | S | W | T | H | L | W | G | W |
| 1 | S | W | T | H | L | W | K | F |
| 1 | S | W | T | I | L | W | H | T |
| 1 | S | W | T | L | F | S | W | Y |
| 1 | S | W | T | L | L | P | A | W |
| 1 | S | W | T | L | L | R | Q | F |
| 1 | S | W | T | L | L | W | A | A |
| 1 | S | W | T | L | L | W | H | A |
| 1 | S | W | T | L | M | S | W | W |
| 1 | S | W | T | L | M | W | Q | W |
| 1 | S | W | T | M | F | R | Q | W |
| 1 | S | W | T | M | F | R | Q | Y |
| 1 | S | W | T | M | F | W | Q | W |
| 1 | S | W | T | M | I | Y | S | W |
| 1 | S | W | T | M | L | A | H | W |

| Phage clone frequency (of the subset examined by spot ELISA) | ULBP2 residue | | | | | | | |
|---|---|---|---|---|---|---|---|---|
| | 8 | 80 | 154 | 155 | 156 | 157 | 158 | 159 |
| | C | R | M | S | F | H | Y | F |
| 1 | S | W | T | M | L | F | Q | W |
| 1 | S | W | T | M | L | K | Q | W |
| 1 | S | W | T | M | L | M | Q | W |
| 1 | S | W | T | M | L | P | Y | W |
| 1 | S | W | T | M | L | R | Q | S |
| 1 | S | W | T | M | L | R | Q | Y |
| 1 | S | W | T | M | L | T | Q | W |
| 1 | S | W | T | M | L | W | H | A |
| 1 | S | W | T | M | L | W | N | W |
| 1 | S | W | T | M | L | W | S | A |
| 1 | S | W | T | M | L | W | W | S |
| 1 | S | W | T | M | M | R | Q | W |
| 1 | S | W | T | N | I | W | Q | V |
| 1 | S | W | T | N | L | W | N | V |
| 1 | S | W | T | N | L | W | Q | S |
| 1 | S | W | T | N | L | W | S | A |
| 1 | S | W | T | N | L | W | S | Y |
| 1 | S | W | T | N | M | W | G | W |
| 1 | S | W | T | S | L | C | W | Y |
| 1 | S | W | T | S | L | W | G | A |
| 1 | S | W | T | S | L | W | G | I |
| 1 | S | W | T | S | L | W | Q | S |
| 1 | S | W | T | S | L | W | Q | Y |
| 1 | S | W | T | S | L | W | Q | Y |
| 1 | S | W | T | S | L | W | S | A |
| 1 | S | W | T | T | F | W | G | I |
| 1 | S | W | T | T | F | W | Q | M |
| 1 | S | W | T | T | L | W | P | S |
| 1 | S | W | T | T | L | W | S | S |
| 1 | S | W | T | T | M | W | Q | V |
| 1 | S | W | T | V | L | W | Q | M |

Figure 11

| ULBP2 variant | ULBP2 residue | | | | | | | | ELISA EC50s - Rituximab-MicAbody (light-chain ULBP2 fusion) binding to NKG2D.wt or NKG2D.AF | | | |
|---|---|---|---|---|---|---|---|---|---|---|---|---|
| | 8 | 80 | 154 | 155 | 156 | 157 | 158 | 159 | wt EC50 nM | AF EC50 nM | wt/AF EC50 ratio | AF/wt EC50 ratio |
| | C | R | M | S | F | H | Y | F | | | | |
| A | S | W | T | T | F | W | Q | I | 28.95 | 0.061 | 471.12 | 0.00212 |
| B | S | W | T | M | L | R | Q | W | 34.18 | 0.025 | 1373.49 | 0.00073 |
| C | S | W | T | I | L | W | Q | T | 129.83 | 0.029 | 4414.23 | 0.00023 |
| D | S | W | T | L | L | W | Q | A | 10.02 | 0.020 | 489.80 | 0.00204 |
| E | S | W | T | L | L | W | S | W | 51.45 | 0.031 | 1650.77 | 0.00061 |
| F | S | W | T | V | L | W | Q | A | 37.58 | 0.023 | 1639.79 | 0.00061 |
| G | S | W | T | V | L | W | S | A | 40.54 | 0.024 | 1664.58 | 0.00060 |
| I | S | W | T | N | I | W | Q | Y | 1.04 | 0.010 | 99.11 | 0.01009 |
| J | S | W | T | H | L | W | G | W | 5.77 | 0.062 | 93.61 | 0.01068 |
| L | S | W | T | L | F | W | Q | S | 25.33 | 0.053 | 479.31 | 0.00209 |
| O | S | W | T | S | L | W | Q | S | 17.04 | 0.026 | 652.71 | 0.00153 |
| P | S | W | T | M | L | R | Q | F | 2.37 | 0.069 | 34.45 | 0.02903 |
| R | S | W | T | L | L | W | G | W | 104.45 | 0.031 | 3398.27 | 0.00029 |
| T | S | W | T | L | L | W | Q | W | 4.37 | 0.029 | 151.52 | 0.00660 |
| U | S | W | T | M | L | W | K | W | 19.58 | 0.033 | 595.39 | 0.00168 |
| W | S | W | T | M | F | R | Q | W | 27.09 | 0.020 | 1322.15 | 0.00076 |
| Y | S | W | T | S | L | W | S | W | 83.49 | 0.090 | 927.71 | 0.00108 |
| Z | S | W | T | N | L | W | S | A | 98.80 | 0.025 | 3892.50 | 0.00026 |
| AA | S | W | T | M | F | W | S | W | 654.83 | 0.033 | 20092.30 | 0.00005 |
| AB | S | W | T | L | M | W | Q | W | 389.34 | 0.036 | 10801.65 | 0.00009 |
| AD | S | W | T | T | L | W | Q | V | 57.33 | 0.038 | 1504.95 | 0.00066 |

Figure 12

| M154 | S155 | F156 | H157 | Y158 | F159 |
|------|------|------|------|------|------|
| T | M | L | E | L | W |
|   | K | M | T | V | I |
|   | W |   | S | I |   |
|   | L |   | Q | T |   |
|   | T |   | Y |   |   |
|   |   |   | R |   |   |

Figure 14

| | Pos | MHCI HLA supertype representative | | | | | | | | | | | |
|---|---|---|---|---|---|---|---|---|---|---|---|---|---|
| | | A0101 | A0201 | A0301 | A2402 | A2601 | B0702 | B0801 | B1501 | B2705 | B3901 | B4001 | B5801 |
| ULBP2 wild-type | 0 | 48 | 75 | 75 | 23 | 95 | 35 | 49 | 38 | 36 | 55 | 28 | 50 |
| | 1 | 14 | 34 | 46 | 55 | 6.5 | 12 | 5.5 | 3.5 | 39 | 0.7 | | 29 |
| | 2 | 34 | 60 | 95 | 80 | 36 | 47 | 46 | 90 | 60 | 24 | 55 | 75 |
| | 3 | 16 | 44 | 40 | 13 | 11 | 25 | 18 | 6.5 | 32 | 22 | 17 | 48 |
| | 4 | 29 | 70 | 70 | 85 | 8.5 | 48 | 70 | 75 | 29 | 32 | 48 | 65 |
| | 5 | 4 | 21 | 0.6 | 12 | 2.5 | 17 | 46 | | 8.5 | 19 | 18 | |
| | 6 | 27 | 13 | 9.5 | 0.7 | 1.9 | 8 | 6.5 | 0.6 | 24 | 14 | 9 | 0.9 |
| | 7 | 8 | 11 | 21 | 10 | 23 | 19 | 14 | 34 | 29 | 20 | 25 | 8.5 |
| | 8 | 4 | 0.6 | 4.5 | 2.5 | 4 | 6.5 | 0.8 | 0.7 | 9.5 | 3.5 | 6 | 4 |
| | 9 | 5.5 | 21 | 13 | 19 | 9 | 29 | 7 | 6 | 29 | 14 | 15 | 6.5 |
| | 10 | 34 | 55 | 42 | 19 | 22 | 46 | 70 | 55 | 55 | 20 | 20 | 47 |
| | 11 | 12 | 39 | 36 | 40 | 10 | 43 | 70 | 65 | 55 | 3 | 17 | 42 |
| | 12 | 13 | 37 | 42 | | 28 | 24 | 39 | 24 | 16 | 0.6 | 9.5 | 26 |
| | 13 | 15 | 50 | 70 | 14 | 35 | 49 | 24 | 17 | 75 | 24 | 38 | 21 |
| | 14 | 14 | 16 | 30 | 8.5 | 4.5 | 22 | 37 | 8.5 | 31 | 6 | 21 | |
| | 15 | 14 | 0.8 | 18 | 18 | 15 | 12 | 12 | 8 | 13 | 11 | 12 | 28 |
| ULBP2.C | 0 | 48 | 75 | 75 | 23 | 95 | 35 | 49 | 38 | 36 | 55 | 28 | 50 |
| | 1 | 26 | 50 | 70 | 85 | 26 | 36 | 28 | 24 | 39 | 6 | 1.9 | 45 |
| | 2 | 17 | 37 | 65 | 20 | 28 | 29 | 21 | 60 | 34 | 1.9 | 22 | 28 |
| | 3 | 19 | 41 | 50 | 37 | 26 | 24 | 9.5 | 31 | 43 | 10 | 11 | 45 |
| | 4 | 26 | 39 | 60 | 21 | 10 | 32 | 55 | 70 | 29 | 7 | 60 | 7.5 |
| | 5 | 27 | 20 | 8 | 50 | 11 | 17 | 80 | 19 | 16 | 25 | 18 | 5 |
| | 6 | 13 | 4 | 26 | 19 | 20 | 24 | 45 | 55 | 28 | 24 | 21 | 5.5 |
| | 7 | 19 | 34 | 70 | 28 | 41 | 27 | 70 | 55 | 49 | 34 | 36 | 12 |
| | 8 | 7 | 8.5 | 14 | 18 | 0.8 | 4.5 | 30 | 2 | 9.5 | 3 | 11 | 1 |
| | 9 | 39 | 40 | 23 | 29 | 16 | 24 | 30 | 32 | 55 | 15 | 55 | 70 |
| | 10 | 34 | 14 | 17 | 37 | 29 | 28 | 75 | 27 | 40 | 34 | 25 | 34 |
| | 11 | 24 | 73 | 75 | 18 | 33 | 70 | 60 | 44 | 47 | 70 | 27 | 43 |
| | 12 | 6.5 | 19 | 65 | 8.5 | 19 | 25 | 22 | 7 | 5.5 | 0.8 | 2.5 | 20 |
| | 13 | 9.5 | 70 | 65 | 70 | 27 | 42 | 33 | 18 | 70 | 24 | 44 | 11 |
| | 14 | 22 | 35 | 32 | 8.5 | 7 | 21 | 55 | 14 | 31 | 8.5 | 29 | |
| | 15 | 14 | 0.8 | 18 | 18 | 15 | 12 | 12 | 8 | 13 | 11 | 12 | 28 |
| ULBP2.R | 0 | 48 | 75 | 75 | 23 | 95 | 35 | 49 | 38 | 36 | 55 | 28 | 50 |
| | 1 | 26 | 50 | 70 | 85 | 26 | 36 | 28 | 24 | 39 | 6 | 1.9 | 45 |
| | 2 | 14 | 35 | 60 | 28 | 20 | 21 | 12 | 55 | 35 | 0.6 | 14 | 34 |
| | 3 | 15 | 36 | 42 | 29 | 20 | 27 | 13 | 34 | 34 | 15 | 15 | 42 |
| | 4 | 24 | 40 | 60 | 14 | 9 | 30 | 49 | 70 | 27 | 8.5 | 55 | 4 |
| | 5 | 31 | 16 | 12 | 40 | 20 | 23 | 75 | 19 | 20 | 34 | 25 | 5 |
| | 6 | 8 | 17 | 17 | 3 | 8.5 | 23 | 48 | 24 | 20 | 15 | 20 | |
| | 7 | 24 | 37 | 55 | 60 | 20 | 27 | 70 | 65 | 47 | 60 | 34 | 20 |
| | 8 | 8 | 4.5 | 18 | 8.5 | 4 | 5.5 | 19 | 6.5 | 5.5 | 0.7 | 6 | 1.7 |
| | 9 | 10 | 13 | 15 | 18 | 19 | 27 | 37 | 30 | 42 | 14 | 38 | 60 |
| | 10 | 28 | 8.5 | 16 | 31 | 21 | 29 | 70 | 27 | 24 | 17 | 33 | 27 |
| | 11 | 32 | 65 | 65 | 14 | 36 | 65 | 65 | 60 | 55 | 65 | 25 | 46 |
| | 12 | 8 | 26 | 70 | 16 | 46 | 39 | 23 | 31 | 14 | 10 | 17 | 14 |
| | 13 | 47 | 70 | 85 | 28 | 60 | 60 | 55 | 22 | 60 | 55 | 43 | 26 |
| | 14 | 10 | 27 | 38 | 8.5 | 6.5 | 20 | 35 | 8.5 | 20 | 8 | 19 | |
| | 15 | 14 | 0.8 | 18 | 18 | 15 | 12 | 12 | 8 | 13 | 11 | 12 | 28 |

Figure 14 (Cont)

SEQUENCE LISTING

<160> NUMBER OF SEQ ID NOS: 158

<210> SEQ ID NO 1
<211> LENGTH: 183
<212> TYPE: PRT
<213> ORGANISM: Artificial sequence
<220> FEATURE:
<223> OTHER INFORMATION: Synthetic peptide MICA alpha1-alpha2 domain

<400> SEQUENCE: 1

```
Ala Ala Glu Pro His Ser Leu Arg Tyr Asn Leu Thr Val Leu Ser Trp
1               5                   10                  15

Asp Gly Ser Val Gln Ser Gly Phe Leu Thr Glu Val His Leu Asp Gly
            20                  25                  30

Gln Pro Phe Leu Arg Cys Asp Arg Gln Lys Cys Arg Ala Lys Pro Gln
        35                  40                  45

Gly Gln Trp Ala Glu Asp Val Leu Gly Asn Lys Thr Trp Asp Arg Glu
    50                  55                  60
```

Thr Arg Asp Leu Thr Gly Asn Gly Lys Asp Leu Arg Met Thr Leu Ala
65                  70                  75                  80

His Ile Lys Asp Gln Lys Glu Gly Leu His Ser Leu Gln Glu Ile Arg
                85                  90                  95

Val Cys Glu Ile His Glu Asp Asn Ser Thr Arg Ser Ser Gln His Phe
            100                 105                 110

Tyr Tyr Asp Gly Glu Leu Phe Leu Ser Gln Asn Leu Glu Thr Lys Glu
        115                 120                 125

Trp Thr Met Pro Gln Ser Ser Arg Ala Gln Thr Leu Ala Met Asn Val
130                 135                 140

Arg Asn Phe Leu Lys Glu Asp Ala Met Lys Thr Lys Thr His Tyr His
145                 150                 155                 160

Ala Met His Ala Asp Cys Leu Gln Glu Leu Arg Arg Tyr Leu Lys Ser
                165                 170                 175

Gly Val Val Leu Arg Arg Thr
                180

<210> SEQ ID NO 2
<211> LENGTH: 182
<212> TYPE: PRT
<213> ORGANISM: Artificial sequence
<220> FEATURE:
<223> OTHER INFORMATION: Synthetic peptide MICB alpha1-alpha2 domain

<400> SEQUENCE: 2

Ala Glu Pro His Ser Leu Arg Tyr Asn Leu Met Val Leu Ser Gln Asp
1               5                   10                  15

Glu Ser Val Gln Ser Gly Phe Leu Ala Glu Gly His Leu Asp Gly Gln
                20                  25                  30

Pro Phe Leu Arg Tyr Asp Arg Gln Lys Arg Arg Ala Lys Pro Gln Gly
            35                  40                  45

Gln Trp Ala Glu Asp Val Leu Gly Ala Lys Thr Trp Asp Thr Glu Thr
        50                  55                  60

Glu Asp Leu Thr Glu Asn Gly Gln Asp Leu Arg Arg Thr Leu Thr His
65                  70                  75                  80

Ile Lys Asp Gln Lys Gly Gly Leu His Ser Leu Gln Glu Ile Arg Val
                85                  90                  95

Cys Glu Ile His Glu Asp Ser Ser Thr Arg Gly Ser Arg His Phe Tyr
            100                 105                 110

Tyr Asp Gly Glu Leu Phe Leu Ser Gln Asn Leu Glu Thr Gln Glu Ser
        115                 120                 125

Thr Val Pro Gln Ser Ser Arg Ala Gln Thr Leu Ala Met Asn Val Thr
130                 135                 140

Asn Phe Trp Lys Glu Asp Ala Met Lys Thr Lys Thr His Tyr Arg Ala
145                 150                 155                 160

Met Gln Ala Asp Cys Leu Gln Lys Leu Gln Arg Tyr Leu Lys Ser Gly
                165                 170                 175

Val Ala Ile Arg Arg Thr
                180

<210> SEQ ID NO 3
<211> LENGTH: 187
<212> TYPE: PRT
<213> ORGANISM: Artificial sequence
<220> FEATURE:
<223> OTHER INFORMATION: Synthetic peptide ULBP1 alpha1-alpha2 domain

<400> SEQUENCE: 3

```
Ala Ala Glu Pro His Cys Leu Cys Tyr Asp Phe Ile Ile Thr Pro Lys
1               5                   10                  15

Ser Arg Pro Glu Pro Gln Trp Cys Glu Val Gln Gly Leu Val Asp Glu
            20                  25                  30

Arg Pro Phe Leu His Tyr Asp Cys Val Asn His Lys Ala Lys Ala Phe
            35                  40                  45

Ala Ser Leu Gly Lys Lys Val Asn Val Thr Lys Thr Trp Glu Glu Gln
    50                  55                  60

Thr Glu Thr Leu Arg Asp Val Val Asp Phe Leu Lys Gly Gln Leu Leu
65                  70                  75                  80

Asp Ile Gln Val Glu Asn Leu Ile Pro Ile Glu Pro Leu Thr Leu Gln
                85                  90                  95

Ala Arg Met Ser Cys Glu His Glu Ala His Gly His Gly Arg Gly Ser
                100                 105                 110

Trp Gln Phe Leu Phe Asn Gly Gln Lys Phe Leu Leu Phe Asp Ser Asn
            115                 120                 125

Asn Arg Lys Trp Thr Ala Leu His Pro Gly Ala Lys Lys Met Thr Glu
            130                 135                 140

Lys Trp Glu Lys Asn Arg Asp Val Thr Met Phe Phe Gln Lys Ile Ser
145                 150                 155                 160

Leu Gly Asp Cys Lys Met Trp Leu Glu Glu Phe Leu Met Tyr Trp Glu
                165                 170                 175

Gln Met Leu Asp Pro Thr Lys Pro Pro Met Val
                180                 185

<210> SEQ ID NO 4
<211> LENGTH: 189
<212> TYPE: PRT
<213> ORGANISM: Artificial sequence
<220> FEATURE:
<223> OTHER INFORMATION: Synthetic peptide ULBP2 alpha1-alpha2 domain

<400> SEQUENCE: 4

Ala Ala Glu Pro His Ser Leu Cys Tyr Asp Ile Thr Val Ile Pro Lys
1               5                   10                  15

Phe Arg Pro Gly Pro Arg Trp Cys Ala Val Gln Gly Gln Val Asp Glu
            20                  25                  30

Lys Thr Phe Leu His Tyr Asp Cys Gly Asn Lys Thr Val Thr Pro Val
            35                  40                  45

Ser Pro Leu Gly Lys Lys Leu Asn Val Thr Thr Ala Trp Lys Ala Gln
    50                  55                  60

Asn Pro Val Leu Arg Glu Val Val Asp Ile Leu Thr Glu Gln Leu Arg
65                  70                  75                  80

Asp Ile Gln Leu Glu Asn Tyr Thr Pro Lys Glu Pro Leu Thr Leu Gln
                85                  90                  95

Ala Arg Met Ser Cys Glu Gln Lys Ala Glu Gly His Ser Ser Gly Ser
                100                 105                 110

Trp Gln Phe Ser Phe Asp Gly Gln Ile Phe Leu Leu Phe Asp Ser Glu
            115                 120                 125

Lys Arg Met Trp Thr Thr Val His Pro Gly Ala Arg Lys Met Lys Glu
            130                 135                 140

Lys Trp Glu Asn Asp Lys Val Val Ala Met Ser Phe His Tyr Phe Ser
145                 150                 155                 160

Met Gly Asp Cys Ile Gly Trp Leu Glu Asp Phe Leu Met Gly Met Asp
                165                 170                 175
```

Ser Thr Leu Glu Pro Ser Ala Gly Ala Pro Pro Met Val
            180                 185

<210> SEQ ID NO 5
<211> LENGTH: 187
<212> TYPE: PRT
<213> ORGANISM: Artificial sequence
<220> FEATURE:
<223> OTHER INFORMATION: Synthetic peptide ULBP3 alpha1-alpha2 domain

<400> SEQUENCE: 5

Ala Ala Glu Pro His Ser Leu Trp Tyr Asn Phe Thr Ile Ile His Leu
1               5                   10                  15

Pro Arg His Gly Gln Gln Trp Cys Glu Val Gln Ser Gln Val Asp Gln
            20                  25                  30

Lys Asn Phe Leu Ser Tyr Asp Cys Gly Ser Asp Lys Val Leu Ser Met
        35                  40                  45

Gly His Leu Glu Glu Gln Leu Tyr Ala Thr Asp Ala Trp Gly Lys Gln
    50                  55                  60

Leu Glu Met Leu Arg Glu Val Gly Gln Arg Leu Arg Leu Glu Leu Ala
65                  70                  75                  80

Asp Thr Glu Leu Glu Asp Phe Thr Pro Ser Gly Pro Leu Thr Leu Gln
                85                  90                  95

Val Arg Met Ser Cys Glu Cys Glu Ala Asp Gly Tyr Ile Arg Gly Ser
            100                 105                 110

Trp Gln Phe Ser Phe Asp Gly Arg Lys Phe Leu Leu Phe Asp Ser Asn
        115                 120                 125

Asn Arg Lys Trp Thr Val Val His Ala Gly Ala Arg Arg Met Lys Glu
    130                 135                 140

Lys Trp Glu Lys Asp Ser Gly Leu Thr Thr Phe Phe Lys Met Val Ser
145                 150                 155                 160

Met Arg Asp Cys Lys Ser Trp Leu Arg Asp Phe Leu Met His Arg Lys
                165                 170                 175

Lys Arg Leu Glu Pro Thr Ala Pro Pro Met Val
            180                 185

<210> SEQ ID NO 6
<211> LENGTH: 187
<212> TYPE: PRT
<213> ORGANISM: Artificial sequence
<220> FEATURE:
<223> OTHER INFORMATION: Synthetic peptide ULBP4 alpha1-alpha2 domain

<400> SEQUENCE: 6

Ala Ala Glu Pro His Ser Leu Cys Phe Asn Phe Thr Ile Lys Ser Leu
1               5                   10                  15

Ser Arg Pro Gly Gln Pro Trp Cys Glu Ala Gln Val Phe Leu Asn Lys
            20                  25                  30

Asn Leu Phe Leu Gln Tyr Asn Ser Asp Asn Asn Met Val Lys Pro Leu
        35                  40                  45

Gly Leu Leu Gly Lys Lys Val Tyr Ala Thr Ser Thr Trp Gly Glu Leu
    50                  55                  60

Thr Gln Thr Leu Gly Glu Val Gly Arg Asp Leu Arg Met Leu Leu Cys
65                  70                  75                  80

Asp Ile Lys Pro Gln Ile Lys Thr Ser Asp Pro Ser Thr Leu Gln Val
                85                  90                  95

Glu Met Phe Cys Gln Arg Glu Ala Glu Arg Cys Thr Gly Ala Ser Trp

```
                    100                 105                 110

Gln Phe Ala Thr Asn Gly Glu Lys Ser Leu Leu Phe Asp Ala Met Asn
            115                 120                 125

Met Thr Trp Thr Val Ile Asn His Glu Ala Ser Lys Ile Lys Glu Thr
130                 135                 140

Trp Lys Lys Asp Arg Gly Leu Glu Lys Tyr Phe Arg Lys Leu Ser Lys
145                 150                 155                 160

Gly Asp Cys Asp His Trp Leu Arg Glu Phe Leu Gly His Trp Glu Ala
                165                 170                 175

Met Pro Glu Pro Thr Val Ser Pro Pro Met Val
            180                 185

<210> SEQ ID NO 7
<211> LENGTH: 198
<212> TYPE: PRT
<213> ORGANISM: Artificial sequence
<220> FEATURE:
<223> OTHER INFORMATION: Synthetic peptide ULBP5 alpha1-alpha2 domain

<400> SEQUENCE: 7

Gly Leu Ala Asp Pro His Ser Leu Cys Tyr Asp Ile Thr Val Ile Pro
1               5                   10                  15

Lys Phe Arg Pro Gly Pro Arg Trp Cys Ala Val Gln Gly Gln Val Asp
            20                  25                  30

Glu Lys Thr Phe Leu His Tyr Asp Cys Gly Ser Lys Thr Val Thr Pro
        35                  40                  45

Val Ser Pro Leu Gly Lys Lys Leu Asn Val Thr Thr Ala Trp Lys Ala
50                  55                  60

Gln Asn Pro Val Leu Arg Glu Val Val Asp Ile Leu Thr Glu Gln Leu
65                  70                  75                  80

Leu Asp Ile Gln Leu Glu Asn Tyr Ile Pro Lys Glu Pro Leu Thr Leu
                85                  90                  95

Gln Ala Arg Met Ser Cys Glu Gln Lys Ala Glu Gly His Gly Ser Gly
            100                 105                 110

Ser Trp Gln Leu Ser Phe Asp Gly Gln Ile Phe Leu Leu Phe Asp Ser
        115                 120                 125

Glu Asn Arg Met Trp Thr Thr Val His Pro Gly Ala Arg Lys Met Lys
130                 135                 140

Glu Lys Trp Glu Asn Asp Lys Asp Met Thr Met Ser Phe His Tyr Ile
145                 150                 155                 160

Ser Met Gly Asp Cys Thr Gly Trp Leu Glu Asp Phe Leu Met Gly Met
                165                 170                 175

Asp Ser Thr Leu Glu Pro Ser Ala Gly Ala Pro Pro Thr Met Ser Ser
            180                 185                 190

Gly Thr Ala Gln Pro Arg
        195

<210> SEQ ID NO 8
<211> LENGTH: 189
<212> TYPE: PRT
<213> ORGANISM: Artificial sequence
<220> FEATURE:
<223> OTHER INFORMATION: Synthetic peptide ULBP6 alpha1-alpha2 domain

<400> SEQUENCE: 8

Ala Ala Glu Pro His Ser Leu Cys Tyr Asp Ile Thr Val Ile Pro Lys
1               5                   10                  15
```

-continued

```
Phe Arg Pro Gly Pro Arg Trp Cys Ala Val Gln Gly Gln Val Asp Glu
            20                  25                  30

Lys Thr Phe Leu His Tyr Asp Cys Gly Asn Lys Thr Val Thr Pro Val
        35                  40                  45

Ser Pro Leu Gly Lys Lys Leu Asn Val Thr Thr Ala Trp Lys Ala Gln
    50                  55                  60

Asn Pro Val Leu Arg Glu Val Val Asp Ile Leu Thr Glu Gln Leu Leu
65                  70                  75                  80

Asp Ile Gln Leu Glu Asn Tyr Thr Pro Lys Glu Pro Leu Thr Leu Gln
                85                  90                  95

Ala Arg Met Ser Cys Glu Gln Lys Ala Glu Gly His Ser Ser Gly Ser
            100                 105                 110

Trp Gln Phe Ser Ile Asp Gly Gln Thr Phe Leu Leu Phe Asp Ser Glu
        115                 120                 125

Lys Arg Met Trp Thr Thr Val His Pro Gly Ala Arg Lys Met Lys Glu
    130                 135                 140

Lys Trp Glu Asn Asp Lys Asp Val Ala Met Ser Phe His Tyr Ile Ser
145                 150                 155                 160

Met Gly Asp Cys Ile Gly Trp Leu Glu Asp Phe Leu Met Gly Met Asp
                165                 170                 175

Ser Thr Leu Glu Pro Ser Ala Gly Ala Pro Pro Met Val
            180                 185

<210> SEQ ID NO 9
<211> LENGTH: 161
<212> TYPE: PRT
<213> ORGANISM: Artificial sequence
<220> FEATURE:
<223> OTHER INFORMATION: Synthetic peptide OMCP alpha1-alpha2 domain

<400> SEQUENCE: 9

Ala Ala Ala Glu Pro His Lys Leu Ala Phe Asn Phe Asn Leu Glu Ile
1               5                   10                  15

Asn Gly Ser Asp Thr His Ser Thr Val Asp Val Tyr Leu Asp Asp Ser
            20                  25                  30

Gln Ile Ile Thr Phe Asp Gly Lys Asp Ile Arg Pro Thr Ile Pro Phe
        35                  40                  45

Met Ile Gly Asp Glu Ile Phe Leu Pro Phe Tyr Lys Asn Val Phe Ser
    50                  55                  60

Glu Phe Phe Ser Leu Phe Arg Arg Val Pro Thr Ser Thr Pro Tyr Glu
65                  70                  75                  80

Asp Leu Thr Tyr Phe Tyr Glu Cys Asp Tyr Thr Asp Asn Lys Ser Thr
                85                  90                  95

Phe Asp Gln Phe Tyr Leu Tyr Asn Gly Glu Glu Tyr Thr Val Lys Thr
            100                 105                 110

Gln Glu Ala Thr Asn Lys Asn Met Trp Leu Thr Thr Ser Glu Phe Arg
        115                 120                 125

Leu Lys Lys Trp Phe Asp Gly Glu Asp Cys Ile Met His Leu Arg Ser
    130                 135                 140

Leu Val Arg Lys Met Glu Asp Ser Lys Arg Arg Thr Val Pro Pro Met
145                 150                 155                 160

Val

<210> SEQ ID NO 10
<211> LENGTH: 543
<212> TYPE: DNA
```

<213> ORGANISM: Artificial sequence
<220> FEATURE:
<223> OTHER INFORMATION: Synthetic polynucleotide, encoding MICA alpha1-
      alpha2 domain

<400> SEQUENCE: 10

| | | | | | |
|---|---|---|---|---|---|
| gagccccaca | gtcttcgtta | aacctcacg | gtgctgtcct | gggatggatc | tgtgcagtca | 60 |
| gggtttctca | ctgaggtaca | tctggatggt | cagcccttcc | tgcgctgtga | caggcagaaa | 120 |
| tgcagggcaa | agcccaggg | acagtgggca | gaagatgtcc | tgggaaataa | gacatgggac | 180 |
| agagagacca | gagacttgac | agggaacgga | aaggacctca | ggatgaccct | ggctcatatc | 240 |
| aaggaccaga | agaaggctt | gcattccctc | caggagatta | gggtctgtga | gatccatgaa | 300 |
| gacaacagca | ccaggagctc | ccagcatttc | tactacgatg | gggagctctt | cctctcccaa | 360 |
| aacctggaga | ctaaggaatg | gacaatgccc | cagtcctcca | gagctcagac | cttggccatg | 420 |
| aacgtcagga | atttcttgaa | ggaagatgcc | atgaagacca | agacacacta | tcacgctatg | 480 |
| catgcagact | gcctgcagga | actacggcga | tatctaaaat | ccggcgtagt | cctgaggaga | 540 |
| aca | | | | | | 543 |

<210> SEQ ID NO 11
<211> LENGTH: 561
<212> TYPE: DNA
<213> ORGANISM: Artificial sequence
<220> FEATURE:
<223> OTHER INFORMATION: Synthetic polynucleotide, encoding ULBP1
      alpha1-alpha2 domain

<400> SEQUENCE: 11

| | | | | | |
|---|---|---|---|---|---|
| gctgctgagc | cccactgtct | ctgctacgac | tttattataa | ctcctaagtc | aagaccagag | 60 |
| cctcagtggt | gcgaagtaca | aggtttggtt | gacgaaaggc | cttttccttca | ctacgattgt | 120 |
| gtgaaccata | aggcaaaggc | tttcgccagc | ctgggtaaga | aggtaaacgt | tactaagacg | 180 |
| tgggaggagc | agacggaaac | cctccgtgat | gtggttgact | tcttaagggg | tcagctcctc | 240 |
| gatatccaag | tggagaattt | aatccctatc | gaaccgctca | ctctgcaggc | cagaatgtca | 300 |
| tgcgaacatg | aagcacacgg | tcatggaaga | ggtagttggc | aatttttatt | taacggtcaa | 360 |
| aaattcctgc | tgttcgactc | aaacaaccgc | aaatggactg | cgctgcaccc | tggagctaag | 420 |
| aagatgactg | aaaaatggga | gaagaacaga | gacgttacca | tgttcttcca | gaagatttcc | 480 |
| ctgggagatt | gtaagatgtg | gttagaggag | ttcttaatgt | actgggaaca | gatgctggac | 540 |
| cccacaaaac | cccccatggt | g | | | | 561 |

<210> SEQ ID NO 12
<211> LENGTH: 567
<212> TYPE: DNA
<213> ORGANISM: Artificial sequence
<220> FEATURE:
<223> OTHER INFORMATION: Synthetic polynucleotide, encoding ULBP2
      alpha1-alpha2 domain

<400> SEQUENCE: 12

| | | | | | |
|---|---|---|---|---|---|
| gctgctgagc | cccatagtct | gtgttacgac | atcacagtta | ttcccaagtt | caggcccgga | 60 |
| ccgcgctggt | gtgccgtgca | aggacaagtc | gacgaaaaaa | cctttcttca | ttacgattgc | 120 |
| ggaaataaga | ctgtaacgcc | agtctctcct | ttaggtaaga | agttaaacgt | cactacggcg | 180 |
| tggaaggcac | aaaaccccgt | cctgcgcgag | gtcgtcgaca | tcctgactga | acaattgcgc | 240 |
| gacatccagc | tcgagaatta | cactccaaag | gagcctctta | ccctgcaggc | tagaatgtct | 300 |

```
tgcgagcaaa aggcagaggg ccactcctcc ggcagctggc agttcagttt cgacggacaa    360
atctttctgt tattcgattc agagaagaga atgtggacta cagttcaccc cggtgcccgt    420
aaaatgaagg agaagtggga aaacgacaaa gtggtggcga tgtcattcca ctatttctcg    480
atgggagact gcatcggttg gctggaagat ttcctcatgg gtatggactc cactttggag    540
ccatcggctg gtgccccccc catggtg                                        567
```

```
<210> SEQ ID NO 13
<211> LENGTH: 561
<212> TYPE: DNA
<213> ORGANISM: Artificial sequence
<220> FEATURE:
<223> OTHER INFORMATION: Synthetic polynucleotide, encoding ULBP3
      alpha1-alpha2 domain

<400> SEQUENCE: 13
gctgctgagc cccacagctt gtggtacaac ttcaccatta tccacttgcc gagacatggc     60
cagcagtggt gcgaagtgca atcgcaagtc gaccaaaaaa acttcttatc atacgactgc    120
ggcagcgata aggtcttatc tatgggtcat ttggaggaac agctctacgc gaccgacgcc    180
tggggtaaac agctcgagat gctccgtgag gttggacaga ggctgagact ggaactggct    240
gacactgagc tggaagattt cacacctagt ggtccactca cattgcaagt acgcatgagc    300
tgcgagtgtg aggccgatgg atacattagg ggcagctggc agtttagctt cgacggaagg    360
aaattcctgc tcttcgacag taacaatagg aagtggactg ttgtgcatgc tggtgcgcgc    420
agaatgaagg aaaagtggga gaagatagc ggcctgacga ccttcttcaa gatggtgtct    480
atgcgtgact gtaagagctg gctcagagat ttcctcatgc atcgcaagaa gaggttagaa    540
cctaccgctc cccccatggt g                                              561
```

```
<210> SEQ ID NO 14
<211> LENGTH: 561
<212> TYPE: DNA
<213> ORGANISM: Artificial sequence
<220> FEATURE:
<223> OTHER INFORMATION: Synthetic polynucleotide, encoding ULBP4
      alpha1-alpha2 domain

<400> SEQUENCE: 14
gctgctgagc ccactctct ttgcttcaac ttcaccatta aatccctgag caggcctggt      60
cagccgtggt gtgaggcgca ggtctttctt aacaagaatc tcttcctcca atacaactct    120
gataacaaca tggtaaagcc actgggtctc ctgggtaaaa aagtctatgc tacgagcact    180
tggggagaac tcacccagac tcttggcgag gtaggaagag acctgcgcat gctcctctgc    240
gatataaagc cccaaattaa gaccagtgat ccgtccactt tacaagtcga atgttctgc    300 caaagggagg ctgaacgctg caccggagcc tcttggcagt cgcgaccaa tggcgaaaag    360 tccctcttgt tcgatgccat gaatatgacc tggaccgtga tcaatcatga ggcctctaag    420
atcaaggaga cgtggaaaaa ggaccgcggc cttgaaaagt actttaggaa gttgtctaaa    480
ggagactgcg accattggtt acgcgagttc ctcggccatt gggaagcgat gcccgagcca    540
acggttagcc ccccatggt g                                               561
```

```
<210> SEQ ID NO 15
<211> LENGTH: 567
<212> TYPE: DNA
<213> ORGANISM: Artificial sequence
<220> FEATURE:
<223> OTHER INFORMATION: Synthetic polynucleotide, encoding ULBP6
```

-continued alpha1-alpha2 domain

<400> SEQUENCE: 15

```
gctgctgagc cccactcctt atgctatgat atcaccgtga ttccaaagtt ccgaccagga      60
ccccgatggt gcgccgtaca gggacaggtc gacgaaaaga cttttttaca ttacgactgc     120
ggtaacaaga cagtcacacc ggtaagtcct ttgggaaaaa agttaaacgt aaccactgct     180
tggaaggccc agaaccccgt ccttcgagaa gtagtggata ttttgactga acagctgctt     240
gacatccagc tggaaaacta cacacccaaa gagcccctga ctcttcaagc gcgtatgtcg     300
tgtgagcaaa aggccgaagg acacagctcc ggatcctggc agttcagtat cgacggtcag     360
accttcctcc tcttcgattc agaaaagcgc atgtggacta ctgtgcaccc cggcgctcgt     420
aagatgaagg aaaagtggga gaatgataag gacgttgcca tgagttttca ttacattagt     480
atgggagatt gcatcggttg gctggaagac ttcctgatgg gtatggatag tacccttgaa     540
cctagtgccg gagctccccc catggtg                                          567
```

<210> SEQ ID NO 16
<211> LENGTH: 483
<212> TYPE: DNA
<213> ORGANISM: Artificial sequence
<220> FEATURE:
<223> OTHER INFORMATION: Synthetic polynucleotide, encoding OMCP alpha1-alpha2 domain

<400> SEQUENCE: 16

```
gctgctgctg agccccacaa gcttgcgttc aacttcaatc tggaaataaa cggttcagat      60
acccattcaa ccgtggacgt ttatttagac gattcgcaga taatcacctt tgacggcaag     120
gacatccgcc caactatccc gttcatgata ggtgacgaaa tcttccttcc tttttataag     180
aatgtgttct ctgagttctt cagtttgttc cgccgcgtcc ctacctcaac cccctacgaa     240
gacttgactt atttctatga atgcgactac accgacaaca atctacatt cgatcaattc     300
tacctgtaca cggtgaaga gtacaccgtg aagactcaag aggctactaa caagaacatg     360
tggctgacca cttccgagtt cagactgaag aagtggttcg acggcgagga ctgtatcatg     420
caccttagaa gtttagtgag gaaaatggaa gatagcaaga aagaacagt gcccccatg     480
gtg                                                                    483
```

<210> SEQ ID NO 17
<211> LENGTH: 139
<212> TYPE: PRT
<213> ORGANISM: Artificial sequence
<220> FEATURE:
<223> OTHER INFORMATION: Synthetic peptide natural NKG2D ectodomain

<400> SEQUENCE: 17

```
Phe Leu Asn Ser Leu Phe Asn Gln Glu Val Gln Ile Pro Leu Thr Glu
1               5                  10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Tyr His Trp Met Gly Leu
65                  70                  75                  80

Val His Ile Pro Thr Asn Gly Ser Trp Gln Trp Glu Asp Gly Ser Ile
```

```
                    85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Tyr Ile Glu Asn Cys Ser Thr
        115                 120                 125

Pro Asn Thr Tyr Ile Cys Met Gln Arg Thr Val
    130                 135

<210> SEQ ID NO 18
<211> LENGTH: 139
<212> TYPE: PRT
<213> ORGANISM: Artificial sequence
<220> FEATURE:
<223> OTHER INFORMATION: Synthetic peptide non-natural NKG2D Y152A
      ectodomain

<400> SEQUENCE: 18

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Ala His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Tyr Ile Glu Asn Cys Ser Thr
        115                 120                 125

Pro Asn Thr Tyr Ile Cys Met Gln Arg Thr Val
    130                 135

<210> SEQ ID NO 19
<211> LENGTH: 139
<212> TYPE: PRT
<213> ORGANISM: Artificial sequence
<220> FEATURE:
<223> OTHER INFORMATION: Synthetic peptide non-natural NKG2D Y199A
      ectodomain

<400> SEQUENCE: 19

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Tyr His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
```

```
              100                 105                 110

Ala Leu Tyr Ala Ser Ser Phe Lys Gly Ala Ile Glu Asn Cys Ser Thr
            115                 120                 125

Pro Asn Thr Tyr Ile Cys Met Gln Arg Thr Val
        130                 135

<210> SEQ ID NO 20
<211> LENGTH: 139
<212> TYPE: PRT
<213> ORGANISM: Artificial sequence
<220> FEATURE:
<223> OTHER INFORMATION: Synthetic peptide non-natural NKG2D Y152A/Y199A
      ectodomain

<400> SEQUENCE: 20

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Ala His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Ala Ile Glu Asn Cys Ser Thr
        115                 120                 125

Pro Asn Thr Tyr Ile Cys Met Gln Arg Thr Val
    130                 135

<210> SEQ ID NO 21
<211> LENGTH: 139
<212> TYPE: PRT
<213> ORGANISM: Artificial sequence
<220> FEATURE:
<223> OTHER INFORMATION: Synthetic peptide non-natural NKG2D Y199F
      eNKG2D1 ectodomain

<400> SEQUENCE: 21

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Tyr His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Phe Ile Glu Asn Cys Ser Thr
```

```
                115                 120                 125

Pro Asn Thr Tyr Ile Cys Met Gln Arg Thr Val
    130                 135

<210> SEQ ID NO 22
<211> LENGTH: 139
<212> TYPE: PRT
<213> ORGANISM: Artificial sequence
<220> FEATURE:
<223> OTHER INFORMATION: Synthetic peptide non-natural NKG2D Y152S
      eNKG2D2 ectodomain

<400> SEQUENCE: 22

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Tyr Ile Glu Asn Cys Ser Thr
        115                 120                 125

Pro Asn Thr Tyr Ile Cys Met Gln Arg Thr Val
    130                 135

<210> SEQ ID NO 23
<211> LENGTH: 139
<212> TYPE: PRT
<213> ORGANISM: Artificial sequence
<220> FEATURE:
<223> OTHER INFORMATION: Synthetic peptide non-natural NKG2D Y152T
      eNKG2D3 ectodomain

<400> SEQUENCE: 23

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Thr His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Tyr Ile Glu Asn Cys Ser Thr
        115                 120                 125

Pro Asn Thr Tyr Ile Cys Met Gln Arg Thr Val
```

<210> SEQ ID NO 24
<211> LENGTH: 139
<212> TYPE: PRT
<213> ORGANISM: Artificial sequence
<220> FEATURE:
<223> OTHER INFORMATION: Synthetic peptide non-natural NKG2D Y152V eNKG2D4 ectodomain

<400> SEQUENCE: 24

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Val His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Tyr Ile Glu Asn Cys Ser Thr
        115                 120                 125

Pro Asn Thr Tyr Ile Cys Met Gln Arg Thr Val
    130                 135

<210> SEQ ID NO 25
<211> LENGTH: 139
<212> TYPE: PRT
<213> ORGANISM: Artificial sequence
<220> FEATURE:
<223> OTHER INFORMATION: Synthetic peptide non-natural NKG2D Y152A/Y199F eNKG2D5 ectodomain

<400> SEQUENCE: 25

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Ala His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Phe Ile Glu Asn Cys Ser Thr
        115                 120                 125

Pro Asn Thr Tyr Ile Cys Met Gln Arg Thr Val
    130                 135

```
<210> SEQ ID NO 26
<211> LENGTH: 139
<212> TYPE: PRT
<213> ORGANISM: Artificial sequence
<220> FEATURE:
<223> OTHER INFORMATION: Synthetic peptide non-natural NKG2D Y152L/Y199F
      eNKG2D6 ectodomain

<400> SEQUENCE: 26

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Leu His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Phe Ile Glu Asn Cys Ser Thr
        115                 120                 125

Pro Asn Thr Tyr Ile Cys Met Gln Arg Thr Val
    130                 135

<210> SEQ ID NO 27
<211> LENGTH: 139
<212> TYPE: PRT
<213> ORGANISM: Artificial sequence
<220> FEATURE:
<223> OTHER INFORMATION: Synthetic peptide non-natural NKG2D Y152S/Y199F
      eNKG2D7 ectodomain

<400> SEQUENCE: 27

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Ser His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Phe Ile Glu Asn Cys Ser Thr
        115                 120                 125

Pro Asn Thr Tyr Ile Cys Met Gln Arg Thr Val
    130                 135

<210> SEQ ID NO 28
<211> LENGTH: 139
<212> TYPE: PRT
```

-continued

<213> ORGANISM: Artificial sequence
<220> FEATURE:
<223> OTHER INFORMATION: Synthetic peptide non-natural NKG2D Y152T/Y199F
    eNKG2D8 ectodomain

<400> SEQUENCE: 28

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Thr His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Phe Ile Glu Asn Cys Ser Thr
        115                 120                 125

Pro Asn Thr Tyr Ile Cys Met Gln Arg Thr Val
    130                 135

<210> SEQ ID NO 29
<211> LENGTH: 139
<212> TYPE: PRT
<213> ORGANISM: Artificial sequence
<220> FEATURE:
<223> OTHER INFORMATION: Synthetic peptide non-natural NKG2D Y152V/Y199F
    eNKG2D9 ectodomain

<400> SEQUENCE: 29

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Val His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Phe Ile Glu Asn Cys Ser Thr
        115                 120                 125

Pro Asn Thr Tyr Ile Cys Met Gln Arg Thr Val
    130                 135

<210> SEQ ID NO 30
<211> LENGTH: 139
<212> TYPE: PRT
<213> ORGANISM: Artificial sequence
<220> FEATURE:
<223> OTHER INFORMATION: Synthetic peptide non-natural NKG2D Y199D eNKG2D10 ectodomain

<400> SEQUENCE: 30

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Tyr His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Asp Ile Glu Asn Cys Ser Thr
        115                 120                 125

Pro Asn Thr Tyr Ile Cys Met Gln Arg Thr Val
    130                 135

<210> SEQ ID NO 31
<211> LENGTH: 139
<212> TYPE: PRT
<213> ORGANISM: Artificial sequence
<220> FEATURE:
<223> OTHER INFORMATION: Synthetic peptide non-natural NKG2D Y199E
      eNKG2D11 ectodomain

<400> SEQUENCE: 31

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Tyr His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Glu Ile Glu Asn Cys Ser Thr
        115                 120                 125

Pro Asn Thr Tyr Ile Cys Met Gln Arg Thr Val
    130                 135

<210> SEQ ID NO 32
<211> LENGTH: 139
<212> TYPE: PRT
<213> ORGANISM: Artificial sequence
<220> FEATURE:
<223> OTHER INFORMATION: Synthetic peptide non-natural NKG2D Y152D/Y199D
      eNKG2D12 ectodomain

<400> SEQUENCE: 32

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
            35                  40                  45

Ser Cys Met Ser Gln Asn Ala Ser Leu Leu Lys Val Tyr Ser Lys Glu
        50                  55                  60

Asp Gln Asp Leu Leu Lys Leu Val Lys Ser Asp His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Asp Ile Glu Asn Cys Ser Thr
            115                 120                 125

Pro Asn Thr Tyr Ile Cys Met Gln Arg Thr Val
        130                 135

<210> SEQ ID NO 33
<211> LENGTH: 139
<212> TYPE: PRT
<213> ORGANISM: Artificial sequence
<220> FEATURE:
<223> OTHER INFORMATION: Synthetic peptide non-natural NKG2D Y152E/Y199E
      eNKG2D13 ectodomain

<400> SEQUENCE: 33

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
            35                  40                  45

Ser Cys Met Ser Gln Asn Ala Ser Leu Leu Lys Val Tyr Ser Lys Glu
        50                  55                  60

Asp Gln Asp Leu Leu Lys Leu Val Lys Ser Glu His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Glu Ile Glu Asn Cys Ser Thr
            115                 120                 125

Pro Asn Thr Tyr Ile Cys Met Gln Arg Thr Val
        130                 135

<210> SEQ ID NO 34
<211> LENGTH: 139
<212> TYPE: PRT
<213> ORGANISM: Artificial sequence
<220> FEATURE:
<223> OTHER INFORMATION: Synthetic peptide non-natural NKG2D Y152L
      eNKG2D14 ectodomain

<400> SEQUENCE: 34

Phe Leu Asn Ser Leu Phe Asn Gln Glu Val Gln Ile Pro Leu Thr Glu
1               5                   10                  15

```
Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
 50                  55                  60

Asp Gln Asp Leu Leu Lys Leu Val Lys Ser Leu His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
                100                 105                 110

Ala Leu Tyr Ala Ser Ser Phe Lys Gly Tyr Ile Glu Asn Cys Ser Thr
            115                 120                 125

Pro Asn Thr Tyr Ile Cys Met Gln Arg Thr Val
        130                 135

<210> SEQ ID NO 35
<211> LENGTH: 139
<212> TYPE: PRT
<213> ORGANISM: Artificial sequence
<220> FEATURE:
<223> OTHER INFORMATION: Synthetic peptide non-natural NKG2D Y152F/Y199F
      eNKG2D15 ectodomain

<400> SEQUENCE: 35

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
 50                  55                  60

Asp Gln Asp Leu Leu Lys Leu Val Lys Ser Phe His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
                100                 105                 110

Ala Leu Tyr Ala Ser Ser Phe Lys Gly Phe Ile Glu Asn Cys Ser Thr
            115                 120                 125

Pro Asn Thr Tyr Ile Cys Met Gln Arg Thr Val
        130                 135

<210> SEQ ID NO 36
<211> LENGTH: 23
<212> TYPE: PRT
<213> ORGANISM: Artificial sequence
<220> FEATURE:
<223> OTHER INFORMATION: Synthetic peptide MHCI signal sequence

<400> SEQUENCE: 36

Met Gly Leu Gly Pro Val Phe Leu Leu Leu Ala Gly Ile Phe Pro Phe
1               5                   10                  15

Ala Pro Pro Gly Ala Ala Ala
            20
```

<210> SEQ ID NO 37
<211> LENGTH: 69
<212> TYPE: DNA
<213> ORGANISM: Artificial sequence
<220> FEATURE:
<223> OTHER INFORMATION: Synthetic polynucleotide, encoding MHCI signal
      sequence

<400> SEQUENCE: 37
atgggccttg cccagtgtt tctgctgttg gcaggcattt ccctttttgc tccgcccggc        60
gccgcagcc                                                              69

<210> SEQ ID NO 38
<211> LENGTH: 237
<212> TYPE: PRT
<213> ORGANISM: Artificial sequence
<220> FEATURE:
<223> OTHER INFORMATION: Synthetic peptide human IgG1 Fc with IEGR
      linker

<400> SEQUENCE: 38

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg
225                 230                 235

<210> SEQ ID NO 39
<211> LENGTH: 711
<212> TYPE: DNA
<213> ORGANISM: Artificial sequence
<220> FEATURE:
<223> OTHER INFORMATION: Synthetic polynucleotide, encoding human IgG1
      Fc with IEGR linker

<400> SEQUENCE: 39

```
atggacccga aaagctgcga caagactcac acttgtccgc cgtgccccgc ccccgaactg      60
ctgggtggcc cctccgtgtt cctgttcccg cctaagccta aggacaccct tatgatcagc     120
cgcacccctg aagtgacctg tgtcgtcgtg gatgtgtcac acgaggaccc ggaggtcaag     180
ttcaattggt acgtggacgg cgtggaagtg cataacgcaa agaccaagcc tcgggaggaa     240
cagtacaact cgacctaccg cgtggtgtca gtcctgactg tgctgcacca ggactggctg     300
aacgggaagg agtacaagtg caaagtgtcg aacaaggccc tgccggctcc aattgaaaag     360
accatcagca aggccaaggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tggattccga cggaagcttc ttcctgtact ccaagctgac cgtggacaag     600
tcgagatggc agcagggaaa tgtgttcagc tgctccgtga tgcatgaggc gctgcacaac     660
cactacaccc agaagtcact gagcctctcc cccggaaaga tcgaaggacg c              711
```

<210> SEQ ID NO 40
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D fusion

<400> SEQUENCE: 40

```
Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220
```

```
Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
            245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
            275                 280                 285

Ser Gln Asn Ala Ser Leu Leu Lys Val Tyr Ser Lys Glu Asp Gln Asp
            290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
            325                 330                 335

Asn Leu Leu Thr Ile Ile Glu Met Gln Lys Gly Asp Cys Ala Leu Tyr
            340                 345                 350

Ala Ser Ser Phe Lys Gly Tyr Ile Glu Asn Cys Ser Thr Pro Asn Thr
            355                 360                 365

Tyr Ile Cys Met Gln Arg Thr Val
370                 375
```

<210> SEQ ID NO 41
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y152A
      fusion

<400> SEQUENCE: 41

```
Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
            85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
            195                 200                 205
```

```
Phe Ser Cys Ser Val Met His Glu Ala Leu His Asn His Tyr Thr Gln
    210                 215                 220
Lys Ser Leu Ser Leu Ser Pro Gly Lys Ile Glu Gly Arg Phe Leu Asn
225                 230                 235                 240
Ser Leu Phe Asn Gln Glu Val Gln Ile Pro Leu Thr Glu Ser Tyr Cys
                245                 250                 255
Gly Pro Cys Pro Lys Asn Trp Ile Cys Tyr Lys Asn Asn Cys Tyr Gln
            260                 265                 270
Phe Phe Asp Glu Ser Lys Asn Trp Tyr Glu Ser Gln Ala Ser Cys Met
        275                 280                 285
Ser Gln Asn Ala Ser Leu Leu Lys Val Tyr Ser Lys Glu Asp Gln Asp
    290                 295                 300
Leu Leu Lys Leu Val Lys Ser Ala His Trp Met Gly Leu Val His Ile
305                 310                 315                 320
Pro Thr Asn Gly Ser Trp Gln Trp Glu Asp Gly Ser Ile Leu Ser Pro
                325                 330                 335
Asn Leu Leu Thr Ile Ile Glu Met Gln Lys Gly Asp Cys Ala Leu Tyr
            340                 345                 350
Ala Ser Ser Phe Lys Gly Tyr Ile Glu Asn Cys Ser Thr Pro Asn Thr
        355                 360                 365
Tyr Ile Cys Met Gln Arg Thr Val
    370                 375

<210> SEQ ID NO 42
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y199A
      ectodomain

<400> SEQUENCE: 42

Met Asp Pro Lys Ser Cys Asp Lys Thr His Thr Cys Pro Pro Cys Pro
1               5                   10                  15
Ala Pro Glu Leu Leu Gly Gly Pro Ser Val Phe Leu Phe Pro Pro Lys
            20                  25                  30
Pro Lys Asp Thr Leu Met Ile Ser Arg Thr Pro Glu Val Thr Cys Val
        35                  40                  45
Val Val Asp Val Ser His Glu Asp Pro Glu Val Lys Phe Asn Trp Tyr
    50                  55                  60
Val Asp Gly Val Glu Val His Asn Ala Lys Thr Lys Pro Arg Glu Glu
65                  70                  75                  80
Gln Tyr Asn Ser Thr Tyr Arg Val Val Ser Val Leu Thr Val Leu His
                85                  90                  95
Gln Asp Trp Leu Asn Gly Lys Glu Tyr Lys Cys Lys Val Ser Asn Lys
            100                 105                 110
Ala Leu Pro Ala Pro Ile Glu Lys Thr Ile Ser Lys Ala Lys Gly Gln
        115                 120                 125
Pro Arg Glu Pro Gln Val Tyr Thr Leu Pro Pro Ser Arg Asp Glu Leu
    130                 135                 140
Thr Lys Asn Gln Val Ser Leu Thr Cys Leu Val Lys Gly Phe Tyr Pro
145                 150                 155                 160
Ser Asp Ile Ala Val Glu Trp Glu Ser Asn Gly Gln Pro Glu Asn Asn
                165                 170                 175
Tyr Lys Thr Thr Pro Pro Val Leu Asp Ser Asp Gly Ser Phe Phe Leu
```

```
                    180                 185                 190
Tyr Ser Lys Leu Thr Val Asp Lys Ser Arg Trp Gln Gln Gly Asn Val
                195                 200                 205

Phe Ser Cys Ser Val Met His Glu Ala Leu His Asn His Tyr Thr Gln
            210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
                260                 265                 270

Phe Phe Asp Glu Ser Lys Asn Trp Tyr Glu Ser Gln Ala Ser Cys Met
            275                 280                 285

Ser Gln Asn Ala Ser Leu Leu Lys Val Tyr Ser Lys Glu Asp Gln Asp
                290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
                340                 345                 350

Ala Ser Ser Phe Lys Gly Ala Ile Glu Asn Cys Ser Thr Pro Asn Thr
                355                 360                 365

Tyr Ile Cys Met Gln Arg Thr Val
                370                 375

<210> SEQ ID NO 43
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152A/Y199A ectodomain

<400> SEQUENCE: 43

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
        50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160
```

```
Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Ala His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Ala Ile Glu Asn Cys Ser Thr Pro Asn Thr
        355                 360                 365

Tyr Ile Cys Met Gln Arg Thr Val
    370                 375

<210> SEQ ID NO 44
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y199F
      eNKG2D1 fusion

<400> SEQUENCE: 44

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140
```

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys Ile Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
        370                 375

<210> SEQ ID NO 45
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y152S
      eNKG2D2 fusion

<400> SEQUENCE: 45

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln

```
                115                 120                 125
Pro Arg Glu Pro Gln Val Tyr Thr Leu Pro Pro Ser Arg Asp Glu Leu
            130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
    370                 375

<210> SEQ ID NO 46
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y152T
      eNKG2D3 fusion

<400> SEQUENCE: 46

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95
```

```
Gln Asp Trp Leu Asn Gly Lys Glu Tyr Lys Cys Lys Val Ser Asn Lys
                100                 105                 110

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Asp Glu Leu
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
290                 295                 300

Leu Leu Lys Leu Val Lys Ser Thr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Tyr Ile Glu Asn Cys Ser Thr Pro Asn Thr
        355                 360                 365

Tyr Ile Cys Met Gln Arg Thr Val
370                 375

<210> SEQ ID NO 47
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y152V
      eNKG2D4 fusion

<400> SEQUENCE: 47

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80
```

```
Gln Tyr Asn Ser Thr Tyr Arg Val Val Ser Val Leu Thr Val Leu His
                85                  90                  95
Gln Asp Trp Leu Asn Gly Lys Glu Tyr Lys Cys Lys Val Ser Asn Lys
            100                 105                 110
Ala Leu Pro Ala Pro Ile Glu Lys Thr Ile Ser Lys Ala Lys Gly Gln
        115                 120                 125
Pro Arg Glu Pro Gln Val Tyr Thr Leu Pro Pro Ser Arg Asp Glu Leu
    130                 135                 140
Thr Lys Asn Gln Val Ser Leu Thr Cys Leu Val Lys Gly Phe Tyr Pro
145                 150                 155                 160
Ser Asp Ile Ala Val Glu Trp Glu Ser Asn Gly Gln Pro Glu Asn Asn
                165                 170                 175
Tyr Lys Thr Thr Pro Pro Val Leu Asp Ser Asp Gly Ser Phe Phe Leu
            180                 185                 190
Tyr Ser Lys Leu Thr Val Asp Lys Ser Arg Trp Gln Gln Gly Asn Val
        195                 200                 205
Phe Ser Cys Ser Val Met His Glu Ala Leu His Asn His Tyr Thr Gln
    210                 215                 220
Lys Ser Leu Ser Leu Ser Pro Gly Lys Ile Glu Gly Arg Phe Leu Asn
225                 230                 235                 240
Ser Leu Phe Asn Gln Glu Val Gln Ile Pro Leu Thr Glu Ser Tyr Cys
                245                 250                 255
Gly Pro Cys Pro Lys Asn Trp Ile Cys Tyr Lys Asn Asn Cys Tyr Gln
            260                 265                 270
Phe Phe Asp Glu Ser Lys Asn Trp Tyr Glu Ser Gln Ala Ser Cys Met
        275                 280                 285
Ser Gln Asn Ala Ser Leu Leu Lys Val Tyr Ser Lys Glu Asp Gln Asp
    290                 295                 300
Leu Leu Lys Leu Val Lys Ser Val His Trp Met Gly Leu Val His Ile
305                 310                 315                 320
Pro Thr Asn Gly Ser Trp Gln Trp Glu Asp Gly Ser Ile Leu Ser Pro
                325                 330                 335
Asn Leu Leu Thr Ile Ile Glu Met Gln Lys Gly Asp Cys Ala Leu Tyr
            340                 345                 350
Ala Ser Ser Phe Lys Gly Tyr Ile Glu Asn Cys Ser Thr Pro Asn Thr
        355                 360                 365
Tyr Ile Cys Met Gln Arg Thr Val
    370                 375

<210> SEQ ID NO 48
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152A/Y199F eNKG2D5 fusion

<400> SEQUENCE: 48

Met Asp Pro Lys Ser Cys Asp Lys Thr His Thr Cys Pro Pro Cys Pro
1               5                   10                  15
Ala Pro Glu Leu Leu Gly Gly Pro Ser Val Phe Leu Phe Pro Pro Lys
            20                  25                  30
Pro Lys Asp Thr Leu Met Ile Ser Arg Thr Pro Glu Val Thr Cys Val
        35                  40                  45
Val Val Asp Val Ser His Glu Asp Pro Glu Val Lys Phe Asn Trp Tyr
```

```
               50                  55                  60
    Val Asp Gly Val Glu Val His Asn Ala Lys Thr Lys Pro Arg Glu Glu
    65                  70                  75                  80

Gln Tyr Asn Ser Thr Tyr Arg Val Val Ser Val Leu Thr Val Leu His
                    85                  90                  95

Gln Asp Trp Leu Asn Gly Lys Glu Tyr Lys Cys Lys Val Ser Asn Lys
                100                 105                 110

Ala Leu Pro Ala Pro Ile Glu Lys Thr Ile Ser Lys Ala Lys Gly Gln
                115                 120                 125

Pro Arg Glu Pro Gln Val Tyr Thr Leu Pro Pro Ser Arg Asp Glu Leu
            130                 135                 140

Thr Lys Asn Gln Val Ser Leu Thr Cys Leu Val Lys Gly Phe Tyr Pro
    145                 150                 155                 160

Ser Asp Ile Ala Val Glu Trp Glu Ser Asn Gly Gln Pro Glu Asn Asn
                    165                 170                 175

Tyr Lys Thr Thr Pro Pro Val Leu Asp Ser Asp Gly Ser Phe Phe Leu
                180                 185                 190

Tyr Ser Lys Leu Thr Val Asp Lys Ser Arg Trp Gln Gln Gly Asn Val
                195                 200                 205

Phe Ser Cys Ser Val Met His Glu Ala Leu His Asn His Tyr Thr Gln
            210                 215                 220

Lys Ser Leu Ser Leu Ser Pro Gly Lys Ile Glu Gly Arg Phe Leu Asn
    225                 230                 235                 240

Ser Leu Phe Asn Gln Glu Val Gln Ile Pro Leu Thr Glu Ser Tyr Cys
                    245                 250                 255

Gly Pro Cys Pro Lys Asn Trp Ile Cys Tyr Lys Asn Asn Cys Tyr Gln
                260                 265                 270

Phe Phe Asp Glu Ser Lys Asn Trp Tyr Glu Ser Gln Ala Ser Cys Met
                275                 280                 285

Ser Gln Asn Ala Ser Leu Leu Lys Val Tyr Ser Lys Glu Asp Gln Asp
            290                 295                 300

Leu Leu Lys Leu Val Lys Ser Ala His Trp Met Gly Leu Val His Ile
    305                 310                 315                 320

Pro Thr Asn Gly Ser Trp Gln Trp Glu Asp Gly Ser Ile Leu Ser Pro
                    325                 330                 335

Asn Leu Leu Thr Ile Ile Glu Met Gln Lys Gly Asp Cys Ala Leu Tyr
                340                 345                 350

Ala Ser Ser Phe Lys Gly Phe Ile Glu Asn Cys Ser Thr Pro Asn Thr
                355                 360                 365

Tyr Ile Cys Met Gln Arg Thr Val
        370                 375

<210> SEQ ID NO 49
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152L/Y199F eNKG2D6 fusion

<400> SEQUENCE: 49

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30
```

```
Pro Lys Asp Thr Leu Met Ile Ser Arg Thr Pro Glu Val Thr Cys Val
         35                  40                  45
Val Val Asp Val Ser His Glu Asp Pro Glu Val Lys Phe Asn Trp Tyr
 50                  55                  60
Val Asp Gly Val Glu Val His Asn Ala Lys Thr Lys Pro Arg Glu Glu
 65                  70                  75                  80
Gln Tyr Asn Ser Thr Tyr Arg Val Val Ser Val Leu Thr Val Leu His
                 85                  90                  95
Gln Asp Trp Leu Asn Gly Lys Glu Tyr Lys Cys Lys Val Ser Asn Lys
             100                 105                 110
Ala Leu Pro Ala Pro Ile Glu Lys Thr Ile Ser Lys Ala Lys Gly Gln
         115                 120                 125
Pro Arg Glu Pro Gln Val Tyr Thr Leu Pro Pro Ser Arg Asp Glu Leu
     130                 135                 140
Thr Lys Asn Gln Val Ser Leu Thr Cys Leu Val Lys Gly Phe Tyr Pro
145                 150                 155                 160
Ser Asp Ile Ala Val Glu Trp Glu Ser Asn Gly Gln Pro Glu Asn Asn
                 165                 170                 175
Tyr Lys Thr Thr Pro Pro Val Leu Asp Ser Asp Gly Ser Phe Phe Leu
             180                 185                 190
Tyr Ser Lys Leu Thr Val Asp Lys Ser Arg Trp Gln Gln Gly Asn Val
         195                 200                 205
Phe Ser Cys Ser Val Met His Glu Ala Leu His Asn His Tyr Thr Gln
     210                 215                 220
Lys Ser Leu Ser Leu Ser Pro Gly Lys Ile Glu Gly Arg Phe Leu Asn
225                 230                 235                 240
Ser Leu Phe Asn Gln Glu Val Gln Ile Pro Leu Thr Glu Ser Tyr Cys
                 245                 250                 255
Gly Pro Cys Pro Lys Asn Trp Ile Cys Tyr Lys Asn Asn Cys Tyr Gln
             260                 265                 270
Phe Phe Asp Glu Ser Lys Asn Trp Tyr Glu Ser Gln Ala Ser Cys Met
         275                 280                 285
Ser Gln Asn Ala Ser Leu Leu Lys Val Tyr Ser Lys Glu Asp Gln Asp
     290                 295                 300
Leu Leu Lys Leu Val Lys Ser Leu His Trp Met Gly Leu Val His Ile
305                 310                 315                 320
Pro Thr Asn Gly Ser Trp Gln Trp Glu Asp Gly Ser Ile Leu Ser Pro
                 325                 330                 335
Asn Leu Leu Thr Ile Ile Glu Met Gln Lys Gly Asp Cys Ala Leu Tyr
             340                 345                 350
Ala Ser Ser Phe Lys Gly Phe Ile Glu Asn Cys Ser Thr Pro Asn Thr
         355                 360                 365
Tyr Ile Cys Met Gln Arg Thr Val
     370                 375

<210> SEQ ID NO 50
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152S/Y199F eNKG2D7 fusion

<400> SEQUENCE: 50

Met Asp Pro Lys Ser Cys Asp Lys Thr His Thr Cys Pro Pro Cys Pro
1               5                   10                  15
```

```
Ala Pro Glu Leu Leu Gly Gly Pro Ser Val Phe Leu Phe Pro Pro Lys
             20                  25                  30

Pro Lys Asp Thr Leu Met Ile Ser Arg Thr Pro Glu Val Thr Cys Val
         35                  40                  45

Val Val Asp Val Ser His Glu Asp Pro Glu Val Lys Phe Asn Trp Tyr
 50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Lys
             100                 105                 110

Ala Leu Pro Ala Pro Ile Glu Lys Thr Ile Ser Lys Ala Lys Gly Gln
         115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
290                 295                 300

Leu Leu Lys Leu Val Lys Ser His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
    370                 375

<210> SEQ ID NO 51
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152T/Y199F eNKG2D8 fusion
```

```
<400> SEQUENCE: 51

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
290                 295                 300

Leu Leu Lys Leu Val Lys Ser Thr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
    370                 375

<210> SEQ ID NO 52
<211> LENGTH: 376
<212> TYPE: PRT
<213> ORGANISM: Artificial sequence
```

<220> FEATURE:
<223> OTHER INFORMATION: Synthetic peptide human IgG1 Fc-NKG2D
      Y152V/Y199F eNKG2D9 fusion

<400> SEQUENCE: 52

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Val His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
    370                 375

<210> SEQ ID NO 53
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y199D eNKG2D10 fusion

<400> SEQUENCE: 53

```
Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Asp Ile Glu Asn Cys Ser Thr Pro Asn Thr
        355                 360                 365
```

```
Tyr Ile Cys Met Gln Arg Thr Val
        370                 375

<210> SEQ ID NO 54
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y199E
      eNKG2D11 fusion

<400> SEQUENCE: 54

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350
```

Ala Ser Ser Phe Lys Gly Glu Ile Glu Asn Cys Ser Thr Pro Asn Thr
        355                 360                 365

Tyr Ile Cys Met Gln Arg Thr Val
        370                 375

<210> SEQ ID NO 55
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152D/Y199D eNKG2D12 fusion

<400> SEQUENCE: 55

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Asp His Trp Met Gly Leu Val His Ile
305                 310                 315                 320

Pro Thr Asn Gly Ser Trp Gln Trp Glu Asp Gly Ser Ile Leu Ser Pro

```
                    325             330             335
Asn Leu Leu Thr Ile Ile Glu Met Gln Lys Gly Asp Cys Ala Leu Tyr
            340             345             350

Ala Ser Ser Phe Lys Gly Asp Ile Glu Asn Cys Ser Thr Pro Asn Thr
            355             360             365

Tyr Ile Cys Met Gln Arg Thr Val
            370             375

<210> SEQ ID NO 56
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152E/Y199E eNKG2D13 fusion

<400> SEQUENCE: 56

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300
```

Leu Leu Lys Leu Val Lys Ser Glu His Trp Met Gly Leu Val His Ile
305                 310                 315                 320

Pro Thr Asn Gly Ser Trp Gln Trp Glu Asp Gly Ser Ile Leu Ser Pro
            325                 330                 335

Asn Leu Leu Thr Ile Ile Glu Met Gln Lys Gly Asp Cys Ala Leu Tyr
            340                 345                 350

Ala Ser Ser Phe Lys Gly Glu Ile Glu Asn Cys Ser Thr Pro Asn Thr
            355                 360                 365

Tyr Ile Cys Met Gln Arg Thr Val
370                 375

<210> SEQ ID NO 57
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y152L
      eNKG2D14 fusion

<400> SEQUENCE: 57

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Gly Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

```
Ser Gln Asn Ala Ser Leu Leu Lys Val Tyr Ser Lys Glu Asp Gln Asp
            290                 295                 300

Leu Leu Lys Leu Val Lys Ser Leu His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Tyr Ile Glu Asn Cys Ser Thr Pro Asn Thr
        355                 360                 365

Tyr Ile Cys Met Gln Arg Thr Val
370                 375

<210> SEQ ID NO 58
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152F/Y199F eNKG2D15 fusion

<400> SEQUENCE: 58

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
```

```
                260             265             270
Phe Phe Asp Glu Ser Lys Asn Trp Tyr Glu Ser Gln Ala Ser Cys Met
            275                 280                 285

Ser Gln Asn Ala Ser Leu Leu Lys Val Tyr Ser Lys Glu Asp Gln Asp
            290                 295                 300

Leu Leu Lys Leu Val Lys Ser Phe His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
            355                 360                 365

Tyr Ile Cys Met Gln Arg Thr Val
            370                 375

<210> SEQ ID NO 59
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D fusion

<400> SEQUENCE: 59
atggacccga aaagctgcga caagactcac acttgtccgc cgtgccccgc ccccgaactg      60
ctgggtggcc cctccgtgtt cctgttcccg cctaagccta aggacaccct tatgatcagc     120
cgcacccctg aagtgacctg tgtcgtcgtg gatgtgtcac acgaggaccc ggaggtcaag     180
ttcaattggt acgtggacgg cgtggaagtg cataacgcaa agaccaagcc tcgggaggaa     240
cagtacaact cgacctaccg cgtggtgtca gtcctgactg tgctgcacca ggactggctg     300
aacgggaagg agtacaagtg caaagtgtcg aacaaggccc tgccggctcc aattgaaaag     360
accatcagca aggccaaggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tggattccga cggaagcttc ttcctgtact ccaagctgac cgtggacaag     600
tcgagatggc agcagggaaa tgtgttcagc tgctccgtga tgcatgaggc gctgcacaac     660
cactacaccc agaagtcact gagcctctcc cccggaaaga tcgaaggacg cttcttaaac     720
tcattattca accaagaagt tcaaattccc ttgaccgaaa gttactgtgg cccatgtcct     780
aaaaactgga tatgttacaa aaataactgc taccaattt ttgatgagag taaaaactgg     840
tatgagagcc aggcttcttg tatgtctcaa atgccagcc ttctgaaagt atacagcaaa     900
gaggaccagg atttacttaa actggtgaag tcatatcatt ggatgggact agtacacatt     960
ccaacaaatg gatcttggca gtgggaagat ggctccattc tctcacccaa cctactaaca    1020
ataattgaaa tgcagaaggg agactgtgca ctctatgcct cgagctttaa aggctatata    1080
gaaaactgtt caactccaaa tacatacatc tgcatgcaaa ggactgtg                 1128

<210> SEQ ID NO 60
<211> LENGTH: 1128
<212> TYPE: DNA
<213> ORGANISM: Artificial sequence
<220> FEATURE:
<223> OTHER INFORMATION: Synthetic polynucleotide, encoding human IgG1
```

Fc-NKG2D Y152A fusion

<400> SEQUENCE: 60

```
atggacccga aaagctgcga caagactcac acttgtccgc cgtgccccgc ccccgaactg    60
ctgggtggcc cctccgtgtt cctgttcccg cctaagccta aggacaccct tatgatcagc   120
cgcacccctg aagtgacctg tgtcgtcgtg gatgtgtcac acgaggaccc ggaggtcaag   180
ttcaattggt acgtggacgg cgtggaagtg cataacgcaa agaccaagcc tcgggaggaa   240
cagtacaact cgacctaccg cgtggtgtca gtcctgactg tgctgcacca ggactggctg   300
aacgggaagg agtacaagtg caaagtgtcg aacaaggccc tgccggctcc aattgaaaag   360
accatcagca aggccaaggg ccagccaagg gaaccacagg tgtacaccct ccctccttcc   420
cgggacgagc tgaccaaaaa ccaagtgtcc ctgacttgcc ttgtgaaggg gttctaccct   480
tctgacattg ccgtcgaatg ggaatcgaac ggacagcctg aaaacaacta taagactacc   540
ccgcccgtgc tggattccga cggaagcttc ttcctgtact ccaagctgac cgtggacaag   600
tcgagatggc agcagggaaa tgtgttcagc tgctccgtga tgcatgaggc gctgcacaac   660
cactacaccc agaagtcact gagcctctcc cccggaaaga tcgaaggacg cttcttaaac   720
tcattattca accaagaagt tcaaattccc ttgaccgaaa gttactgtgg cccatgtcct   780
aaaaactgga tatgttacaa aaataactgc taccaatttt tgatgagag taaaaactgg   840
tatgagagcc aggcttcttg tatgtctcaa atgccagcc ttctgaaagt atacagcaaa   900
gaggaccagg atttacttaa actggtgaag tcagctcatt ggatgggact agtacacatt   960
ccaacaaatg gatcttggca gtgggaagat ggctccattc tctcacccaa cctactaaca  1020
ataattgaaa tgcagaaggg agactgtgca ctctatgcct cgagctttaa aggctatata  1080
gaaaactgtt caactccaaa tacatacatc tgcatgcaaa ggactgtg               1128
```

<210> SEQ ID NO 61
<211> LENGTH: 1128
<212> TYPE: DNA
<213> ORGANISM: Artificial sequence
<220> FEATURE:
<223> OTHER INFORMATION: Synthetic polynucleotide, encoding human IgG1 Fc-NKG2D Y199A ectodomain

<400> SEQUENCE: 61

```
atggacccga aaagctgcga caagactcac acttgtccgc cgtgccccgc ccccgaactg    60
ctgggtggcc cctccgtgtt cctgttcccg cctaagccta aggacaccct tatgatcagc   120
cgcacccctg aagtgacctg tgtcgtcgtg gatgtgtcac acgaggaccc ggaggtcaag   180
ttcaattggt acgtggacgg cgtggaagtg cataacgcaa agaccaagcc tcgggaggaa   240
cagtacaact cgacctaccg cgtggtgtca gtcctgactg tgctgcacca ggactggctg   300
aacgggaagg agtacaagtg caaagtgtcg aacaaggccc tgccggctcc aattgaaaag   360
accatcagca aggccaaggg ccagccaagg gaaccacagg tgtacaccct ccctccttcc   420
cgggacgagc tgaccaaaaa ccaagtgtcc ctgacttgcc ttgtgaaggg gttctaccct   480
tctgacattg ccgtcgaatg ggaatcgaac ggacagcctg aaaacaacta taagactacc   540
ccgcccgtgc tggattccga cggaagcttc ttcctgtact ccaagctgac cgtggacaag   600
tcgagatggc agcagggaaa tgtgttcagc tgctccgtga tgcatgaggc gctgcacaac   660
cactacaccc agaagtcact gagcctctcc cccggaaaga tcgaaggacg cttcttaaac   720
tcattattca accaagaagt tcaaattccc ttgaccgaaa gttactgtgg cccatgtcct   780
```

```
aaaaactgga tatgttacaa aaataactgc taccaatttt ttgatgagag taaaaactgg      840
tatgagagcc aggcttcttg tatgtctcaa aatgccagcc ttctgaaagt atacagcaaa      900
gaggaccagg atttacttaa actggtgaag tcataccatt ggatgggact agtacacatt      960
ccaacaaatg gatcttggca gtgggaagat ggctccattc tctcacccaa cctactaaca     1020
ataattgaaa tgcagaaggg agactgtgca ctctatgcct cgagctttaa aggcgctata     1080
gaaaactgtt caactccaaa tacatacatc tgcatgcaaa ggactgtg                  1128
```

<210> SEQ ID NO 62
<211> LENGTH: 1128
<212> TYPE: DNA
<213> ORGANISM: Artificial sequence
<220> FEATURE:
<223> OTHER INFORMATION: Synthetic polynucleotide, encoding human IgG1
       Fc-NKG2D Y152A/Y199A ectodomain

<400> SEQUENCE: 62

```
atggacccga aaagctgcga caagactcac acttgtccgc cgtgccccgc ccccgaactg       60
ctgggtggcc cctccgtgtt cctgttcccg cctaagccta aggacaccct tatgatcagc      120
cgcacccctg aagtgacctg tgtcgtcgtg gatgtgtcac acgaggaccc ggaggtcaag      180
ttcaattggt acgtggacgg cgtggaagtg cataacgcaa agaccaagcc tcgggaggaa      240
cagtacaact cgacctaccg cgtggtgtca gtcctgactg tgctcaccca ggactggctg      300
aacgggaagg agtacaagtg caaagtgtcg aacaaggccc tgccggctcc aattgaaaag      360
accatcagca aggccaaggg ccagccaagg gaaccacagg tgtacaccct ccctccttcc      420
cgggacgagc tgaccaaaaa ccaagtgtcc ctgacttgcc ttgtgaaggg gttctaccct      480
tctgacattg ccgtcgaatg ggaatcgaac ggacagcctg aaaacaacta taagactacc      540
ccgcccgtgc tggattccga cggaagcttc ttcctgtact ccaagctgac cgtggacaag      600
tcgagatggc agcagggaaa tgtgttcagc tgctccgtga tgcatgaggc gctgcacaac      660
cactacaccc agaagtcact gagcctctcc cccggaaaga tcgaaggacg cttcttaaac      720
tcattattca accaagaagt tcaaattccc ttgaccgaaa gttactgtgg cccatgtcct      780
aaaaactgga tatgttacaa aaataactgc taccaatttt ttgatgagag taaaaactgg      840
tatgagagcc aggcttcttg tatgtctcaa aatgccagcc ttctgaaagt atacagcaaa      900
gaggaccagg atttacttaa actggtgaag tcagctcatt ggatgggact agtacacatt      960
ccaacaaatg gatcttggca gtgggaagat ggctccattc tctcacccaa cctactaaca     1020
ataattgaaa tgcagaaggg agactgtgca ctctatgcct cgagctttaa aggcgctata     1080
gaaaactgtt caactccaaa tacatacatc tgcatgcaaa ggactgtg                  1128
```

<210> SEQ ID NO 63
<211> LENGTH: 1128
<212> TYPE: DNA
<213> ORGANISM: Artificial sequence
<220> FEATURE:
<223> OTHER INFORMATION: Synthetic polynucleotide, encoding human IgG1
       Fc-NKG2D Y199F eNKG2D1 fusion

<400> SEQUENCE: 63

```
atggacccga aaagctgcga caagactcac acttgtccgc cgtgccccgc ccccgaactg       60
ctgggtggcc cctccgtgtt cctgttcccg cctaagccta aggacaccct tatgatcagc      120
cgcacccctg aagtgacctg tgtcgtcgtg gatgtgtcac acgaggaccc ggaggtcaag      180
ttcaattggt acgtggacgg cgtggaagtg cataacgcaa agaccaagcc tcgggaggaa      240
```

```
cagtacaact cgacctaccg cgtggtgtca gtcctgactg tgctgcacca ggactggctg    300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcataccatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggcttcata   1080
gaaaactgtt caactccaaa tacatacatc tgcatgcaaa ggactgtg              1128

<210> SEQ ID NO 64
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152S eNKG2D2 fusion

<400> SEQUENCE: 64
atggacccga aaagctgcga caagactcac acttgtccgc cgtgccccgc ccccgaactg     60
ctgggtggcc cctccgtgtt cctgttcccg cctaagccta aggacaccct tatgatcagc    120
cgcacccctg aagtgacctg tgtcgtcgtg gatgtgtcac acgaggaccc ggaggtcaag    180
ttcaattggt acgtggacgg cgtggaagtg cataacgcaa agaccaagcc tcggaggaa    240 cagtacaact cgacctaccg cgtggtgtca gtcctgactg tgctgcacca ggactggctg    300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcataccatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggcttcata   1080
gaaaactgtt caactccaaa tacatacatc tgcatgcaaa ggactgtg              1128
```

<210> SEQ ID NO 65
<211> LENGTH: 1128
<212> TYPE: DNA
<213> ORGANISM: Artificial sequence
<220> FEATURE:
<223> OTHER INFORMATION: Synthetic polynucleotide, encoding human IgG1
    Fc-NKG2D Y152T eNKG2D3 fusion

<400> SEQUENCE: 65

```
atggacccga aaagctgcga caagactcac acttgtccgc cgtgccccgc ccccgaactg      60
ctgggtggcc cctccgtgtt cctgttcccg cctaagccta aggacaccct tatgatcagc     120
cgcaccctg aagtgacctg tgtcgtcgtg gatgtgtcac acgaggaccc ggaggtcaag      180
ttcaattggt acgtggacgg cgtggaagtg cataacgcaa agaccaagcc tcggaggaa      240
cagtacaact cgacctaccg cgtggtgtca gtcctgactg tgctgcacca ggactggctg     300
aacgggaagg agtacaagtg caaagtgtcg aacaaggccc tgccggctcc aattgaaaag     360
accatcagca aggccaaggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tggattccga cggaagcttc ttcctgtact ccaagctgac cgtggacaag     600
tcgagatggc agcagggaaa tgtgttcagc tgctccgtga tgcatgaggc gctgcacaac     660
cactacaccc agaagtcact gagcctctcc cccggaaaga tcgaaggacg cttcttaaac     720
tcattattca accaagaagt tcaaattccc ttgaccgaaa gttactgtgg cccatgtcct     780
aaaaactgga tatgttacaa aaataactgc taccaatttt ttgatgagag taaaaactgg     840
tatgagagcc aggcttcttg tatgtctcaa aatgccagcc ttctgaaagt atacagcaaa     900
gaggaccagg atttacttaa actggtgaag tcaactcatt ggatgggact agtacacatt     960
ccaacaaatg gatcttggca gtgggaagat ggctccattc tctcacccaa cctactaaca    1020
ataattgaaa tgcagaaggg agactgtgca ctctatgcct cgagctttaa aggctatata    1080
gaaaactgtt caactccaaa tacatacatc tgcatgcaaa ggactgtg              1128
```

<210> SEQ ID NO 66
<211> LENGTH: 1128
<212> TYPE: DNA
<213> ORGANISM: Artificial sequence
<220> FEATURE:
<223> OTHER INFORMATION: Synthetic polynucleotide, encoding human IgG1
    Fc-NKG2D Y152V eNKG2D4 fusion

<400> SEQUENCE: 66

```
atggacccga aaagctgcga caagactcac acttgtccgc cgtgccccgc ccccgaactg      60
ctgggtggcc cctccgtgtt cctgttcccg cctaagccta aggacaccct tatgatcagc     120
cgcaccctg aagtgacctg tgtcgtcgtg gatgtgtcac acgaggaccc ggaggtcaag      180
ttcaattggt acgtggacgg cgtggaagtg cataacgcaa agaccaagcc tcggaggaa      240
cagtacaact cgacctaccg cgtggtgtca gtcctgactg tgctgcacca ggactggctg     300
aacgggaagg agtacaagtg caaagtgtcg aacaaggccc tgccggctcc aattgaaaag     360
accatcagca aggccaaggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
```

```
ccgcccgtgc tggattccga cggaagcttc ttcctgtact ccaagctgac cgtggacaag      600
tcgagatggc agcagggaaa tgtgttcagc tgctccgtga tgcatgaggc gctgcacaac      660
cactacaccc agaagtcact gagcctctcc cccggaaaga tcgaaggacg cttcttaaac      720
tcattattca accaagaagt tcaaattccc ttgaccgaaa gttactgtgg cccatgtcct      780
aaaaactgga tatgttacaa aaataactgc taccaatttt ttgatgagag taaaaactgg      840
tatgagagcc aggcttcttg tatgtctcaa aatgccagcc ttctgaaagt atacagcaaa      900
gaggaccagg atttacttaa actggtgaag tcagtgcatt ggatgggact agtacacatt      960
ccaacaaatg gatcttggca gtgggaagat ggctccattc tctcacccaa cctactaaca     1020
ataattgaaa tgcagaaggg agactgtgca ctctatgcct cgagctttaa aggctatata     1080
gaaaactgtt caactccaaa tacatacatc tgcatgcaaa ggactgtg                 1128

<210> SEQ ID NO 67
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152A/Y199F eNKG2D5 fusion

<400> SEQUENCE: 67
atggacccga aaagctgcga caagactcac acttgtccgc cgtgcccgc ccccgaactg       60 ctgggtggcc cctccgtgtt cctgttcccg cctaagccta aggacaccct tatgatcagc     120
cgcacccctg aagtgacctg tgtcgtcgtg gatgtgtcac acgaggaccc ggaggtcaag     180
ttcaattggt acgtggacgg cgtggaagtg cataacgcaa agaccaagcc tcgggaggaa     240
cagtacaact cgacctaccg cgtggtgtca gtcctgactg tgctgcacca ggactggctg     300
aacgggaagg agtacaagtg caaagtgtcg aacaaggccc tgccggctcc aattgaaaag     360
accatcagca ggccaagggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tggattccga cggaagcttc ttcctgtact ccaagctgac cgtggacaag     600
tcgagatggc agcagggaaa tgtgttcagc tgctccgtga tgcatgaggc gctgcacaac     660
cactacaccc agaagtcact gagcctctcc cccggaaaga tcgaaggacg cttcttaaac     720
tcattattca accaagaagt tcaaattccc ttgaccgaaa gttactgtgg cccatgtcct     780
aaaaactgga tatgttacaa aaataactgc taccaatttt ttgatgagag taaaaactgg     840
tatgagagcc aggcttcttg tatgtctcaa aatgccagcc ttctgaaagt atacagcaaa     900
gaggaccagg atttacttaa actggtgaag tcagctcatt ggatgggact agtacacatt     960
ccaacaaatg gatcttggca gtgggaagat ggctccattc tctcacccaa cctactaaca    1020
ataattgaaa tgcagaaggg agactgtgca ctctatgcct cgagctttaa aggcttcata    1080
gaaaactgtt caactccaaa tacatacatc tgcatgcaaa ggactgtg                1128

<210> SEQ ID NO 68
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152L/Y199F eNKG2D6 fusion

<400> SEQUENCE: 68
```

```
atggacccga aaagctgcga caagactcac acttgtccgc cgtgccccgc ccccgaactg    60
ctgggtggcc cctccgtgtt cctgttcccg cctaagccta aggacaccct tatgatcagc   120
cgcacccctg aagtgacctg tgtcgtcgtg gatgtgtcac acgaggaccc ggaggtcaag   180
ttcaattggt acgtggacgg cgtggaagtg cataacgcaa agaccaagcc tcgggaggaa   240
cagtacaact cgacctaccg cgtggtgtca gtcctgactg tgctgcacca ggactggctg   300
aacgggaagg agtacaagtg caaagtgtcg aacaaggccc tgccggctcc aattgaaaag   360
accatcagca aggccaaggg ccagccaagg gaaccacagg tgtacaccct ccctccttcc   420
cgggacgagc tgaccaaaaa ccaagtgtcc ctgacttgcc ttgtgaaggg gttctaccct   480
tctgacattg ccgtcgaatg ggaatcgaac ggacagcctg aaaacaacta taagactacc   540
ccgcccgtgc tggattccga cggaagcttc ttcctgtact ccaagctgac cgtggacaag   600
tcgagatggc agcagggaaa tgtgttcagc tgctccgtga tgcatgaggc gctgcacaac   660
cactacaccc agaagtcact gagcctctcc cccggaaaga tcgaaggacg cttcttaaac   720
tcattattca accaagaagt tcaaattccc ttgaccgaaa gttactgtgg cccatgtcct   780
aaaaactgga tatgttacaa aaataactgc taccaatttt ttgatgagag taaaaactgg   840
tatgagagcc aggcttcttg tatgtctcaa aatgccagcc ttctgaaagt atacagcaaa   900
gaggaccagg atttacttaa actggtgaag tcactgcatt ggatgggact agtacacatt   960
ccaacaaatg gatcttggca gtgggaagat ggctccattc tctcacccaa cctactaaca  1020
ataattgaaa tgcagaaggg agactgtgca ctctatgcct cgagctttaa aggcttcata  1080
gaaaactgtt caactccaaa tacatacatc tgcatgcaaa ggactgtg               1128

<210> SEQ ID NO 69
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152S/Y199F eNKG2D7 fusion

<400> SEQUENCE: 69
atggacccga aaagctgcga caagactcac acttgtccgc cgtgccccgc ccccgaactg    60
ctgggtggcc cctccgtgtt cctgttcccg cctaagccta aggacaccct tatgatcagc   120
cgcacccctg aagtgacctg tgtcgtcgtg gatgtgtcac acgaggaccc ggaggtcaag   180
ttcaattggt acgtggacgg cgtggaagtg cataacgcaa agaccaagcc tcgggaggaa   240
cagtacaact cgacctaccg cgtggtgtca gtcctgactg tgctgcacca ggactggctg   300
aacgggaagg agtacaagtg caaagtgtcg aacaaggccc tgccggctcc aattgaaaag   360
accatcagca aggccaaggg ccagccaagg gaaccacagg tgtacaccct ccctccttcc   420
cgggacgagc tgaccaaaaa ccaagtgtcc ctgacttgcc ttgtgaaggg gttctaccct   480
tctgacattg ccgtcgaatg ggaatcgaac ggacagcctg aaaacaacta taagactacc   540
ccgcccgtgc tggattccga cggaagcttc ttcctgtact ccaagctgac cgtggacaag   600
tcgagatggc agcagggaaa tgtgttcagc tgctccgtga tgcatgaggc gctgcacaac   660
cactacaccc agaagtcact gagcctctcc cccggaaaga tcgaaggacg cttcttaaac   720
tcattattca accaagaagt tcaaattccc ttgaccgaaa gttactgtgg cccatgtcct   780
aaaaactgga tatgttacaa aaataactgc taccaatttt ttgatgagag taaaaactgg   840
tatgagagcc aggcttcttg tatgtctcaa aatgccagcc ttctgaaagt atacagcaaa   900
```

```
gaggaccagg atttacttaa actggtgaag tcaagtcatt ggatgggact agtacacatt     960
ccaacaaatg gatcttggca gtgggaagat ggctccattc tctcacccaa cctactaaca    1020
ataattgaaa tgcagaaggg agactgtgca ctctatgcct cgagctttaa aggcttcata    1080
gaaaactgtt caactccaaa tacatacatc tgcatgcaaa ggactgtg                 1128
```

<210> SEQ ID NO 70
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152T/Y199F eNKG2D8 fusion

<400> SEQUENCE: 70

```
atggacccga aaagctgcga caagactcac acttgtccgc cgtgccccgc ccccgaactg      60
ctgggtggcc cctccgtgtt cctgttcccg cctaagccta aggacaccct tatgatcagc     120
cgcacccctg aagtgacctg tgtcgtcgtg gatgtgtcac acgaggaccc ggaggtcaag     180
ttcaattggt acgtggacgg cgtggaagtg cataacgcaa agaccaagcc tcgggaggaa     240
cagtacaact cgacctaccg cgtggtgtca gtcctgactg tgctgcacca ggactggctg     300
aacgggaagg agtacaagtg caaagtgtcg aacaaggccc tgccggctcc aattgaaaag     360
accatcagca aggccaaggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tggattccga cggaagcttc ttcctgtact ccaagctgac cgtggacaag     600
tcgagatggc agcagggaaa tgtgttcagc tgctccgtga tgcatgaggc gctgcacaac     660
cactacaccc agaagtcact gagcctctcc cccggaaaga tcgaaggacg cttcttaaac     720
tcattattca accaagaagt tcaaattccc ttgaccgaaa gttactgtgg cccatgtcct     780
aaaaactgga tatgttacaa aaataactgc taccaatttt ttgatgagag taaaaactgg     840
tatgagagcc aggcttcttg tatgtctcaa aatgccagcc ttctgaaagt atacagcaaa     900
gaggaccagg atttacttaa actggtgaag tcaactcatt ggatgggact agtacacatt     960
ccaacaaatg gatcttggca gtgggaagat ggctccattc tctcacccaa cctactaaca    1020
ataattgaaa tgcagaaggg agactgtgca ctctatgcct cgagctttaa aggcttcata    1080
gaaaactgtt caactccaaa tacatacatc tgcatgcaaa ggactgtg                 1128
```

<210> SEQ ID NO 71
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152V/Y199F eNKG2D9 fusion

<400> SEQUENCE: 71

```
atggacccga aaagctgcga caagactcac acttgtccgc cgtgccccgc ccccgaactg      60
ctgggtggcc cctccgtgtt cctgttcccg cctaagccta aggacaccct tatgatcagc     120
cgcacccctg aagtgacctg tgtcgtcgtg gatgtgtcac acgaggaccc ggaggtcaag     180
ttcaattggt acgtggacgg cgtggaagtg cataacgcaa agaccaagcc tcgggaggaa     240
cagtacaact cgacctaccg cgtggtgtca gtcctgactg tgctgcacca ggactggctg     300
```

```
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcagtgcatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggcttcata   1080
gaaaactgtt caactccaaa tacatacatc tgcatgcaaa ggactgtg               1128
```

<210> SEQ ID NO 72
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y199D eNKG2D10 fusion

<400> SEQUENCE: 72

```
atggaccega aaagctgcga caagactcac acttgtccgc cgtgccccgc ccccgaactg     60
ctgggtggcc cctccgtgtt cctgttcccg cctaagccta aggacaccct tatgatcagc    120 cgcaccccctg aagtgacctg tgtcgtcgtg gatgtgtcac acgaggaccc ggaggtcaag    180
ttcaattggt acgtggacgg cgtggaagtg cataacgcaa agaccaagcc tcgggaggaa    240
cagtacaact cgacctaccg cgtggtgtca gtcctgactg tgctcaccca ggactggctg    300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcatatcatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggcgatata   1080
gaaaactgtt caactccaaa tacatacatc tgcatgcaaa ggactgtg               1128
```

<210> SEQ ID NO 73

<211> LENGTH: 1128
<212> TYPE: DNA
<213> ORGANISM: Artificial sequence
<220> FEATURE:
<223> OTHER INFORMATION: Synthetic polynucleotide, encoding human IgG1 Fc-NKG2D Y199E eNKG2D11 fusion

<400> SEQUENCE: 73

```
atggacccga aaagctgcga caagactcac acttgtccgc cgtgccccgc ccccgaactg      60
ctgggtggcc cctccgtgtt cctgttcccg cctaagccta aggacaccct tatgatcagc     120
cgcaccctg aagtgacctg tgtcgtcgtg gatgtgtcac acgaggaccc ggaggtcaag     180
ttcaattggt acgtggacgg cgtggaagtg cataacgcaa agaccaagcc tcggaggaa     240
cagtacaact cgacctaccg cgtggtgtca gtcctgactg tgctgcacca ggactggctg     300
aacgggaagg agtacaagtg caagtgtcg aacaaggccc tgccggctcc aattgaaaag     360
accatcagca aggccaaggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tggattccga cggaagcttc ttcctgtact ccaagctgac cgtggacaag     600
tcgagatggc agcagggaaa tgtgttcagc tgctccgtga tgcatgaggc gctgcacaac     660
cactacaccc agaagtcact gagcctctcc cccggaaaga tcgaaggacg cttcttaaac     720
tcattattca accaagaagt tcaaattccc ttgaccgaaa gttactgtgg cccatgtcct     780
aaaaactgga tatgttacaa aaataactgc taccaattttt ttgatgagag taaaaactgg     840
tatgagagcc aggcttcttg tatgtctcaa atgccagcc ttctgaaagt atacagcaaa     900
gaggaccagg atttacttaa actggtgaag tcataccatt ggatgggact agtacacatt     960
ccaacaaatg gatcttggca gtgggaagat ggctccattc tctcacccaa cctactaaca    1020
ataattgaaa tgcagaaggg agactgtgca ctctatgcct cgagctttaa aggcgagata    1080
gaaaactgtt caactccaaa tacatacatc tgcatgcaaa ggactgtg               1128
```

<210> SEQ ID NO 74
<211> LENGTH: 1128
<212> TYPE: DNA
<213> ORGANISM: Artificial sequence
<220> FEATURE:
<223> OTHER INFORMATION: Synthetic polynucleotide, encoding human IgG1 Fc-NKG2D Y152D/Y199D eNKG2D12 fusion

<400> SEQUENCE: 74

```
atggacccga aaagctgcga caagactcac acttgtccgc cgtgccccgc ccccgaactg      60
ctgggtggcc cctccgtgtt cctgttcccg cctaagccta aggacaccct tatgatcagc     120
cgcaccctg aagtgacctg tgtcgtcgtg gatgtgtcac acgaggaccc ggaggtcaag     180
ttcaattggt acgtggacgg cgtggaagtg cataacgcaa agaccaagcc tcggaggaa     240
cagtacaact cgacctaccg cgtggtgtca gtcctgactg tgctgcacca ggactggctg     300
aacgggaagg agtacaagtg caagtgtcg aacaaggccc tgccggctcc aattgaaaag     360
accatcagca aggccaaggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tggattccga cggaagcttc ttcctgtact ccaagctgac cgtggacaag     600
tcgagatggc agcagggaaa tgtgttcagc tgctccgtga tgcatgaggc gctgcacaac     660
```

```
cactacaccc agaagtcact gagcctctcc cccggaaaga tcgaaggacg cttcttaaac      720
tcattattca accaagaagt tcaaattccc ttgaccgaaa gttactgtgg cccatgtcct      780
aaaaactgga tatgttacaa aaataactgc taccaatttt ttgatgagag taaaaactgg      840
tatgagagcc aggcttcttg tatgtctcaa aatgccagcc ttctgaaagt atacagcaaa      900
gaggaccagg atttacttaa actggtgaag tcagatcatt ggatgggact agtacacatt      960
ccaacaaatg gatcttggca gtgggaagat ggctccattc tctcacccaa cctactaaca     1020
ataattgaaa tgcagaaggg agactgtgca ctctatgcct cgagctttaa aggcgatata     1080
gaaaactgtt caactccaaa tacatacatc tgcatgcaaa ggactgtg                 1128

<210> SEQ ID NO 75
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152E/Y199E eNKG2D13 fusion

<400> SEQUENCE: 75
atggacccga aaagctgcga caagactcac acttgtccgc cgtgccccgc ccccgaactg       60
ctgggtggcc cctccgtgtt cctgttcccg cctaagccta aggacaccct tatgatcagc      120
cgcacccctg aagtgacctg tgtcgtcgtg gatgtgtcac acgaggaccc ggaggtcaag      180
ttcaattggt acgtggacgg cgtggaagtg cataacgcaa agaccaagcc tcgggaggaa      240
cagtacaact cgacctaccg cgtggtgtca gtcctgactg tgctgcacca ggactggctg      300
aacgggaagg agtacaagtg caaagtgtcg aacaaggccc tgccggctcc aattgaaaag      360
accatcagca aggccaaggg ccagccaagg gaaccacagg tgtacaccct ccctccttcc      420
cgggacgagc tgaccaaaaa ccaagtgtcc ctgacttgcc ttgtgaaggg gttctaccct      480
tctgacattg ccgtcgaatg ggaatcgaac ggacagcctg aaaacaacta taagactacc      540
ccgcccgtgc tggattccga cggaagcttc ttcctgtact ccaagctgac cgtggacaag      600
tcgagatggc agcagggaaa tgtgttcagc tgctccgtga tgcatgaggc gctgcacaac      660
cactacaccc agaagtcact gagcctctcc cccggaaaga tcgaaggacg cttcttaaac      720
tcattattca accaagaagt tcaaattccc ttgaccgaaa gttactgtgg cccatgtcct      780
aaaaactgga tatgttacaa aaataactgc taccaatttt ttgatgagag taaaaactgg      840
tatgagagcc aggcttcttg tatgtctcaa aatgccagcc ttctgaaagt atacagcaaa      900
gaggaccagg atttacttaa actggtgaag tcagagcatt ggatgggact agtacacatt      960
ccaacaaatg gatcttggca gtgggaagat ggctccattc tctcacccaa cctactaaca     1020
ataattgaaa tgcagaaggg agactgtgca ctctatgcct cgagctttaa aggcgagata     1080
gaaaactgtt caactccaaa tacatacatc tgcatgcaaa ggactgtg                 1128

<210> SEQ ID NO 76
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152L eNKG2D14 fusion

<400> SEQUENCE: 76
atggacccga aaagctgcga caagactcac acttgtccgc cgtgccccgc ccccgaactg       60
```

```
ctgggtggcc cctccgtgtt cctgttcccg cctaagccta aggacaccct tatgatcagc    120
cgcacccctg aagtgacctg tgtcgtcgtg gatgtgtcac acgaggaccc ggaggtcaag    180
ttcaattggt acgtggacgg cgtggaagtg cataacgcaa agaccaagcc tcgggaggaa    240
cagtacaact cgacctaccg cgtggtgtca gtcctgactg tgctgcacca ggactggctg    300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcactgcatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggctatata   1080
gaaaactgtt caactccaaa tacatacatc tgcatgcaaa ggactgtg                1128

<210> SEQ ID NO 77
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152F/Y199F eNKG2D15 fusion

<400> SEQUENCE: 77
atggacccga aaagctgcga caagactcac acttgtccgc cgtgccccgc ccccgaactg     60
ctgggtggcc cctccgtgtt cctgttcccg cctaagccta aggacaccct tatgatcagc    120
cgcacccctg aagtgacctg tgtcgtcgtg gatgtgtcac acgaggaccc ggaggtcaag    180
ttcaattggt acgtggacgg cgtggaagtg cataacgcaa agaccaagcc tcgggaggaa    240
cagtacaact cgacctaccg cgtggtgtca gtcctgactg tgctgcacca ggactggctg    300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcattccatt ggatgggact agtacacatt    960
```

```
ccaacaaatg atcttggca gtgggaagat ggctccattc tctcacccaa cctactaaca    1020
ataattgaaa tgcagaaggg agactgtgca ctctatgcct cgagctttaa aggcttcata    1080
gaaaactgtt caactccaaa tacatacatc tgcatgcaaa ggactgtg                1128
```

```
<210> SEQ ID NO 78
<211> LENGTH: 181
<212> TYPE: PRT
<213> ORGANISM: Artificial sequence
<220> FEATURE:
<223> OTHER INFORMATION: Synthetic peptide MICwed alpha1-alpha2

<400> SEQUENCE: 78

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr
            180
```

```
<210> SEQ ID NO 79
<211> LENGTH: 543
<212> TYPE: DNA
<213> ORGANISM: Artificial sequence
<220> FEATURE:
<223> OTHER INFORMATION: Synthetic polynucleotide, encoding MICwed
      alpha1-alpha2

<400> SEQUENCE: 79
gagcctcaca gcctccggta taatttgact gtactctctt gggatggctc cgtgcagtcc    60
ggctttctga ctgaagttca tctcgacggt caacctttcc tgcgctgcga ccacaaaaa    120 tgccgcgcca agccccaagg gcagtgggcc gaagatgtac tgggaaacaa gacctgggac    180
cgggagacac gagacctgac aggctggggc aaggacttgc gcatgacact cgcccatatc    240
aaggaccaga aggaaggatt gcactctttg caagagattc gcgtgtgtga atccacgag    300 gacaattcaa cgaggagctc ccagcacttc tattacgatg gagaactctt cttgtcacag    360
aacttggaaa ccaaggaatg gactatgcct cagagctctc gggcacagac tctcgctatg    420
aacgttagaa acttccttaa ggaggatgct atggagaccg atactcacta ccacgccatg    480
```

```
cacgccgact gcctccagga actgcggaga tatctgaagt ccggcgtggt tttgagaaga    540
acc                                                                  543
```

<210> SEQ ID NO 80
<211> LENGTH: 181
<212> TYPE: PRT
<213> ORGANISM: Artificial sequence
<220> FEATURE:
<223> OTHER INFORMATION: Synthetic peptide MIC25 alpha1-alpha2

<400> SEQUENCE: 80

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

Arg Ala Asp Cys Leu Ser Glu Leu Arg Arg Tyr Leu Lys Ser Gly Val
                165                 170                 175

Val Leu Arg Arg Thr
            180

<210> SEQ ID NO 81
<211> LENGTH: 543
<212> TYPE: DNA
<213> ORGANISM: Artificial sequence
<220> FEATURE:
<223> OTHER INFORMATION: Synthetic polynucleotide, encoding MIC25
      alpha1-alpha2

<400> SEQUENCE: 81

```
gagcctcaca gcctccggta taatttgact gtactctctt gggatggctc cgtgcagtcc     60
ggctttctga ctgaagttca tctcgacggt caaccttttcc tgcgctgcga ccgacaaaaa   120
tgccgcgcca gccccaagg gcagtgggcc gaagatgtac tggaaacaa gacctgggac     180 cgggagacac gagacctgac aggctggggc aaggacttgc gcatgacact cgcccatatc    240
aaggaccaga aggaaggatt gcactctttg caagagattc gcgtgtgtga aatccacgag    300
gacaattcaa cgaggagctc ccagcacttc tattacgatg gagaactctt cttgtcacag    360
aacttggaaa ccctcgaatg gactatgcct cagagctctc gggcacagac tctcgctatg    420
aacgttagaa acttccttaa ggaggatgct atggagaccg atactcacta ccacgccatg    480
cgcgccgact gcctctctga actgcggaga tatctgaagt ccggcgtggt tttgagaaga    540
``` acc                                                                543

<210> SEQ ID NO 82
<211> LENGTH: 330
<212> TYPE: PRT
<213> ORGANISM: Artificial sequence
<220> FEATURE:
<223> OTHER INFORMATION: Synthetic peptide human IgG1 heavy chain
      CH1-CH2-CH3 D265A/N297A

<400> SEQUENCE: 82

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 83
<211> LENGTH: 990

```
<212> TYPE: DNA
<213> ORGANISM: Artificial sequence
<220> FEATURE:
<223> OTHER INFORMATION: human IgG1 heavy chain CH1-CH2-CH3 D265A/N297A

<400> SEQUENCE: 83
gcgtcgacca agggcccgtc agtgttcccg ctggccccgt catccaagtc cacgtctggg      60
ggcacagcag ccctgggatg cttggtcaag gactacttcc ccgagcccgt gactgtgtcc     120
tggaactccg gagcactgac ctccggagtg cacaccttc ccgcggtgct gcagtcctcc      180
ggactgtact ccctgtcgtc ggtcgtgacc gtgccgagct cctcgctcgg aacccagacc     240
tacatctgca acgtgaacca caagccctcg aacaccaaag tggacaagaa ggtcgagccc     300
aaaagctgcg acaagactca cacttgtccg ccgtgccccg cccccgaact gctgggtggc     360
ccctccgtgt tcctgttccc gcctaagcct aaggacaccc ttatgatcag ccgcaccccc     420
gaagtgacct gtgtcgtcgt ggcagtgtca cacgaggacc cggaggtcaa gttcaattgg     480
tacgtggacg gcgtggaagt gcataacgca aagaccaagc ctcggaggga acagtacgcc     540
tcgacctacc gcgtggtgtc agtcctgact gtgctgcacc aggactggct gaacgggaag     600
gagtacaagt gcaaagtgtc gaacaaggcc ctgccggctc caattgaaaa gaccatcagc     660
aaggccaagg gccagccaag ggaaccacag gtgtacaccc tccctccttc ccgggacgag     720
ctgaccaaaa accaagtgtc cctgacttgc cttgtgaagg ggttctaccc ttctgacatt     780
gccgtcgaat gggaatcgaa cggacagcct gaaaacaact ataagactac cccgcccgtg     840
ctggattccg acggaagctt cttcctgtac tccaagctga ccgtggacaa gtcgagatgg     900
cagcagggaa atgtgttcag ctgctccgtg atgcatgagg cgctgcacaa ccactacacc     960
cagaagtcac tgagcctctc ccccggaaag                                     990

<210> SEQ ID NO 84
<211> LENGTH: 107
<212> TYPE: PRT
<213> ORGANISM: Artificial sequence
<220> FEATURE:
<223> OTHER INFORMATION: Synthetic peptide human kappa light chain

<400> SEQUENCE: 84

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 85
<211> LENGTH: 321
<212> TYPE: DNA
<213> ORGANISM: Artificial sequence
<220> FEATURE:
<223> OTHER INFORMATION: Synthetic polynucleotide, encoding human kappa
``` light chain

<400> SEQUENCE: 85

```
agaaccgtgg ccgccccgag cgtgttcatt ttccctccct ccgacgagca gttgaaatcg      60
ggcaccgcta gcgtggtctg ccttctcaac aatttctatc cacgggaagc caaagtgcag     120
tggaaggtcg acaacgcgct ccaatccggg aactcacagg aatccgtgac tgagcaggat     180
tccaaggact cgacctactc cctgtcatcc acgctgaccc tgagcaaggc agactacgag     240
aagcacaagg tctacgcctg cgaagtgaca caccagggac tgtccagccc cgtgaccaag     300
agcttcaaca gaggagaatg c                                                321
```

<210> SEQ ID NO 86
<211> LENGTH: 120
<212> TYPE: PRT
<213> ORGANISM: Artificial sequence
<220> FEATURE:
<223> OTHER INFORMATION: Synthetic peptide trastuzumab VH

<400> SEQUENCE: 86

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 87
<211> LENGTH: 360
<212> TYPE: DNA
<213> ORGANISM: Artificial sequence
<220> FEATURE:
<223> OTHER INFORMATION: Synthetic polynucleotide, encoding trastuzumab
      VH

<400> SEQUENCE: 87

```
gaagtccaat tggtcgaatc aggcggtgga ctcgtgcaac tggaggttc gttacgctta      60 tcatgtgctg caagtggatt taatattaaa gataccctaca tccactgggt acgtcaagct    120
cccggcaagg gtctcgagtg gtcgcacgc atttaccca caacggata cacgcgctac       180 gccgattcag tgaagggacg tttcacaatc tctgctgata ctagcaaaaa taccgcatac    240
ctccagatga actctcttag ggccgaggac acagctgtgt actactgtag ccgttgggga    300
ggagacggtt ttacgcaat ggattactgg ggccaaggaa ccctggtcac agtttcatcg     360
```

<210> SEQ ID NO 88
<211> LENGTH: 107
<212> TYPE: PRT
<213> ORGANISM: Artificial sequence
<220> FEATURE:

<223> OTHER INFORMATION: Synthetic peptide trastuzumab VL

<400> SEQUENCE: 88

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 89
<211> LENGTH: 321
<212> TYPE: DNA
<213> ORGANISM: Artificial sequence
<220> FEATURE:
<223> OTHER INFORMATION: Synthetic polynucleotide, encoding trastuzumab VL

<400> SEQUENCE: 89

```
gatatccaaa tgactcaatc accatcttca ctctccgcga gcgtgggtga tcgggtcacc      60
atcacatgta gggcgagcca agatgtgaat accgccgtcg cgtggtatca acaaaagccg     120
ggaaaagcac caaaactgct tatatactct gcatccttcc tgtactctgg ggtgccaagc     180
cggttctccg gtagtagatc tggtactgac tttacactca ctatcagcag tctgcaacct     240
gaggactttg cgacatacta ttgccagcag cactacacaa ccccacctac atttggtcag     300
gggacaaagg tggagatcaa g                                                321
```

<210> SEQ ID NO 90
<211> LENGTH: 121
<212> TYPE: PRT
<213> ORGANISM: Artificial sequence
<220> FEATURE:
<223> OTHER INFORMATION: Synthetic peptide rituximab VH

<400> SEQUENCE: 90

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110
```

Ala Gly Thr Thr Val Thr Val Ser Ala
        115                 120

<210> SEQ ID NO 91
<211> LENGTH: 363
<212> TYPE: DNA
<213> ORGANISM: Artificial sequence
<220> FEATURE:
<223> OTHER INFORMATION: Synthetic polynucleotide, encoding rituximab VH

<400> SEQUENCE: 91

```
caagttcagc ttcagcagcc gggggctgag ttggtgaaac ccggggccag tgtgaagatg      60
agctgtaaag cgagcggcta caccttcact tcttataata tgcattgggt taagcaaacg     120
ccaggaaggg ggctggagtg gatcggcgct atttacccag gtaacggtga cacatcatat     180
aaccaaaagt ttaagggaaa ggcaacccct acagcggaca gagtagctc aaccgcatac      240
atgcaactgt caagccttac ctccgaagac agcgcagtgt actactgcgc cagaagcacc     300
tactatgggg gtgattggta cttcaacgtc tgggggggctg gcaccacagt gactgtaagc    360
gca                                                                   363
```

<210> SEQ ID NO 92
<211> LENGTH: 106
<212> TYPE: PRT
<213> ORGANISM: Artificial sequence
<220> FEATURE:
<223> OTHER INFORMATION: Synthetic peptide rituximab VL

<400> SEQUENCE: 92

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 93
<211> LENGTH: 318
<212> TYPE: DNA
<213> ORGANISM: Artificial sequence
<220> FEATURE:
<223> OTHER INFORMATION: Synthetic polynucleotide, encoding rituximab VL

<400> SEQUENCE: 93

```
cagatcgtgt tgtcccaatc acccgcaatt ctctctgcga gcccagggga aaggtgacc      60
atgacttgcc gcgcttcaag ttccgtatcc tacattcact ggttccagca gaagcccgga    120
agttcccta agccctggat ctatgctaca tccaatctgg caagcggtgt tcccgttaga     180
ttttccggaa gcgggtctgg aaccagttac agtctgacta ttccagggt cgaggccgaa    240
gatgcggcta cttattattg ccaacagtgg acctctaacc cacccacatt cggcggcggc    300
actaagttgg aaattaag                                                  318
```

<210> SEQ ID NO 94
<211> LENGTH: 450
<212> TYPE: PRT
<213> ORGANISM: Artificial sequence
<220> FEATURE:
<223> OTHER INFORMATION: Synthetic peptide trastuzumab heavy chain

<400> SEQUENCE: 94

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 95
<211> LENGTH: 1350
<212> TYPE: DNA
<213> ORGANISM: Artificial sequence
<220> FEATURE:
<223> OTHER INFORMATION: Synthetic polynucleotide, encoding trastuzumab
      heavy chain

<400> SEQUENCE: 95
gaagtccaat tggtcgaatc aggcggtgga ctcgtgcaac ctggaggttc gttacgctta      60
tcatgtgctg caagtggatt taatattaaa gataccaca tccactgggt acgtcaagct     120
cccggcaagg gtctcgagtg gtcgcacgc atttacccca ccaacggata cacgcgctac     180
gccgattcag tgaagggacg tttcacaatc tctgctgata ctagcaaaaa taccgcatac     240
ctccagatga actctcttag ggccgaggac acagctgtgt actactgtag ccgttgggga     300
ggagacggtt tttacgcaat ggattactgg ggccaaggaa ccctggtcac agtttcatcg     360
gcgtcgacca agggcccgtc agtgttcccg ctggccccgt catccaagtc cacgtctggg     420
ggcacagcag ccctgggatg cttggtcaag gactacttcc ccgagcccgt gactgtgtcc     480
tggaactccg gagcactgac ctccggagtg cacacctttc ccgcggtgct gcagtcctcc     540
ggactgtact ccctgtcgtc ggtcgtgacc gtgccgagct cctcgctcgg aacccagacc     600
tacatctgca acgtgaacca caagccctcg aacaccaaag tggacaagaa ggtcgagccc     660
aaaagctgcg acaagactca cacttgtccg ccgtgccccg cccccgaact gctgggtggc     720
ccctccgtgt tcctgttccc gcctaagcct aaggacaccc ttatgatcag ccgcacccct     780
gaagtgacct gtgtcgtcgt ggatgtgtca cacgaggacc cggaggtcaa gttcaattgg     840
tacgtggacg gcgtggaagt gcataacgca aagaccaagc ctcgggagga acagtacaac     900
tcgacctacc gcgtggtgtc agtcctgact gtgctgcacc aggactggct gaacgggaag     960
gagtacaagt gcaaagtgtc gaacaaggcc ctgccggctc aattgaaaa gaccatcagc    1020 aaggccaagg gccagccaag ggaaccacag gtgtacaccc tccctccttc ccgggacgag    1080
ctgaccaaaa accaagtgtc cctgacttgc cttgtgaagg ggttctaccc ttctgacatt    1140
gccgtcgaat gggaatcgaa cggacagcct gaaacaact ataagactac cccgcccgtg    1200
ctggattccg acggaagctt cttcctgtac tccaagctga ccgtggacaa gtcgagatgg    1260
cagcagggaa atgtgttcag ctgctccgtg atgcatgagg cgctgcacaa ccactacacc    1320
cagaagtcac tgagcctctc ccccggaaag                                    1350

<210> SEQ ID NO 96
<211> LENGTH: 213
```

```
<212> TYPE: PRT
<213> ORGANISM: Artificial sequence
<220> FEATURE:
<223> OTHER INFORMATION: Synthetic peptide trastuzumab light chain

<400> SEQUENCE: 96
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

```
<210> SEQ ID NO 97
<211> LENGTH: 642
<212> TYPE: DNA
<213> ORGANISM: Artificial sequence
<220> FEATURE:
<223> OTHER INFORMATION: Synthetic polynucleotide, encoding trastuzumab
      light chain

<400> SEQUENCE: 97
```
gatatccaaa tgactcaatc accatcttca ctctccgcga gcgtgggtga tcgggtcacc      60
atcacatgta gggcgagcca agatgtgaat accgccgtcg cgtggtatca acaaaagccg     120
ggaaaagcac caaaactgct tatatactct gcatccttcc tgtactctgg ggtgccaagc     180
cggttctccg gtagtagatc tggtactgac tttacactca ctatcagcag tctgcaacct     240
gaggactttg cgacatacta ttgccagcag cactacacaa ccccacctac atttggtcag     300
gggacaaagg tggagatcaa gaccgtggcc gccccgagcg tgttcatttt ccctccctcc     360
gacgagcagt tgaaatcggg caccgctagc gtggtctgcc ttctcaacaa tttctatcca     420
cgggaagcca agtgcagtg gaaggtcgac aacgcgctcc aatccgggaa ctcacaggaa     480
tccgtgactg agcaggattc caaggactcg acctactccc tgtcatccac gctgaccctg     540
agcaaggcag actacgagaa gcacaaggtc tacgcctgcg aagtgacaca ccagggactg     600

```
tccagccccg tgaccaagag cttcaacaga ggagaatgct ag          642
```

<210> SEQ ID NO 98
<211> LENGTH: 451
<212> TYPE: PRT
<213> ORGANISM: Artificial sequence
<220> FEATURE:
<223> OTHER INFORMATION: Synthetic peptide rituximab heavy chain

<400> SEQUENCE: 98

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 99
<211> LENGTH: 1353
<212> TYPE: DNA
<213> ORGANISM: Artificial sequence
<220> FEATURE:
<223> OTHER INFORMATION: Synthetic polynucleotide, encoding rituximab
      heavy chain

<400> SEQUENCE: 99
caagttcagc ttcagcagcc gggggctgag ttggtgaaac cggggccag tgtgaagatg     60 agctgtaaag cgagcggcta caccttcact tcttataata tgcattgggt taagcaaacg    120
ccaggaaggg ggctggagtg gatcggcgct atttacccag gtaacggtga cacatcatat    180
aaccaaaagt ttaagggaaa ggcaaccctc acagcggaca gagtagctc aaccgcatac    240 atgcaactgt caagccttac ctccgaagac agcgcagtgt actactgcgc cagaagcacc    300
tactatgggg gtgattggta cttcaacgtc tggggggctg gcaccacagt gactgtaagc    360
gcagcgtcga ccaagggccc gtcagtgttc ccgctggccc cgtcatccaa gtccacgtct    420 ggggggcacag cagccctggg atgcttggtc aaggactact ccccgagcc cgtgactgtg    480 tcctggaact ccggagcact gacctccgga gtgcacacct tcccgcggt gctgcagtcc    540 tccggactgt actccctgtc gtcggtcgtg accgtgccga gctcctcgct cggaacccag    600
acctacatct gcaacgtgaa ccacaagccc tcgaacacca agtggacaa gaaggtcgag    660 cccaaaagct gcgacaagac tcacacttgt ccgccgtgcc cgccccga actgctgggt    720 ggccctccg tgttcctgtt cccgcctaag cctaaggaca cccttatgat cagccgcacc    780
cctgaagtga cctgtgtcgt cgtggatgtg tcacacgagg acccggaggt caagttcaat    840
tggtacgtgg acggcgtgga agtgcataac gcaaagacca gcctcggga ggaacagtac    900 aactcgacct accgcgtggt gtcagtcctg actgtgctgc accaggactg gctgaacggg    960
aaggagtaca gtgcaaagt gtcgaacaag gccctgccgg ctccaattga aaagaccatc   1020
agcaaggcca agggccagcc aagggaacca caggtgtaca cctccctcc ttccggac    1080 gagctgacca aaaccaagt gtccctgact tgccttgtga aggggttcta cccttctgac   1140
attgccgtcg aatgggaatc gaacggacag cctgaaaaca actataagac taccccgccc   1200
gtgctggatt ccgacggaag cttcttcctg tactccaagc tgaccgtgga caagtcgaga   1260
tggcagcagg gaaatgtgtt cagctgctcc gtgatgcatg aggcgctgca caaccactac   1320
acccagaagt cactgagcct ctccccccgga aag                              1353

```
<210> SEQ ID NO 100
<211> LENGTH: 212
<212> TYPE: PRT
<213> ORGANISM: Artificial sequence
<220> FEATURE:
<223> OTHER INFORMATION: Synthetic peptide rituximab light chain

<400> SEQUENCE: 100

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 101
<211> LENGTH: 639
<212> TYPE: DNA
<213> ORGANISM: Artificial sequence
<220> FEATURE:
<223> OTHER INFORMATION: Synthetic polynucleotide, encoding rituximab
      light chain

<400> SEQUENCE: 101
cagatcgtgt tgtcccaatc acccgcaatt ctctctgcga gcccagggga gaaggtgacc      60
atgacttgcc gcgcttcaag ttccgtatcc tacattcact ggttccagca gaagcccgga     120
agttccccta agccctggat ctatgctaca tccaatctgg caagcggtgt tcccgttaga     180
ttttccggaa gcgggtctgg aaccagttac agtctgacta tttccagggt cgaggccgaa     240
gatgcggcta cttattattg caacagtgg acctctaacc cacccacatt cggcggcggc     300
actaagttgg aaattaagac cgtggccgcc ccgagcgtgt tcattttccc tcctccgac      360 gagcagttga atcgggcac cgctagcgtg gtctgccttc tcaacaattt ctatccacgg     420
gaagccaaag tgcagtggaa ggtcgacaac gcgctccaat ccgggaactc acaggaatcc     480
gtgactgagc aggattccaa ggactcgacc tactccctgt catccacgct gaccctgagc     540
```
aaggcagact acgagaagca caggtctac gcctgcgaag tgacacacca gggactgtcc    600
agccccgtga ccaagagctt caacagagga gaatgctag                          639

<210> SEQ ID NO 102
<211> LENGTH: 634
<212> TYPE: PRT
<213> ORGANISM: Artificial sequence
<220> FEATURE:
<223> OTHER INFORMATION: Synthetic peptide trastuzumab HC_MICwed

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ala Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr

```
             340             345              350
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Ser Glu Pro His Ser Leu Arg Tyr Asn Leu Thr Val
    450                 455                 460

Leu Ser Trp Asp Gly Ser Val Gln Ser Gly Phe Leu Thr Glu Val His
465                 470                 475                 480

Leu Asp Gly Gln Pro Phe Leu Arg Cys Asp Arg Gln Lys Cys Arg Ala
                485                 490                 495

Lys Pro Gln Gly Gln Trp Ala Glu Asp Val Leu Gly Asn Lys Thr Trp
            500                 505                 510

Asp Arg Glu Thr Arg Asp Leu Thr Gly Trp Gly Lys Asp Leu Arg Met
        515                 520                 525

Thr Leu Ala His Ile Lys Asp Gln Lys Glu Gly Leu His Ser Leu Gln
    530                 535                 540

Glu Ile Arg Val Cys Glu Ile His Glu Asp Asn Ser Thr Arg Ser Ser
545                 550                 555                 560

Gln His Phe Tyr Tyr Asp Gly Glu Leu Phe Leu Ser Gln Asn Leu Glu
                565                 570                 575

Thr Lys Glu Trp Thr Met Pro Gln Ser Ser Arg Ala Gln Thr Leu Ala
            580                 585                 590

Met Asn Val Arg Asn Phe Leu Lys Glu Asp Ala Met Glu Thr Asp Thr
        595                 600                 605

His Tyr His Ala Met His Ala Asp Cys Leu Gln Glu Leu Arg Arg Tyr
    610                 615                 620

Leu Lys Ser Gly Val Val Leu Arg Arg Thr
625                 630

<210> SEQ ID NO 103
<211> LENGTH: 1902
<212> TYPE: DNA
<213> ORGANISM: Artificial sequence
<220> FEATURE:
<223> OTHER INFORMATION: Synthetic polynucleotide, encoding trastuzumab
      HC_MICwed

<400> SEQUENCE: 103
gaagtccaat tggtcgaatc aggcggtgga ctcgtgcaac ctggaggttc gttacgctta      60
tcatgtgctg caagtggatt taatattaaa gatacctaca tccactgggt acgtcaagct     120
cccggcaagg gtctcgagtg gtcgcacgc atttaccccca ccaacggata cacgcgctac     180
gccgattcag tgaagggacg tttcacaatc tctgctgata ctagcaaaaa taccgcatac     240
ctccagatga actctcttag ggccgaggac acagctgtgt actactgtag ccgttgggga     300
ggagacggtt tttacgcaat ggattactgg ggccaaggaa ccctggtcac agtttcatcg     360
```

```
gcgtcgacca agggcccgtc agtgttcccg ctggccccgt catccaagtc cacgtctggg    420
ggcacagcag ccctgggatg cttggtcaag gactacttcc ccgagcccgt gactgtgtcc    480
tggaactccg gagcactgac ctccggagtg cacacctttc ccgcggtgct gcagtcctcc    540
ggactgtact ccctgtcgtc ggtcgtgacc gtgccgagct cctcgctcgg aacccagacc    600
tacatctgca acgtgaacca caagccctcg aacaccaaag tggacaagaa ggtcgagccc    660
aaaagctgcg acaagactca cacttgtccg ccgtgccccg cccccgaact gctgggtggc    720
ccctccgtgt tcctgttccc gcctaagcct aaggacaccc ttatgatcag ccgcacccct    780
gaagtgacct gtgtcgtcgt ggcagtgtca cacgaggacc cggaggtcaa gttcaattgg    840
tacgtggacg gcgtggaagt gcataacgca aagaccaagc ctcgggagga acagtacgcc    900
tcgacctacc gcgtggtgtc agtcctgact gtgctgcacc aggactggct gaacgggaag    960
gagtacaagt gcaaagtgtc gaacaaggcc ctgccggctc caattgaaaa gaccatcagc   1020
aaggccaagg gccagccaag ggaaccacag gtgtacaccc tccctccttc ccgggacgag   1080
ctgaccaaaa accaagtgtc cctgacttgc cttgtgaagg ggttctaccc ttctgacatt   1140
gccgtcgaat gggaatcgaa cggacagcct gaaaacaact ataagactac cccgcccgtg   1200
ctggattccg acggaagctt cttcctgtac tccaagctga ccgtggacaa gtcgagatgg   1260
cagcagggaa atgtgttcag ctgctccgtg atgcatgagg cgctgcacaa ccactacacc   1320
cagaagtcac tgagcctctc ccccggagga ggtggcagcg agcctcacag cctccggtat   1380
aatttgactg tactctcttg ggatggctcc gtgcagtccg gctttctgac tgaagttcat   1440
ctcgacggtc aacctttcct gcgctgcgac cgacaaaaat gccgcgccaa gccccaaggg   1500
cagtgggccg aagatgtact gggaaacaag acctgggacc gggagacacg agacctgaca   1560
ggctggggca aggacttgcg catgacactc gcccatatca aggaccagaa ggaaggattg   1620
cactctttgc aagagattcg cgtgtgtgaa atccacgagg acaattcaac gaggagctcc   1680
cagcacttct attacgatgg agaactcttc ttgtcacaga acttggaaac caaggaatgg   1740
actatgcctc agagctctcg ggcacagact ctcgctatga acgttagaaa cttccttaag   1800
gaggatgcta tggagaccga tactcactac cacgccatgc acgccgactg cctccaggaa   1860
ctgcggagat atctgaagtc cggcgtggtt ttgagaagaa cc                      1902
```

<210> SEQ ID NO 104
<211> LENGTH: 634
<212> TYPE: PRT
<213> ORGANISM: Artificial sequence
<220> FEATURE:
<223> OTHER INFORMATION: Synthetic peptide trastuzumab HC_MIC25

<400> SEQUENCE: 104

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ala Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Ala Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Gly Gly Gly Ser Glu Pro His Ser Leu Arg Tyr Asn Leu Thr Val
            450                 455                 460

Leu Ser Trp Asp Gly Ser Val Gln Ser Gly Phe Leu Thr Glu Val His
465                 470                 475                 480

Leu Asp Gly Gln Pro Phe Leu Arg Cys Asp Arg Gln Lys Cys Arg Ala
                485                 490                 495

Lys Pro Gln Gly Gln Trp Ala Glu Asp Val Leu Gly Asn Lys Thr Trp
            500                 505                 510
```

```
Asp Arg Glu Thr Arg Asp Leu Thr Gly Trp Gly Lys Asp Leu Arg Met
            515                 520                 525

Thr Leu Ala His Ile Lys Asp Gln Lys Glu Gly Leu His Ser Leu Gln
            530                 535                 540

Glu Ile Arg Val Cys Glu Ile His Glu Asp Asn Ser Thr Arg Ser Ser
545                 550                 555                 560

Gln His Phe Tyr Tyr Asp Gly Glu Leu Phe Leu Ser Gln Asn Leu Glu
                565                 570                 575

Thr Leu Glu Trp Thr Met Pro Gln Ser Ser Arg Ala Gln Thr Leu Ala
            580                 585                 590

Met Asn Val Arg Asn Phe Leu Lys Glu Asp Ala Met Glu Thr Asp Thr
            595                 600                 605

His Tyr His Ala Met Arg Ala Asp Cys Leu Ser Glu Leu Arg Arg Tyr
            610                 615                 620

Leu Lys Ser Gly Val Val Leu Arg Arg Thr
625                 630
```

<210> SEQ ID NO 105
<211> LENGTH: 1902
<212> TYPE: DNA
<213> ORGANISM: Artificial sequence
<220> FEATURE:
<223> OTHER INFORMATION: Synthetic polynucleotide, encoding trastuzumab
      HC_MIC25

<400> SEQUENCE: 105

```
gaagtccaat tggtcgaatc aggcggtgga ctcgtgcaac ctggaggttc gttacgctta      60
tcatgtgctg caagtggatt taatattaaa gatacctaca tccactgggt acgtcaagct     120
cccggcaagg gtctcgagtg gtcgcacgc atttacccca ccaacggata cacgcgctac     180
gccgattcag tgaagggacg tttcacaatc tctgctgata ctagcaaaaa taccgcatac     240
ctccagatga actctcttag ggccgaggac acagctgtgt actactgtag ccgttgggga     300
ggagacggtt tttacgcaat ggattactgg ggccaaggaa ccctggtcac agtttcatcg     360
gcgtcgacca agggcccgtc agtgttcccg ctggccccgt catccaagtc cacgtctggg     420
ggcacagcag ccctgggatg cttggtcaag gactacttcc ccgagcccgt gactgtgtcc     480
tggaactccg gagcactgac ctccggagtg cacaccttc  ccgcggtgct gcagtcctcc     540
ggactgtact ccctgtcgtc ggtcgtgacc gtgccgagct cctcgctcgg aacccagacc     600
tacatctgca acgtgaacca caagccctcg aacaccaaag tggacaagaa ggtcgagccc     660
aaaagctgcg acaagactca cacttgtccg ccgtgccccg cccccgaact gctgggtggc     720
ccctccgtgt tcctgttccc gcctaagcct aaggacaccc ttatgatcag ccgcacccct     780
gaagtgacct gtgtcgtcgt ggcagtgtca cacgaggacc cggaggtcaa gttcaattgg     840
tacgtggacg gcgtggaagt gcataacgca aagaccaagc ctcgggagga acagtacgcc     900
tcgacctacc gcgtggtgtc agtcctgact gtgctgcacc aggactggct gaacgggaag     960
gagtacaagt gcaaagtgtc gaacaaggcc ctgccggctc aattgaaaaa gaccatcagc    1020
aaggccaagg gccagccaag ggaaccacag gtgtacaccc tccctccttc ccgggacgag    1080
ctgaccaaaa accaagtgtc cctgacttgc cttgtgaagg ggttctaccc ttctgacatt    1140
gccgtcgaat gggaatcgaa cggacagcct gaaaacaact ataagactac cccgcccgtg    1200
ctggattccg acggaagctt cttcctgtac tccaagctga ccgtggacaa gtcgagatgg    1260
cagcagggaa atgtgttcag ctgctccgtg atgcatgagg cgctgcacaa ccactacacc    1320
```

```
cagaagtcac tgagcctctc ccccggagga ggtggcagcg agcctcacag cctccggtat    1380
aatttgactg tactctcttg ggatggctcc gtgcagtccg gctttctgac tgaagttcat    1440
ctcgacggtc aacctttcct gcgctgcgac cgacaaaaat gccgcgccaa gccccaaggg    1500
cagtgggccg aagatgtact gggaaacaag acctgggacc gggagacacg agacctgaca    1560
ggctggggca aggacttgcg catgacactc gcccatatca aggaccagaa ggaaggattg    1620
cactctttgc aagagattcg cgtgtgtgaa atccacgagg acaattcaac gaggagctcc    1680
cagcacttct attacgatgg agaactcttc ttgtcacaga acttggaaac cctcgaatgg    1740
actatgcctc agagctctcg ggcacagact ctcgctatga acgttagaaa cttccttaag    1800
gaggatgcta tggagaccga tactcactac cacgccatgc gcgccgactg cctctctgaa    1860
ctgcggagat atctgaagtc cggcgtggtt ttgagaagaa cc                      1902
```

<210> SEQ ID NO 106
<211> LENGTH: 404
<212> TYPE: PRT
<213> ORGANISM: Artificial sequence
<220> FEATURE:
<223> OTHER INFORMATION: Synthetic peptide rituximab LC_ULBP2.wt

<400> SEQUENCE: 106

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Ala Pro Thr Ser Ser Gly Gly Gly Gly Ser
    210                 215                 220

Glu Pro His Ser Leu Ser Tyr Asp Ile Thr Val Ile Pro Lys Phe Arg
225                 230                 235                 240

Pro Gly Pro Arg Trp Cys Ala Val Gln Gly Gln Val Asp Glu Lys Thr
                245                 250                 255

Phe Leu His Tyr Asp Cys Gly Asn Lys Thr Val Thr Pro Val Ser Pro
```

```
                260               265               270
Leu Gly Lys Lys Leu Asn Val Thr Thr Ala Trp Lys Ala Gln Asn Pro
            275                 280                 285

Val Leu Arg Glu Val Val Asp Ile Leu Thr Glu Gln Leu Arg Asp Ile
        290                 295                 300

Gln Leu Glu Asn Tyr Thr Pro Lys Glu Pro Leu Thr Leu Gln Ala Arg
305                 310                 315                 320

Met Ser Cys Glu Gln Lys Ala Glu Gly His Ser Ser Gly Ser Trp Gln
                325                 330                 335

Phe Ser Phe Asp Gly Gln Ile Phe Leu Leu Phe Asp Ser Glu Lys Arg
            340                 345                 350

Met Trp Thr Thr Val His Pro Gly Ala Arg Lys Met Lys Glu Lys Trp
        355                 360                 365

Glu Asn Asp Lys Val Val Ala Met Ser Phe His Tyr Phe Ser Met Gly
            370                 375                 380

Asp Cys Ile Gly Trp Leu Glu Asp Phe Leu Met Gly Met Asp Ser Thr
385                 390                 395                 400

Leu Glu Pro Ser
```

<210> SEQ ID NO 107
<211> LENGTH: 1212
<212> TYPE: DNA
<213> ORGANISM: Artificial sequence
<220> FEATURE:
<223> OTHER INFORMATION: Synthetic polynucleotide, encoding rituximab
      LC_ULBP2.wt

<400> SEQUENCE: 107

```
cagatcgtgt tgtcccaatc acccgcaatt ctctctgcga gcccagggga gaaggtgacc    60
atgacttgcc gcgcttcaag ttccgtatcc tacattcact ggttccagca gaagcccgga   120
agttccccta agccctggat ctatgctaca tccaatctgg caagcggtgt tcccgttaga   180
ttttccggaa gcgggtctgg aaccagttac agtctgacta tttccagggt cgaggccgaa   240
gatgcggcta cttattattg ccaacagtgg acctctaacc cacccacatt cggcggcggc   300
actaagttgg aaattaagcg gaccgtggcc gccccgagcg tgttcatttt ccctcccctcc   360
gacgagcagt tgaaatcggg caccgctagc gtggtctgcc ttctcaacaa tttctatcca   420
cgggaagcca agtgcagtg gaaggtcgac aacgcgctcc aatccgggaa ctcacaggaa   480
tccgtgactg agcaggattc caaggactcg acctactccc tgtcatccac gctgaccctg   540
agcaaggcag actacgagaa gcacaaggtc tacgcctgcg aagtgacaca ccagggactg   600
tccagccccg tgaccaagag cttcaacaga ggagaatgcg cacctacctc aagctctgga   660
ggaggtggca gcgagcccca tagtctgagc tacgacatca cagttattcc caagttcagg   720
cccggaccgc gctggtgtgc cgtgcaagga caagtcgacg aaaaaacctt tcttcattac   780
gattgcggaa ataagactgt aacgccagtc tctccttag gtaagaagtt aaacgtcact   840
acggcgtgga aggcacaaaa ccccgtcctg cgcgaggtcg tcgacatcct gactgaacaa   900
ttgcgcgaca tccagctcga gaattacact ccaaaggagc ctcttaccct gcaggctaga   960
atgtcttgcg agcaaaaggc agagggccac tcctccggca gctggcagtt cagtttcgac  1020
ggacaaatct ttctgttat cgattcagag aagagaatgt ggactacagt tcaccccggt  1080
gcccgtaaaa tgaaggagaa gtgggaaaac gacaaagtgg tggcgatgtc attccactat  1140
ttctcgatgg gagactgcat cggttggctg gaagatttcc tcatgggtat ggactccact  1200
```
ttggagccat cg                                                        1212

<210> SEQ ID NO 108
<211> LENGTH: 187
<212> TYPE: PRT
<213> ORGANISM: Artificial sequence
<220> FEATURE:
<223> OTHER INFORMATION: Synthetic peptide ULPB2 alpha1-alpha2 variant
      R80W

<400> SEQUENCE: 108

Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
    130                 135                 140

Glu Asn Asp Lys Val Val Ala Met Ser Phe His Tyr Phe Ser Met Gly
145                 150                 155                 160

Asp Cys Ile Gly Trp Leu Glu Asp Phe Leu Met Gly Met Asp Ser Thr
                165                 170                 175

Leu Glu Pro Ser Ala Gly Ala Pro Pro Met Val
            180                 185

<210> SEQ ID NO 109
<211> LENGTH: 540
<212> TYPE: DNA
<213> ORGANISM: Artificial sequence
<220> FEATURE:
<223> OTHER INFORMATION: Synthetic polynucleotide, encoding ULPB2
      alpha1-alpha2 variant R80W

<400> SEQUENCE: 109
gagccccata gtctgagcta cgacatcaca gttattccca agttcaggcc cggaccgcgc      60
tggtgtgccg tgcaaggaca gtcgacgaa aaaacctttc ttcattacga ttgcggaaat     120
aagactgtaa cgccagtctc tcctttaggt aagaagttaa acgtcactac ggcgtggaag     180
gcacaaaacc ccgtcctgcg cgaggtcgtc gacatcctga ctgaacaatt gtgggacatc     240
cagctcgaga attacactcc aaaggagcct cttaccctgc aggctagaat gtcttgcgag     300
caaaaggcag agggccactc ctccggcagc tggcagttca gtttcgacgg acaaatcttt     360
ctgttattcg attcagagaa gagaatgtgg actacagttc accccggtgc ccgtaaaatg     420
aaggagaagt gggaaaacga caaagtggtg gcgatgtcat tccactattt ctcgatggga     480
gactgcatcg gttggctgga agatttcctc atgggtatgg actccacttt ggagccatcg     540

-continued

<210> SEQ ID NO 110
<211> LENGTH: 513
<212> TYPE: DNA
<213> ORGANISM: Artificial sequence
<220> FEATURE:
<223> OTHER INFORMATION: Synthetic polynucleotide, encoding ULPB2
    alpha1-alpha2 variant R80W NNK library
<220> FEATURE:
<221> NAME/KEY: misc_feature
<222> LOCATION: (457)..(458)
<223> OTHER INFORMATION: n is a, c, g, or t
<220> FEATURE:
<221> NAME/KEY: misc_feature
<222> LOCATION: (460)..(461)
<223> OTHER INFORMATION: n is a, c, g, or t
<220> FEATURE:
<221> NAME/KEY: misc_feature
<222> LOCATION: (463)..(464)
<223> OTHER INFORMATION: n is a, c, g, or t
<220> FEATURE:
<221> NAME/KEY: misc_feature
<222> LOCATION: (466)..(467)
<223> OTHER INFORMATION: n is a, c, g, or t
<220> FEATURE:
<221> NAME/KEY: misc_feature
<222> LOCATION: (469)..(470)
<223> OTHER INFORMATION: n is a, c, g, or t

<400> SEQUENCE: 110
gagccccata gcctcagcta tgacattacg gtgattccca aatttcgccc aggaccacgt      60
tggtgcgccg tccagggtca ggtagatgaa aagactttcc tgcattatga ttgcggcaat    120
aaaaccgtga cgccggtatc gccgttaggc aaaaaattga atgtcacgac agcgtggaaa    180
gcacagaacc cggtgttgcg cgaggtagtc gatattttga cggaacaact ctgggacatt    240
cagctcgaga attacacccc aaaagaaccg ctgacgctgc aagcgcgtat gtcgtgcgaa    300
caaaaagcag aaggtcactc tagcgggagt tggcagtttt ccttcgatgg cagattttt    360 ctgctgtttg attcggagaa acgcatgtgg actacagtcc acccgggtgc ccggaaaatg    420
aaagagaagt gggagaatga taaagtggtg gccactnnkn nknnknnknn ktccatgggc    480
gattgcattg gctggttaga ggattttctc atg                                  513

<210> SEQ ID NO 111
<211> LENGTH: 180
<212> TYPE: PRT
<213> ORGANISM: Artificial sequence
<220> FEATURE:
<223> OTHER INFORMATION: Synthetic peptide, ULBP2 alpha1-alpha2 variant
    ULBP2.C

<400> SEQUENCE: 111

Glu Pro His Ser Leu Ser Tyr Asp Ile Thr Val Ile Pro Lys Phe Arg
1               5                  10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

```
Phe Ser Phe Asp Gly Gln Ile Phe Leu Leu Phe Asp Ser Glu Lys Arg
            115                 120                 125

Met Trp Thr Thr Val His Pro Gly Ala Arg Lys Met Lys Glu Lys Trp
    130                 135                 140

Glu Asn Asp Lys Val Val Ala Thr Ile Leu Trp Gln Thr Ser Met Gly
145                 150                 155                 160

Asp Cys Ile Gly Trp Leu Glu Asp Phe Leu Met Gly Met Asp Ser Thr
                165                 170                 175

Leu Glu Pro Ser
            180

<210> SEQ ID NO 112
<211> LENGTH: 540
<212> TYPE: DNA
<213> ORGANISM: Artificial sequence
<220> FEATURE:
<223> OTHER INFORMATION: Synthetic polynucleotide, encoding ULBP2
      alpha1-alpha2 variant ULBP2.C

<400> SEQUENCE: 112
gagccccata gtctgagcta cgacatcaca gttattccca gttcaggcc cggaccgcgc      60 tggtgtgccg tgcaaggaca gtcgacgaa aaaacctttc ttcattacga ttgcggaaat     120
aagactgtaa cgccagtctc tcctttaggt aagaagttaa acgtcactac ggcgtggaag    180
gcacaaaacc ccgtcctgcg cgaggtcgtc gacatcctga ctgaacaatt gtgggacatc    240
cagctcgaga attacactcc aaaggagcct cttaccctgc aggctagaat gtcttgcgag    300
caaaaggcag agggccactc ctccggcagc tggcagttca gtttcgacgg acaaatcttt    360
ctgttattcg attcagagaa agaaatgtgg actacagttc accccggtgc ccgtaaaatg    420
aaggagaagt gggaaaacga caaagtggtg gcgactattc tgtggcagac ttcgatggga    480
gactgcatcg gttggctgga agatttcctc atgggtatgg actccacttt ggagccatcg    540

<210> SEQ ID NO 113
<211> LENGTH: 180
<212> TYPE: PRT
<213> ORGANISM: Artificial sequence
<220> FEATURE:
<223> OTHER INFORMATION: Synthetic peptide, ULBP2 alpha1-alpha2 variant
      ULBP2.R

<400> SEQUENCE: 113

Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125
```

```
Met Trp Thr Thr Val His Pro Gly Ala Arg Lys Met Lys Glu Lys Trp
            130                 135                 140
Glu Asn Asp Lys Val Val Ala Thr Leu Leu Trp Gly Trp Ser Met Gly
145                 150                 155                 160
Asp Cys Ile Gly Trp Leu Glu Asp Phe Leu Met Gly Met Asp Ser Thr
                165                 170                 175
Leu Glu Pro Ser
            180
```

<210> SEQ ID NO 114
<211> LENGTH: 540
<212> TYPE: DNA
<213> ORGANISM: Artificial sequence
<220> FEATURE:
<223> OTHER INFORMATION: Synthetic polynucleotide, encoding ULBP2
      alpha1-alpha2 variant ULBP2.R

<400> SEQUENCE: 114

```
gagccccata gtctgagcta cgacatcaca gttattccca agttcaggcc cggaccgcgc      60
tggtgtgccg tgcaaggaca agtcgacgaa aaaacctttc ttcattacga ttgcggaaat     120
aagactgtaa cgccagtctc tcctttaggt aagaagttaa acgtcactac ggcgtggaag     180
gcacaaaacc ccgtcctgcg cgaggtcgtc gacatcctga ctgaacaatt gtgggacatc     240
cagctcgaga attacactcc aaaggagcct cttaccctgc aggctagaat gtcttgcgag     300
caaaaggcag agggccactc ctccggcagc tggcagttca gtttcgacgg acaaatcttt     360
ctgttattcg attcagagaa agaatgtggg actacagttc accccggtgc cgtaaaaatg     420
aaggagaagt gggaaaacga caaagtggtg gcgactttgt tgtgggggtg gtcgatggga     480
gactgcatcg gttggctgga agatttcctc atgggtatgg actccacttt ggagccatcg     540
```

<210> SEQ ID NO 115
<211> LENGTH: 180
<212> TYPE: PRT
<213> ORGANISM: Artificial sequence
<220> FEATURE:
<223> OTHER INFORMATION: Synthetic peptide, ULBP2 alpha1-alpha2 variant
      ULBP2.AA

<400> SEQUENCE: 115

```
Glu Pro His Ser Leu Ser Tyr Asp Ile Thr Val Ile Pro Lys Phe Arg
1               5                   10                  15
Pro Gly Pro Arg Trp Cys Ala Val Gln Gly Gln Val Asp Glu Lys Thr
            20                  25                  30
Phe Leu His Tyr Asp Cys Gly Asn Lys Thr Val Thr Pro Val Ser Pro
        35                  40                  45
Leu Gly Lys Lys Leu Asn Val Thr Thr Ala Trp Lys Ala Gln Asn Pro
    50                  55                  60
Val Leu Arg Glu Val Val Asp Ile Leu Thr Glu Gln Leu Trp Asp Ile
65                  70                  75                  80
Gln Leu Glu Asn Tyr Thr Pro Lys Glu Pro Leu Thr Leu Gln Ala Arg
                85                  90                  95
Met Ser Cys Glu Gln Lys Ala Glu Gly His Ser Ser Gly Ser Trp Gln
            100                 105                 110
Phe Ser Phe Asp Gly Gln Ile Phe Leu Leu Phe Asp Ser Glu Lys Arg
        115                 120                 125
Met Trp Thr Thr Val His Pro Gly Ala Arg Lys Met Lys Glu Lys Trp
    130                 135                 140
```

Glu Asn Asp Lys Val Val Ala Thr Met Phe Trp Ser Trp Ser Met Gly
145                 150                 155                 160

Asp Cys Ile Gly Trp Leu Glu Asp Phe Leu Met Gly Met Asp Ser Thr
                165                 170                 175

Leu Glu Pro Ser
            180

<210> SEQ ID NO 116
<211> LENGTH: 540
<212> TYPE: DNA
<213> ORGANISM: Artificial sequence
<220> FEATURE:
<223> OTHER INFORMATION: Synthetic polynucleotide, encoding ULBP2
      alpha1-alpha2 variant ULBP2.AA

<400> SEQUENCE: 116
gagccccata gtctgagcta cgacatcaca gttattccca gttcaggcc cggaccgcgc      60 tggtgtgccg tgcaaggaca gtcgacgaa aaaacctttc ttcattacga ttgcggaaat     120
aagactgtaa cgccagtctc tcctttaggt aagaagttaa acgtcactac ggcgtggaag    180
gcacaaaacc ccgtcctgcg cgaggtcgtc gacatcctga ctgaacaatt gtgggacatc    240
cagctcgaga attacactcc aaaggagcct cttaccctgc aggctagaat gtcttgcgag    300
caaaaggcag agggccactc ctccggcagc tggcagttca gtttcgacgg acaaatcttt    360
ctgttattcg attcagagaa gagaatgtgg actacagttc accccggtgc ccgtaaaatg    420
aaggagaagt gggaaaacga caaagtggtg gcgactatgt tttggagttg gtcgatggga    480
gactgcatcg gttggctgga agatttcctc atgggtatgg actccacttt ggagccatcg    540

<210> SEQ ID NO 117
<211> LENGTH: 180
<212> TYPE: PRT
<213> ORGANISM: Artificial sequence
<220> FEATURE:
<223> OTHER INFORMATION: Synthetic peptide, ULBP2 alpha1-alpha2 variant
      ULBP2.AB

<400> SEQUENCE: 117

Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
    130                 135                 140

Glu Asn Asp Lys Val Val Ala Thr Leu Met Trp Gln Trp Ser Met Gly
145                 150                 155                 160

Asp Cys Ile Gly Trp Leu Glu Asp Phe Leu Met Gly Met Asp Ser Thr
            165                 170                 175

Leu Glu Pro Ser
            180

<210> SEQ ID NO 118
<211> LENGTH: 540
<212> TYPE: DNA
<213> ORGANISM: Artificial sequence
<220> FEATURE:
<223> OTHER INFORMATION: Synthetic polynucleotide, encoding ULBP2
      alpha1-alpha2 variant ULBP2.AB

<400> SEQUENCE: 118 gagcccata gtctgagcta cgacatcaca gttattccca agttcaggcc cggaccgcgc      60
tggtgtgccg tgcaaggaca gtcgacgaa aaaacctttc ttcattacga ttgcggaaat     120
aagactgtaa cgccagtctc tcctttaggt aagaagttaa acgtcactac ggcgtggaag    180
gcacaaaacc ccgtcctgcg cgaggtcgtc gacatcctga ctgaacaatt gtgggacatc    240
cagctcgaga attacactcc aaaggagcct cttaccctgc aggctagaat gtcttgcgag    300
caaaaggcag agggccactc ctccggcagc tggcagttca gtttcgacgg acaaatcttt    360
ctgttattcg attcagagaa gagaatgtgg actacagttc accccggtgc ccgtaaaatg    420
aaggagaagt gggaaaacga caaagtggtg gcgactctta tgtggcagtg gtcgatggga    480
gactgcatcg gttggctgga agatttcctc atgggtatgg actccacttt ggagccatcg    540

<210> SEQ ID NO 119
<211> LENGTH: 404
<212> TYPE: PRT
<213> ORGANISM: Artificial sequence
<220> FEATURE:
<223> OTHER INFORMATION: Synthetic peptide rituximab LC_ULBP2.C

<400> SEQUENCE: 119

Gln Ile Val Leu Ser Gln Ser Pro Ala Ile Leu Ser Ala Ser Pro Gly
1               5                  10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Ala Pro Thr Ser Ser Gly Gly Gly Gly Ser
    210                 215                 220

Glu Pro His Ser Leu Ser Tyr Asp Ile Thr Val Ile Pro Lys Phe Arg
225                 230                 235                 240

Pro Gly Pro Arg Trp Cys Ala Val Gln Gly Gln Val Asp Glu Lys Thr
                245                 250                 255

Phe Leu His Tyr Asp Cys Gly Asn Lys Thr Val Thr Pro Val Ser Pro
            260                 265                 270

Leu Gly Lys Lys Leu Asn Val Thr Thr Ala Trp Lys Ala Gln Asn Pro
        275                 280                 285

Val Leu Arg Glu Val Val Asp Ile Leu Thr Glu Gln Leu Trp Asp Ile
    290                 295                 300

Gln Leu Glu Asn Tyr Thr Pro Lys Glu Pro Leu Thr Leu Gln Ala Arg
305                 310                 315                 320

Met Ser Cys Glu Gln Lys Ala Glu Gly His Ser Ser Gly Ser Trp Gln
                325                 330                 335

Phe Ser Phe Asp Gly Gln Ile Phe Leu Leu Phe Asp Ser Glu Lys Arg
            340                 345                 350

Met Trp Thr Thr Val His Pro Gly Ala Arg Lys Met Lys Glu Lys Trp
        355                 360                 365

Glu Asn Asp Lys Val Val Ala Thr Ile Leu Trp Gln Thr Ser Met Gly
    370                 375                 380

Asp Cys Ile Gly Trp Leu Glu Asp Phe Leu Met Gly Met Asp Ser Thr
385                 390                 395                 400

Leu Glu Pro Ser

<210> SEQ ID NO 120
<211> LENGTH: 1212
<212> TYPE: DNA
<213> ORGANISM: Artificial sequence
<220> FEATURE:
<223> OTHER INFORMATION: Synthetic polynucleotide, encoding rituximab
      LC_ULBP2.C

<400> SEQUENCE: 120

```
cagatcgtgt tgtcccaatc acccgcaatt ctctctgcga gcccagggga gaaggtgacc      60
atgacttgcc gcgcttcaag ttccgtatcc tacattcact ggttccagca gaagcccgga     120
agttccccta agccctggat ctatgctaca tccaatctgg caagcggtgt tcccgttaga     180
ttttccggaa gcgggtctgg aaccagttac agtctgacta tttccagggt cgaggccgaa     240
gatgcggcta cttattattg ccaacagtgg acctctaacc cacccacatt cggcggcggc     300
actaagttgg aaattaagcg gaccgtggcc gccccgagcg tgttcatttt ccctcccctcc    360
gacgagcagt tgaaatcggg caccgctagc gtggtctgcc ttctcaacaa tttctatcca    420
cgggaagcca aagtgcagtg gaaggtcgac aacgcgctcc aatccgggaa ctcacaggaa    480
tccgtgactg agcaggattc caaggactcg acctactccc tgtcatccac gctgaccctg    540
agcaaggcag actacgagaa gcacaaggtc tacgcctgcg aagtgacaca ccagggactg    600
tccagcccg tgaccaagag cttcaacaga ggagaatgcg cacctacctc aagctctgga    660
ggaggtggca gcgagccca gtctctgagc tacgacatca cagttattcc caagttcagg    720
```

```
cccggaccgc gctggtgtgc cgtgcaagga caagtcgacg aaaaaaccctt tcttcattac    780
gattgcggaa ataagactgt aacgccagtc tctcctttag gtaagaagtt aaacgtcact    840
acggcgtgga aggcacaaaa ccccgtcctg cgcgaggtcg tcgacatcct gactgaacaa    900
ttgtgggaca tccagctcga gaattacact ccaaaggagc ctcttaccct gcaggctaga    960
atgtcttgcg agcaaaaggc agagggccac tcctccggca gctggcagtt cagtttcgac   1020
ggacaaatct ttctgttatt cgattcagag aagagaatgt ggactacagt tcaccccggt   1080
gcccgtaaaa tgaaggagaa gtgggaaaac gacaaagtgg tggcgactat tctgtggcag   1140
acttcgatgg gagactgcat cggttggctg gaagatttcc tcatgggtat ggactccact   1200
ttggagccat cg                                                        1212
```

<210> SEQ ID NO 121
<211> LENGTH: 404
<212> TYPE: PRT
<213> ORGANISM: Artificial sequence
<220> FEATURE:
<223> OTHER INFORMATION: Synthetic peptide rituximab LC_ULBP2.R

<400> SEQUENCE: 121

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Ala Pro Thr Ser Ser Ser Gly Gly Gly Gly Ser
    210                 215                 220

Glu Pro His Ser Leu Ser Tyr Asp Ile Thr Val Ile Pro Lys Phe Arg
225                 230                 235                 240

Pro Gly Pro Arg Trp Cys Ala Val Gln Gly Gln Val Asp Glu Lys Thr
                245                 250                 255

Phe Leu His Tyr Asp Cys Gly Asn Lys Thr Val Thr Pro Val Ser Pro
            260                 265                 270
```

Leu Gly Lys Lys Leu Asn Val Thr Thr Ala Trp Lys Ala Gln Asn Pro
            275                 280                 285

Val Leu Arg Glu Val Val Asp Ile Leu Thr Glu Gln Leu Trp Asp Ile
        290                 295                 300

Gln Leu Glu Asn Tyr Thr Pro Lys Glu Pro Leu Thr Leu Gln Ala Arg
305                 310                 315                 320

Met Ser Cys Glu Gln Lys Ala Glu Gly His Ser Ser Gly Ser Trp Gln
                325                 330                 335

Phe Ser Phe Asp Gly Gln Ile Phe Leu Leu Phe Asp Ser Glu Lys Arg
            340                 345                 350

Met Trp Thr Thr Val His Pro Gly Ala Arg Lys Met Lys Glu Lys Trp
        355                 360                 365

Glu Asn Asp Lys Val Val Ala Thr Leu Leu Trp Gly Trp Ser Met Gly
370                 375                 380

Asp Cys Ile Gly Trp Leu Glu Asp Phe Leu Met Gly Met Asp Ser Thr
385                 390                 395                 400

Leu Glu Pro Ser

<210> SEQ ID NO 122
<211> LENGTH: 1212
<212> TYPE: DNA
<213> ORGANISM: Artificial sequence
<220> FEATURE:
<223> OTHER INFORMATION: Synthetic polynucleotide, encoding rituximab
      LC_ULBP2.R

<400> SEQUENCE: 122
cagatcgtgt tgtcccaatc acccgcaatt ctctctgcga gcccagggga gaaggtgacc        60
atgacttgcc gcgcttcaag ttccgtatcc tacattcact ggttccagca gaagcccgga       120
agttccccta agccctggat ctatgctaca tccaatctgg caagcggtgt tcccgttaga       180
ttttccggaa gcgggtctgg aaccagttac agtctgacta tttccagggt cgaggccgaa       240
gatgcggcta cttattattg ccaacagtgg acctctaacc cacccacatt cggcggcggc       300
actaagttgg aaattaagcg gaccgtggcc gccccgagcg tgttcatttt ccctcccctc       360
gacgagcagt tgaaatcggg caccgctagc gtggtctgcc ttctcaacaa tttctatcca       420
cgggaagcca agtgcagtg gaaggtcgac aacgcgctcc aatccgggaa ctcacaggaa       480
tccgtgactg agcaggattc caaggactcg acctactccc tgtcatccac gctgaccctg       540
agcaaggcag actacgagaa gcacaaggtc tacgcctgcg aagtgacaca ccagggactg       600
tccagccccg tgaccaagag cttcaacaga ggagaatgcg cacctacctc aagctctgga       660
ggaggtggca gcgagcccca tagtctgagc tacgacatca cagttattcc caagttcagg       720
cccggaccgc gctggtgtgc cgtgcaagga caagtcgacg aaaaaacctt tcttcattac       780
gattgcggaa ataagactgt aacgccagtc tctcctttag gtaagaagtt aaacgtcact       840
acggcgtgga aggcacaaaa ccccgtcctg cgcgaggtcg tcgacatcct gactgaacaa       900
ttgtgggaca tccagctcga gaattacact ccaaaggagc ctcttaccct gcaggctaga       960
atgtcttgcg agcaaaaggc agagggccac tcctccggca gctggcagtt cagtttcgac      1020
ggacaaatct ttctgttatt cgattcagag aagagaatgt ggactacagt tcaccccggt      1080
gcccgtaaaa tgaaggagaa gtgggaaaac gacaaagtgg tggcgacttt gttgtgggg       1140 tggtcgatgg gagactgcat cggttggctg gaagatttcc tcatgggtat ggactccact      1200
ttggagccat cg                                                          1212

<210> SEQ ID NO 123
<211> LENGTH: 404
<212> TYPE: PRT
<213> ORGANISM: Artificial sequence
<220> FEATURE:
<223> OTHER INFORMATION: Synthetic peptide rituximab LC_ULBP2.AA

<400> SEQUENCE: 123

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Ala Pro Thr Ser Ser Ser Gly Gly Gly Gly Ser
    210                 215                 220

Glu Pro His Ser Leu Ser Tyr Asp Ile Thr Val Ile Pro Lys Phe Arg
225                 230                 235                 240

Pro Gly Pro Arg Trp Cys Ala Val Gln Gly Gln Val Asp Glu Lys Thr
                245                 250                 255

Phe Leu His Tyr Asp Cys Gly Asn Lys Thr Val Thr Pro Val Ser Pro
            260                 265                 270

Leu Gly Lys Lys Leu Asn Val Thr Thr Ala Trp Lys Ala Gln Asn Pro
        275                 280                 285

Val Leu Arg Glu Val Val Asp Ile Leu Thr Glu Gln Leu Trp Asp Ile
    290                 295                 300

Gln Leu Glu Asn Tyr Thr Pro Lys Glu Pro Leu Thr Leu Gln Ala Arg
305                 310                 315                 320

Met Ser Cys Glu Gln Lys Ala Glu Gly His Ser Ser Gly Ser Trp Gln
                325                 330                 335

Phe Ser Phe Asp Gly Gln Ile Phe Leu Leu Phe Asp Ser Glu Lys Arg
            340                 345                 350

Met Trp Thr Thr Val His Pro Gly Ala Arg Lys Met Lys Glu Lys Trp
        355                 360                 365

Glu Asn Asp Lys Val Val Ala Thr Met Phe Trp Ser Trp Ser Met Gly
370                 375                 380

Asp Cys Ile Gly Trp Leu Glu Asp Phe Leu Met Gly Met Asp Ser Thr
385                 390                 395                 400

Leu Glu Pro Ser

<210> SEQ ID NO 124
<211> LENGTH: 1212
<212> TYPE: DNA
<213> ORGANISM: Artificial sequence
<220> FEATURE:
<223> OTHER INFORMATION: Synthetic polynucleotide, encoding rituximab
      LC_ULBP2.AA

<400> SEQUENCE: 124

| | | | | | |
|---|---|---|---|---|---|
| cagatcgtgt | tgtcccaatc | acccgcaatt | ctctctgcga | gcccagggga | gaaggtgacc | 60 |
| atgacttgcc | gcgcttcaag | ttccgtatcc | tacattcact | ggttccagca | gaagcccgga | 120 |
| agttccccta | agccctggat | ctatgctaca | tccaatctgg | caagcggtgt | tcccgttaga | 180 |
| ttttccggaa | gcgggtctgg | aaccagttac | agtctgacta | tttccagggt | cgaggccgaa | 240 |
| gatgcggcta | cttattattg | ccaacagtgg | acctctaacc | cacccacatt | cggcggcggc | 300 |
| actaagttgg | aaattaagcg | gaccgtggcc | gccccgagcg | tgttcatttt | ccctcccctcc | 360 |
| gacgagcagt | tgaaatcggg | caccgctagc | gtggtctgcc | ttctcaacaa | tttctatcca | 420 |
| cgggaagcca | aagtgcagtg | gaaggtcgac | aacgcgctcc | aatccgggaa | ctcacaggaa | 480 |
| tccgtgactg | agcaggattc | caaggactcg | acctactccc | tgtcatccac | gctgaccctg | 540 |
| agcaaggcag | actacgagaa | gcacaaggtc | tacgcctgcg | aagtgacaca | ccagggactg | 600 |
| tccagccccg | tgaccaagag | cttcaacaga | ggagaatgcg | cacctacctc | aagctctgga | 660 |
| ggaggtggca | gcgagcccca | tagtctgagc | tacgacatca | cagttattcc | caagttcagg | 720 |
| cccggaccgc | gctggtgtgc | cgtgcaagga | caagtcgacg | aaaaaacctt | tcttcattac | 780 |
| gattgcggaa | ataagactgt | aacgccagtc | tctcctttag | gtaagaagtt | aaacgtcact | 840 |
| acggcgtgga | aggcacaaaa | ccccgtcctg | cgcgaggtcg | tcgacatcct | gactgaacaa | 900 |
| ttgtgggaca | tccagctcga | gaattacact | ccaaaggagc | tcttaccct | gcaggctaga | 960 |
| atgtcttgcg | agcaaaaggc | agagggccac | tcctccggca | gctggcagtt | cagtttcgac | 1020 |
| ggacaaatct | ttctgttatt | cgattcagag | aagagaatgt | ggactacagt | tcaccccggt | 1080 |
| gcccgtaaaa | tgaaggagaa | gtgggaaaac | gacaaagtgg | tggcgactat | gttttggagt | 1140 |
| tggtcgatgg | gagactgcat | cggttggctg | gaagatttcc | tcatgggtat | ggactccact | 1200 |
| ttggagccat | cg | | | | | 1212 |

<210> SEQ ID NO 125
<211> LENGTH: 404
<212> TYPE: PRT
<213> ORGANISM: Artificial sequence
<220> FEATURE:
<223> OTHER INFORMATION: Synthetic peptide rituximab LC_ULBP2.AB

<400> SEQUENCE: 125

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
 65              70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Ala Pro Thr Ser Ser Gly Gly Gly Gly Ser
210                 215                 220

Glu Pro His Ser Leu Ser Tyr Asp Ile Thr Val Ile Pro Lys Phe Arg
225                 230                 235                 240

Pro Gly Pro Arg Trp Cys Ala Val Gln Gly Gln Val Asp Glu Lys Thr
                245                 250                 255

Phe Leu His Tyr Asp Cys Gly Asn Lys Thr Val Thr Pro Val Ser Pro
            260                 265                 270

Leu Gly Lys Lys Leu Asn Val Thr Thr Ala Trp Lys Ala Gln Asn Pro
        275                 280                 285

Val Leu Arg Glu Val Val Asp Ile Leu Thr Glu Gln Leu Trp Asp Ile
290                 295                 300

Gln Leu Glu Asn Tyr Thr Pro Lys Glu Pro Leu Thr Leu Gln Ala Arg
305                 310                 315                 320

Met Ser Cys Glu Gln Lys Ala Glu Gly His Ser Ser Gly Ser Trp Gln
                325                 330                 335

Phe Ser Phe Asp Gly Gln Ile Phe Leu Leu Phe Asp Ser Glu Lys Arg
            340                 345                 350

Met Trp Thr Thr Val His Pro Gly Ala Arg Lys Met Lys Glu Lys Trp
        355                 360                 365

Glu Asn Asp Lys Val Val Ala Thr Leu Met Trp Gln Trp Ser Met Gly
370                 375                 380

Asp Cys Ile Gly Trp Leu Glu Asp Phe Leu Met Gly Met Asp Ser Thr
385                 390                 395                 400

Leu Glu Pro Ser

<210> SEQ ID NO 126
<211> LENGTH: 1212
<212> TYPE: DNA
<213> ORGANISM: Artificial sequence
<220> FEATURE:
<223> OTHER INFORMATION: Synthetic polynucleotide, encoding rituximab
      LC_ULBP2.AB

<400> SEQUENCE: 126

```
cagatcgtgt tgtcccaatc acccgcaatt ctctctgcga gcccagggga gaaggtgacc      60
atgacttgcc gcgcttcaag ttccgtatcc tacattcact ggttccagca gaagcccgga     120
agttccccta agccctggat ctatgctaca tccaatctgg caagcggtgt tcccgttaga     180
ttttccggaa gcgggtctgg aaccagttac agtctgacta tttccagggt cgaggccgaa     240
gatgcggcta cttattattg ccaacagtgg acctctaacc cacccacatt cggcggcggc     300
actaagttgg aaattaagcg gaccgtggcc gccccgagcg tgttcatttt ccctccctcc     360
gacgagcagt tgaaatcggg caccgctagc gtggtctgcc ttctcaacaa tttctatcca     420
cgggaagcca agtgcagtg gaaggtcgac aacgcgctcc aatccgggaa ctcacaggaa     480
tccgtgactg agcaggattc caaggactcg acctactccc tgtcatccac gctgaccctg     540
agcaaggcag actacgagaa gcacaaggtc tacgcctgcg aagtgacaca ccagggactg     600
tccagccccg tgaccaagag cttcaacaga ggagaatgcg cacctacctc aagctctgga     660
ggaggtggca gcgagcccca tagtctgagc tacgacatca cagttattcc caagttcagg     720
cccggaccgc gctggtgtgc cgtgcaagga caagtcgacg aaaaaacctt tcttcattac     780
gattgcggaa ataagactgt aacgccagtc tctcctttag gtaagaagtt aaacgtcact     840
acggcgtgga aggcacaaaa ccccgtcctg cgcgaggtcg tcgacatcct gactgaacaa     900
ttgtgggaca tccagctcga gaattacact ccaaaggagc tcttaccct gcaggctaga      960
atgtcttgcg agcaaaaggc agagggccac tcctccggca gctggcagtt cagtttcgac    1020
ggacaaatct ttctgttatt cgattcagag aagagaatgt ggactacagt tcaccccggt    1080
gcccgtaaaa tgaaggagaa gtgggaaaac gacaaagtgg tggcgactct tatgtggcag    1140
tggtcgatgg gagactgcat cggttggctg gaagatttcc tcatgggtat ggactccact    1200
ttggagccat cg                                                        1212
```

<210> SEQ ID NO 127
<211> LENGTH: 180
<212> TYPE: PRT
<213> ORGANISM: Artificial sequence
<220> FEATURE:
<223> OTHER INFORMATION: Synthetic peptide, ULBP2 alpha1-alpha2 variant
      ULBP2.S3

<400> SEQUENCE: 127

```
Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
```

```
                130                 135                 140
Glu Asn Asp Lys Val Val Ala Thr Lys Leu Tyr Leu Trp Ser Met Gly
145                 150                 155                 160

Asp Cys Ile Gly Trp Leu Glu Asp Phe Leu Met Gly Met Asp Ser Thr
                165                 170                 175

Leu Glu Pro Ser
            180

<210> SEQ ID NO 128
<211> LENGTH: 540
<212> TYPE: DNA
<213> ORGANISM: Artificial sequence
<220> FEATURE:
<223> OTHER INFORMATION: Synthetic polynucleotide, encoding ULBP2
      alpha1-alpha2 variant ULBP2.S3

<400> SEQUENCE: 128
gagccccata gtctgagcta cgacatcaca gttattccca gttcaggcc cggaccgcgc      60 tggtgtgccg tgcaaggaca gtcgacgaa aaaacctttc ttcattacga ttgcggaaat     120
aagactgtaa cgccagtctc tcctttaggt aagaagttaa acgtcactac ggcgtggaag    180
gcacaaaacc ccgtcctgcg cgaggtcgtc gacatcctga ctgaacaatt gtgggacatc    240
cagctcgaga attacactcc aaaggagcct cttaccctgc aggctagaat gtcttgcgag    300
caaaaggcag agggccactc ctccggcagc tggcagttca gtttcgacgg acaaatcttt    360
ctgttattcg attcagagaa gagaatgtgg actacagttc accccggtgc ccgtaaaatg    420
aaggagaagt gggaaaacga caaagtggtg gcgactaagc tttatctttg gtcgatggga    480
gactgcatcg gttggctgga agatttcctc atgggtatgg actccacttt ggagccatcg    540

<210> SEQ ID NO 129
<211> LENGTH: 404
<212> TYPE: PRT
<213> ORGANISM: Artificial sequence
<220> FEATURE:
<223> OTHER INFORMATION: Synthetic peptide rituximab LC_ULBP2.S3

<400> SEQUENCE: 129

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160
```

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Ala Pro Thr Ser Ser Gly Gly Gly Gly Ser
    210                 215                 220

Glu Pro His Ser Leu Ser Tyr Asp Ile Thr Val Ile Pro Lys Phe Arg
225                 230                 235                 240

Pro Gly Pro Arg Trp Cys Ala Val Gln Gly Gln Val Asp Glu Lys Thr
                245                 250                 255

Phe Leu His Tyr Asp Cys Gly Asn Lys Thr Val Thr Pro Val Ser Pro
            260                 265                 270

Leu Gly Lys Lys Leu Asn Val Thr Thr Ala Trp Lys Ala Gln Asn Pro
        275                 280                 285

Val Leu Arg Glu Val Val Asp Ile Leu Thr Glu Gln Leu Trp Asp Ile
290                 295                 300

Gln Leu Glu Asn Tyr Thr Pro Lys Glu Pro Leu Thr Leu Gln Ala Arg
305                 310                 315                 320

Met Ser Cys Glu Gln Lys Ala Glu Gly His Ser Ser Gly Ser Trp Gln
                325                 330                 335

Phe Ser Phe Asp Gly Gln Ile Phe Leu Leu Phe Asp Ser Glu Lys Arg
            340                 345                 350

Met Trp Thr Thr Val His Pro Gly Ala Arg Lys Met Lys Glu Lys Trp
        355                 360                 365

Glu Asn Asp Lys Val Val Ala Thr Lys Leu Tyr Leu Trp Ser Met Gly
370                 375                 380

Asp Cys Ile Gly Trp Leu Glu Asp Phe Leu Met Gly Met Asp Ser Thr
385                 390                 395                 400

Leu Glu Pro Ser

<210> SEQ ID NO 130
<211> LENGTH: 1212
<212> TYPE: DNA
<213> ORGANISM: Artificial sequence
<220> FEATURE:
<223> OTHER INFORMATION: Synthetic polynucleotide, encoding rituximab
      LC_ULBP2.S3

<400> SEQUENCE: 130
cagatcgtgt tgtcccaatc acccgcaatt ctctctgcga gcccagggga gaaggtgacc      60
atgacttgcc gcgcttcaag ttccgtatcc tacattcact ggttccagca gaagcccgga     120
agttccccta agccctggat ctatgctaca tccaatctgg caagcggtgt tcccgttaga     180
ttttccggaa gcgggtctgg aaccagttac agtctgacta tttccagggt cgaggccgaa     240
gatgcggcta cttattattg ccaacagtgg acctctaacc cacccacatt cggcggcggc     300
actaagttgg aaattaagcg gaccgtggcc gccccgagcg tgttcatttt ccctcccctcc    360 gacgagcagt tgaaatcggg caccgctagc gtggtctgcc ttctcaacaa tttctatcca     420
cgggaagcca agtgcagtg gaaggtcgac aacgcgctcc aatccgggaa ctcacaggaa      480
tccgtgactg agcaggattc caaggactcg acctactccc tgtcatccac gctgaccctg     540
agcaaggcag actacgagaa gcacaaggtc tacgcctgcg aagtgacaca ccagggactg     600

```
tccagccccg tgaccaagag cttcaacaga ggagaatgcg cacctacctc aagctctgga    660
ggaggtggca gcgagcccca tagtctgagc tacgacatca cagttattcc caagttcagg    720
cccggaccgc gctggtgtgc cgtgcaagga caagtcgacg aaaaaacctt tcttcattac    780
gattgcggaa ataagactgt aacgccagtc tctcctttag gtaagaagtt aaacgtcact    840
acggcgtgga aggcacaaaa ccccgtcctg cgcgaggtcg tcgacatcct gactgaacaa    900
ttgtgggaca tccagctcga gaattacact ccaaaggagc ctcttaccct gcaggctaga    960
atgtcttgcg agcaaaaggc agagggccac tcctccggca gctggcagtt cagtttcgac   1020
ggacaaatct ttctgttatt cgattcagag aagagaatgt ggactacagt tcaccccggt   1080
gcccgtaaaa tgaaggagaa gtgggaaaac gacaaagtgg tggcgactaa gctttatctt   1140
tggtcgatgg gagactgcat cggttggctg gaagatttcc tcatgggtat ggactccact   1200
ttggagccat cg                                                       1212
```

<210> SEQ ID NO 131
<211> LENGTH: 634
<212> TYPE: PRT
<213> ORGANISM: Artificial sequence
<220> FEATURE:
<223> OTHER INFORMATION: Synthetic peptide rituximab HC_ULBP2.R80W

<400> SEQUENCE: 131

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Ala Val Ser His
        260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Ala Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Gly Gly Gly Ser Glu Pro His Ser Leu Ser Tyr Asp Ile Thr
450                 455                 460

Val Ile Pro Lys Phe Arg Pro Gly Pro Arg Trp Cys Ala Val Gln Gly
465                 470                 475                 480

Gln Val Asp Glu Lys Thr Phe Leu His Tyr Asp Cys Gly Asn Lys Thr
                485                 490                 495

Val Thr Pro Val Ser Pro Leu Gly Lys Lys Leu Asn Val Thr Thr Ala
                500                 505                 510

Trp Lys Ala Gln Asn Pro Val Leu Arg Glu Val Val Asp Ile Leu Thr
        515                 520                 525

Glu Gln Leu Trp Asp Ile Gln Leu Glu Asn Tyr Thr Pro Lys Glu Pro
530                 535                 540

Leu Thr Leu Gln Ala Arg Met Ser Cys Glu Gln Lys Ala Glu Gly His
545                 550                 555                 560

Ser Ser Gly Ser Trp Gln Phe Ser Phe Asp Gly Gln Ile Phe Leu Leu
                565                 570                 575

Phe Asp Ser Glu Lys Arg Met Trp Thr Thr Val His Pro Gly Ala Arg
                580                 585                 590

Lys Met Lys Glu Lys Trp Glu Asn Asp Lys Val Val Ala Met Ser Phe
                595                 600                 605

His Tyr Phe Ser Met Gly Asp Cys Ile Gly Trp Leu Glu Asp Phe Leu
        610                 615                 620

Met Gly Met Asp Ser Thr Leu Glu Pro Ser
625                 630

<210> SEQ ID NO 132
<211> LENGTH: 1902
<212> TYPE: DNA
<213> ORGANISM: Artificial sequence
<220> FEATURE:
```

<223> OTHER INFORMATION: Synthetic polynucleotide, encoding rituximab
      HC_ULBP2.R80W

<400> SEQUENCE: 132

```
caagttcagc ttcagcagcc gggggctgag ttggtgaaac ccggggccag tgtgaagatg      60
agctgtaaag cgagcggcta caccttcact tcttataata tgcattgggt taagcaaacg     120
ccaggaaggg ggctggagtg gatcggcgct atttacccag gtaacggtga cacatcatat     180
aaccaaaagt ttaagggaaa ggcaaccctc acagcggaca gagtagctca accgcatac     240
atgcaactgt caagccttac ctccgaagac agcgcagtgt actactgcgc cagaagcacc     300
tactatgggg gtgattggta cttcaacgtc tgggggggctg gcaccacagt gactgtaagc    360
gcagcgtcga ccaagggccc gtcagtgttc ccgctggccc cgtcatccaa gtccacgtct     420
gggggcacag cagccctggg atgcttggtc aaggactact cccccgagcc cgtgactgtg     480
tcctggaact ccggagcact gacctccgga gtgcacacct tcccgcggt gctgcagtcc      540
tccggactgt actccctgtc gtcggtcgtg accgtgccga gctcctcgct cggaacccag     600
acctacatct gcaacgtgaa ccacaagccc tcgaacacca agtggacaa gaaggtcgag      660
cccaaaagct gcgacaagac tcacacttgt ccgccgtgcc cgcccccga actgctgggt     720
ggcccctccg tgttcctgtt cccgcctaag cctaaggaca cccttatgat cagccgcacc     780
cctgaagtga cctgtgtcgt cgtggcagtg tcacacgagg acccggaggt caagttcaat     840
tggtacgtgg acggcgtgga agtgcataac gcaaagacca gcctcggga ggaacagtac      900
gcctcgacct accgcgtggt gtcagtcctg actgtgctgc accaggactg gctgaacggg    960
aaggagtaca agtgcaaagt gtcgaacaag gccctgccgg ctccaattga aaagaccatc   1020
agcaaggcca agggccagcc aagggaacca caggtgtaca ccctcccctcc ttcccgggac   1080
gagctgacca aaaaccaagt gtccctgact tgccttgtga aggggttcta cccttctgac   1140
attgccgtcg aatgggaatc gaacggacag cctgaaaaca actataagac taccccgccc   1200
gtgctggatt ccgacggaag cttcttcctg tactccaagc tgaccgtgga caagtcgaga   1260
tggcagcagg gaaatgtgtt cagctgctcc gtgatgcatg aggcgctgca caaccactac   1320
acccagaagt cactgagcct ctcccccgga ggaggtggca gcgagcccca tagtctgagc   1380
tacgacatca cagttattcc caagttcagg cccggaccgc gctggtgtgc cgtgcaagga   1440
caagtcgacg aaaaaacctt tcttcattac gattgcggaa ataagactgt aacgccagtc   1500
tctcctttag gtaagaagtt aaacgtcact acggcgtgga aggcacaaaa ccccgtcctg   1560
cgcgaggtcg tcgacatcct gactgaacaa ttgtgggaca tccagctcga gaattacact   1620
ccaaaggagc ctcttaccct gcaggctaga atgtcttgcg agcaaaaggc agagggccac   1680
tcctccggca gctggcagtt cagtttcgac ggacaaatct ttctgttatt cgattcagag   1740
aagagaatgt ggactacagt tcaccccggt gcccgtaaaa tgaaggagaa gtgggaaaac   1800
gacaaagtgg tggcgatgtc attccactat ttctcgatgg gagactgcat cggttggctg   1860
gaagatttcc tcatgggtat ggactccact ttggagccat cg                       1902
```

<210> SEQ ID NO 133
<211> LENGTH: 405
<212> TYPE: PRT
<213> ORGANISM: Artificial sequence
<220> FEATURE:
<223> OTHER INFORMATION: Synthetic peptide trastuzumab LC_ULBP2.R

<400> SEQUENCE: 133

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65              70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ala Pro Thr Ser Ser Gly Gly Gly Gly
    210                 215                 220

Ser Glu Pro His Ser Leu Ser Tyr Asp Ile Thr Val Ile Pro Lys Phe
225                 230                 235                 240

Arg Pro Gly Pro Arg Trp Cys Ala Val Gln Gly Gln Val Asp Glu Lys
                245                 250                 255

Thr Phe Leu His Tyr Asp Cys Gly Asn Lys Thr Val Thr Pro Val Ser
            260                 265                 270

Pro Leu Gly Lys Lys Leu Asn Val Thr Thr Ala Trp Lys Ala Gln Asn
    275                 280                 285

Pro Val Leu Arg Glu Val Val Asp Ile Leu Thr Glu Gln Leu Trp Asp
            290                 295                 300

Ile Gln Leu Glu Asn Tyr Thr Pro Lys Glu Pro Leu Thr Leu Gln Ala
305                 310                 315                 320

Arg Met Ser Cys Glu Gln Lys Ala Glu Gly His Ser Ser Gly Ser Trp
                325                 330                 335

Gln Phe Ser Phe Asp Gly Gln Ile Phe Leu Leu Phe Asp Ser Glu Lys
            340                 345                 350

Arg Met Trp Thr Thr Val His Pro Gly Ala Arg Lys Met Lys Glu Lys
        355                 360                 365

Trp Glu Asn Asp Lys Val Val Ala Thr Leu Leu Trp Gly Trp Ser Met
    370                 375                 380

Gly Asp Cys Ile Gly Trp Leu Glu Asp Phe Leu Met Gly Met Asp Ser
385                 390                 395                 400

Thr Leu Glu Pro Ser
            405
```

<210> SEQ ID NO 134
<211> LENGTH: 1215
<212> TYPE: DNA
<213> ORGANISM: Artificial sequence
<220> FEATURE:
<223> OTHER INFORMATION: Synthetic polynucleotide, encoding trastuzumab LC_ULBP2.R

<400> SEQUENCE: 134

```
gatatccaaa tgactcaatc accatcttca ctctccgcga gcgtgggtga tcgggtcacc      60
atcacatgta gggcgagcca agatgtgaat accgccgtcg cgtggtatca acaaaagccg     120
ggaaaagcac caaaactgct tatatactct gcatccttcc tgtactctgg ggtgccaagc     180
cggttctccg gtagtagatc tggtactgac tttacactca ctatcagcag tctgcaacct     240
gaggactttg cgacatacta ttgccagcag cactacacaa ccccacctac atttggtcag     300
gggacaaagg tggagatcaa gcggaccgtg gccgccccga gcgtgttcat tttccctccc     360
tccgacgagc agttgaaatc gggcaccgct agcgtggtct gccttctcaa caatttctat     420
ccacgggaag ccaaagtgca gtggaaggtc gacaacgcgc tccaatccgg gaactcacag     480
gaatccgtga ctgagcagga ttccaaggac tcgacctact ccctgtcatc cacgctgacc     540
ctgagcaagg cagactacga aagcacaag gtctacgcct gcgaagtgac acaccaggga     600
ctgtccagcc ccgtgaccaa gagcttcaac agaggagaat gcgcacctac ctcaagctct     660
ggaggaggtg gcagcgagcc ccatagtctg agctacgaca tcacagttat tcccaagttc     720
aggcccggac cgcgctggtg tgccgtgcaa ggacaagtcg acgaaaaaac ctttcttcat     780
tacgattgcg gaaataagac tgtaacgcca gtctctcctt taggtaagaa gttaaacgtc     840
actacggcgt ggaaggcaca aaaccccgtc ctgcgcgagg tcgtcgacat cctgactgaa     900
caattgtggg acatccagct cgagaattac actccaaagg agcctcttac cctgcaggct     960
agaatgtctt gcgagcaaaa ggcagagggc cactcctccg gcagctggca gttcagtttc    1020
gacggacaaa tctttctgtt attcgattca gagaagagaa tgtggactac agttcacccc    1080
ggtgcccgta aaatgaagga gaagtgggaa acgacaaag tggtggcgac tttgttgtgg    1140
gggtggtcga tgggagactg catcggttgg ctggaagatt tcctcatggg tatggactcc    1200
actttggagc catcg                                                     1215
```

<210> SEQ ID NO 135
<211> LENGTH: 156
<212> TYPE: PRT
<213> ORGANISM: Artificial sequence
<220> FEATURE:
<223> OTHER INFORMATION: Synthetic peptide NKG2D.wt ectodomain

<400> SEQUENCE: 135

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95
```

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val
145                 150                 155

<210> SEQ ID NO 136
<211> LENGTH: 468
<212> TYPE: DNA
<213> ORGANISM: Artificial sequence
<220> FEATURE:
<223> OTHER INFORMATION: Synthetic polynucleotide, encoding NKG2D.wt
      ectodomain

<400> SEQUENCE: 136
atggcattgc ctgttacagc tctgctgctg cccctggctc tgcttctgca tgctgccaga     60
cctctgttca atcaagaggt gcagatccct ctgaccgaga gctactgtgg ccctgtcct    120 aagaactgga tctgctacaa gaacaactgc taccagttct tcgacgagag caagaattgg    180
tacgagagcc aggccagctg catgagccag aatgccagcc tgctgaaggt gtacagcaaa    240
gaggaccagg atctgctgaa gctggtcaag agctaccact ggatgggact cgtgcacatc    300
cctacaaacg gcagctggca gtgggaggac ggctctatcc tgtctcctaa cctgctgacc    360
atcatcgaga tgcagaaggg cgactgcgcc ctgtacgcca gcagctttaa ggctacatc    420 gagaactgca gcaccectaa cacctacate tgtatgcage ggaccgtg               468

<210> SEQ ID NO 137
<211> LENGTH: 156
<212> TYPE: PRT
<213> ORGANISM: Artificial sequence
<220> FEATURE:
<223> OTHER INFORMATION: Synthetic peptide NKG2D.YA ectodomain

<400> SEQUENCE: 137

Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Ala His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val
145                 150                 155

<210> SEQ ID NO 138
<211> LENGTH: 468
<212> TYPE: DNA
<213> ORGANISM: Artificial sequence
<220> FEATURE:
<223> OTHER INFORMATION: Synthetic polynucleotide, encoding NKG2D.YA ectodomain

<400> SEQUENCE: 138

```
atggcattgc ctgttacagc tctgctgctg cccctggctc tgcttctgca tgctgccaga      60
cctctgttca atcaagaggt gcagatccct ctgaccgaga gctactgtgg ccccgtcct     120
aagaactgga tctgctacaa gaacaactgc taccagttct tcgacgagag caagaattgg    180
tacgagagcc aggccagctg catgagccag aatgccagcc tgctgaaggt gtacagcaaa    240
gaggaccagg atctgctgaa gctggtcaag agcgcccact ggatgggact cgtgcacatc    300
cctacaaacg gcagctggca gtgggaggac ggctctatcc tgtctcctaa cctgctgacc    360
atcatcgaga tgcagaaggg cgactgcgcc ctgtacgcca gcagctttaa gggctacatc    420
gagaactgca gcaccccta cacctacatc tgtatgcagc ggaccgtg              468
```

<210> SEQ ID NO 139
<211> LENGTH: 156
<212> TYPE: PRT
<213> ORGANISM: Artificial sequence
<220> FEATURE:
<223> OTHER INFORMATION: Synthetic peptide NKG2D.AF ectodomain

<400> SEQUENCE: 139

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
                20                  25                  30

Glu Ser Tyr Cys Gly Pro Cys Pro Lys Asn Trp Ile Cys Tyr Lys Asn
            35                  40                  45

Asn Cys Tyr Gln Phe Phe Asp Glu Ser Lys Asn Trp Tyr Glu Ser Gln
        50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Ala His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Phe Ile Glu Asn Cys Ser
    130                 135                 140

Thr Pro Asn Thr Tyr Ile Cys Met Gln Arg Thr Val
145                 150                 155
```

<210> SEQ ID NO 140
<211> LENGTH: 468
<212> TYPE: DNA
<213> ORGANISM: Artificial sequence
<220> FEATURE:
<223> OTHER INFORMATION: Synthetic polynucleotide, encoding NKG2D.AF ectodomain

<400> SEQUENCE: 140

```
atggcattgc tgttacagc tctgctgctg cccctggctc tgcttctgca tgctgccaga       60
cctctgttca atcaagaggt gcagatccct ctgaccgaga gctactgtgg cccctgtcct      120
aagaactgga tctgctacaa gaacaactgc taccagttct tcgacgagag caagaattgg      180
tacgagagcc aggccagctg catgagccag aatgccagcc tgctgaaggt gtacagcaaa      240
gaggaccagg atctgctgaa gctggtcaag agcgcccact ggatgggact cgtgcacatc      300
cctacaaacg cagctggca gtgggaggac ggctctatcc tgtctcctaa cctgctgacc       360
atcatcgaga tgcagaaggg cgactgcgcc ctgtacgcca gcagctttaa gggcttcatc      420
gagaactgca gcacccctaa cacctacatc tgtatgcagc ggaccgtg                   468
```

```
<210> SEQ ID NO 141
<211> LENGTH: 69
<212> TYPE: PRT
<213> ORGANISM: Artificial sequence
<220> FEATURE:
<223> OTHER INFORMATION: Synthetic peptide CD8alpha hinge and
      transmembrane domain

<400> SEQUENCE: 141
```

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65
```

```
<210> SEQ ID NO 142
<211> LENGTH: 207
<212> TYPE: DNA
<213> ORGANISM: Artificial sequence
<220> FEATURE:
<223> OTHER INFORMATION: Synthetic polynucleotide, encoding CD8alpha
      hinge and transmembrane domain

<400> SEQUENCE: 142
```

```
accaccacac cagctcctag acctccaact cctgctccta caatcgccag ccagcctctg       60
tctctgaggc cagaagcttg tagacctgct gcaggcggag ccgtgcatac aagaggactg      120
gatttcgcct gcgacatcta catctgggcc cctctggctg gaacatgtgg cgtgctgctg      180
ctgagcctgg tcatcaccct gtactgc                                         207
```

```
<210> SEQ ID NO 143
<211> LENGTH: 42
<212> TYPE: PRT
<213> ORGANISM: Artificial sequence
<220> FEATURE:
<223> OTHER INFORMATION: Synthetic peptide 4-1BB

<400> SEQUENCE: 143
```

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40
```

<210> SEQ ID NO 144
<211> LENGTH: 126
<212> TYPE: DNA
<213> ORGANISM: Artificial sequence
<220> FEATURE:
<223> OTHER INFORMATION: Synthetic polynucleotide, encoding 4-1BB

<400> SEQUENCE: 144

```
aagcggggca gaaagaagct gctgtacatc tttaagcagc ccttcatgcg gcccgtgcag      60
accacacaag aggaagatgg ctgctcctgc agattccccg aggaagaaga aggcggctgc     120
gagctg                                                                126
```

<210> SEQ ID NO 145
<211> LENGTH: 112
<212> TYPE: PRT
<213> ORGANISM: Artificial sequence
<220> FEATURE:
<223> OTHER INFORMATION: Synthetic peptide CD3zeta

<400> SEQUENCE: 145

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110
```

<210> SEQ ID NO 146
<211> LENGTH: 336
<212> TYPE: DNA
<213> ORGANISM: Artificial sequence
<220> FEATURE:
<223> OTHER INFORMATION: Synthetic polynucleotide, encoding CD3zeta

<400> SEQUENCE: 146

```
agagtgaagt tcagccgttc tgccgacgct cccgcctata gcagggaca gaaccagctg       60
tacaacgagc tgaacctggg gagaagagaa gagtacgacg tgctggacaa gcggagaggc     120
agagatcctg agatgggcgg caagcccaga cggaagaatc ctcaagaggg cctgtataat     180
gagctgcaga agacaagat ggccgaggcc tacagcgaga tcggaatgaa gggcgagcgc      240
agaagaggca agggacacga tggactgtac caggggcctga gcaccgccac caaggatacc     300
tatgatgccc tgcacatgca ggccctgcct ccaaga                               336
```

<210> SEQ ID NO 147
<211> LENGTH: 239
<212> TYPE: PRT
<213> ORGANISM: Artificial sequence
<220> FEATURE:
<223> OTHER INFORMATION: Synthetic peptide EGFP

<400> SEQUENCE: 147

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 148
<211> LENGTH: 717
<212> TYPE: DNA
<213> ORGANISM: Artificial sequence
<220> FEATURE:
<223> OTHER INFORMATION: Synthetic polynucleotide, encoding EGFP

<400> SEQUENCE: 148
atggtgtcta aaggcgagga actgttcacc ggcgtggtgc ccattctggt ggaactggac    60
ggggatgtga acggccacaa gtttagcgtt agcggcgaag gcgaagggga tgccacatac   120
ggaaagctga ccctgaagtt catctgcacc accggcaagc tgcctgtgcc ttggcctaca   180
ctggtcacca cactgacata cggcgtgcag tgctttagca gatccccga ccatatgaag    240 cagcacgact tcttcaagtc cgccatgcct gagggctacg tgcaagagcg gaccatcttc   300
tttaaggacg acggcaacta caagaccagg gccgaagtga agtttgaggg cgacaccctg   360
gtcaaccgga tcgagctgaa gggcatcgac ttcaaagagg atggcaacat cctgggccac   420
aagctcgagt acaactacaa cagccacaac gtgtacatca tggccgacaa gcagaagaac   480
ggcatcaagg ccaacttcaa gatccggcac aacatcgagg acggcagcgt tcagctggcc   540
gatcactacc agcagaacac ccctatcgga gatggccctg tgctgctccc cgacaatcac   600
tacctgagca cacagagcgc cctgagcaag gaccccaacg agaagaggga tcacatggtg   660
ctgctggaat ttgtgaccgc cgcaggcatc accctcggca tggacgaact gtacaaa     717

<210> SEQ ID NO 149
<211> LENGTH: 473
<212> TYPE: PRT
<213> ORGANISM: Artificial sequence
<220> FEATURE:
<223> OTHER INFORMATION: Synthetic peptide CD8hingeTM_4-1BB_CD3zeta_EGFP

<400> SEQUENCE: 149

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys Ser Leu Lys Arg Gly Arg Lys Lys Leu Leu Tyr
65                  70                  75                  80

Ile Phe Lys Gln Pro Phe Met Arg Pro Val Gln Thr Thr Gln Glu Glu
                85                  90                  95

Asp Gly Cys Ser Cys Arg Phe Pro Glu Glu Glu Glu Gly Gly Cys Glu
            100                 105                 110

Leu Arg Val Lys Phe Ser Arg Ser Ala Asp Ala Pro Ala Tyr Lys Gln
        115                 120                 125

Gly Gln Asn Gln Leu Tyr Asn Glu Leu Asn Leu Gly Arg Arg Glu Glu
    130                 135                 140

Tyr Asp Val Leu Asp Lys Arg Arg Gly Arg Asp Pro Glu Met Gly Gly
145                 150                 155                 160

Lys Pro Arg Arg Lys Asn Pro Gln Glu Gly Leu Tyr Asn Glu Leu Gln
                165                 170                 175

Lys Asp Lys Met Ala Glu Ala Tyr Ser Glu Ile Gly Met Lys Gly Glu
            180                 185                 190

Arg Arg Arg Gly Lys Gly His Asp Gly Leu Tyr Gln Gly Leu Ser Thr
        195                 200                 205

Ala Thr Lys Asp Thr Tyr Asp Ala Leu His Met Gln Ala Leu Pro Pro
    210                 215                 220

Arg Ser Gly Ser Gly Ser Gly Ser Met Val Ser Lys Gly Glu
225                 230                 235                 240

Glu Leu Phe Thr Gly Val Val Pro Ile Leu Val Glu Leu Asp Gly Asp
                245                 250                 255

Val Asn Gly His Lys Phe Ser Val Ser Gly Glu Gly Glu Gly Asp Ala
            260                 265                 270

Thr Tyr Gly Lys Leu Thr Leu Lys Phe Ile Cys Thr Thr Gly Lys Leu
        275                 280                 285

Pro Val Pro Trp Pro Thr Leu Val Thr Thr Leu Thr Tyr Gly Val Gln
    290                 295                 300

Cys Phe Ser Arg Tyr Pro Asp His Met Lys Gln His Asp Phe Phe Lys
305                 310                 315                 320

Ser Ala Met Pro Glu Gly Tyr Val Gln Glu Arg Thr Ile Phe Phe Lys
                325                 330                 335

Asp Asp Gly Asn Tyr Lys Thr Arg Ala Glu Val Lys Phe Glu Gly Asp
            340                 345                 350

Thr Leu Val Asn Arg Ile Glu Leu Lys Gly Ile Asp Phe Lys Glu Asp
        355                 360                 365
```

Gly Asn Ile Leu Gly His Lys Leu Glu Tyr Asn Tyr Asn Ser His Asn
        370                 375                 380

Val Tyr Ile Met Ala Asp Lys Gln Lys Asn Gly Ile Lys Ala Asn Phe
385                 390                 395                 400

Lys Ile Arg His Asn Ile Glu Asp Gly Ser Val Gln Leu Ala Asp His
                405                 410                 415

Tyr Gln Gln Asn Thr Pro Ile Gly Asp Gly Pro Val Leu Leu Pro Asp
            420                 425                 430

Asn His Tyr Leu Ser Thr Gln Ser Ala Leu Ser Lys Asp Pro Asn Glu
        435                 440                 445

Lys Arg Asp His Met Val Leu Leu Glu Phe Val Thr Ala Ala Gly Ile
    450                 455                 460

Thr Leu Gly Met Asp Glu Leu Tyr Lys
465                 470

<210> SEQ ID NO 150
<211> LENGTH: 1419
<212> TYPE: DNA
<213> ORGANISM: Artificial sequence
<220> FEATURE:
<223> OTHER INFORMATION: Synthetic polynucleotide, encoding
      CD8hingeTM_4-1BB_CD3zeta_EGFP

<400> SEQUENCE: 150

| | |
|---|---|
| accaccacac cagctcctag acctccaact cctgctccta caatcgccag ccagcctctg | 60 |
| tctctgaggc cagaagcttg tagacctgct gcaggcggag ccgtgcatac aagaggactg | 120 |
| gatttcgcct gcgacatcta catctgggcc cctctggctg aacatgtgg cgtgctgctg | 180 |
| ctgagcctgg tcatcaccct gtactgcagc ctgaagcggg gcagaaagaa gctgctgtac | 240 |
| atctttaagc agcccttcat gcggcccgtg cagaccacac aagaggaaga tggctgctcc | 300 |
| tgcagattcc ccgaggaaga agaaggcggc tgcgagctga gagtgaagtt cagccgttct | 360 |
| gccgacgctc ccgcctataa gcagggacag aaccagctgt acaacgagct gaacctgggg | 420 |
| agaagagaag agtacgacgt gctggacaag cggagaggca gagatcctga gatgggcggc | 480 |
| aagcccagac ggaagaatcc tcaagagggc ctgtataatg agctgcagaa agacaagatg | 540 |
| gccgaggcct acagcgagat cggaatgaag ggcgagcgca agaggcaa gggacacgat | 600 |
| ggactgtacc agggcctgag caccgccacc aaggatacct atgatgccct gcacatgcag | 660 |
| gccctgcctc caagatcagg ctctggttct ggcagcggca gcatggtgtc taaaggcgag | 720 |
| gaactgttca ccggcgtggt gcccattctg gtggaactgg acggggatgt gaacggccac | 780 |
| aagtttagcg ttagcggcga aggcgaaggg gatgccacat acggaaagct gaccctgaag | 840 |
| ttcatctgca ccaccggcaa gctgcctgtg ccttggccta cactggtcac cacactgaca | 900 |
| tacggcgtgc agtgctttag cagatacccc gaccatatga gcagcacga cttcttcaag | 960 |
| tccgccatgc ctgagggcta cgtgcaagag cggaccatct tctttaagga cgacggcaac | 1020 |
| tacaagacca gggccgaagt gaagtttgag ggcgacaccc tggtcaaccg gatcgagctg | 1080 |
| aagggcatcg acttcaaaga ggatggcaac atcctgggcc acaagctcga gtacaactac | 1140 |
| aacagccaca cgtgtacat catggccgac aagcagaaga cggcatcaa ggccaacttc | 1200 |
| aagatccggc acaacatcga ggacggcagc gttcagctgg ccgatcacta ccagcagaac | 1260 |
| accctatcg agatggccc tgtgctgctc ccgacaatc actacctgag cacacagagc | 1320 |
| gccctgagca aggaccccaa cgagaagagg gatcacatgg tgctgctgga atttgtgacc | 1380 |

```
gccgcaggca tcaccctcgg catggacgaa ctgtacaaa                              1419
```

<210> SEQ ID NO 151
<211> LENGTH: 629
<212> TYPE: PRT
<213> ORGANISM: Artificial sequence
<220> FEATURE:
<223> OTHER INFORMATION: Synthetic peptide
    NKG2D.wt_CD8hingeTM_4-1BB_CD3zeta_EGFP complete chimeric antigen
    receptor

<400> SEQUENCE: 151

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
    210                 215                 220

Cys Ser Leu Lys Arg Gly Arg Lys Lys Leu Leu Tyr Ile Phe Lys Gln
225                 230                 235                 240

Pro Phe Met Arg Pro Val Gln Thr Thr Gln Glu Glu Asp Gly Cys Ser
                245                 250                 255

Cys Arg Phe Pro Glu Glu Glu Glu Gly Gly Cys Glu Leu Arg Val Lys
            260                 265                 270

Phe Ser Arg Ser Ala Asp Ala Pro Ala Tyr Lys Gln Gly Gln Asn Gln
        275                 280                 285

Leu Tyr Asn Glu Leu Asn Leu Gly Arg Arg Glu Glu Tyr Asp Val Leu
    290                 295                 300

Asp Lys Arg Arg Gly Arg Asp Pro Glu Met Gly Gly Lys Pro Arg Arg
305                 310                 315                 320

Lys Asn Pro Gln Glu Gly Leu Tyr Asn Glu Leu Gln Lys Asp Lys Met
                325                 330                 335

Ala Glu Ala Tyr Ser Glu Ile Gly Met Lys Gly Glu Arg Arg Arg Gly
            340                 345                 350
```

Lys Gly His Asp Gly Leu Tyr Gln Gly Leu Ser Thr Ala Thr Lys Asp
        355                 360                 365

Thr Tyr Asp Ala Leu His Met Gln Ala Leu Pro Pro Arg Ser Gly Ser
370                 375                 380

Gly Ser Gly Ser Gly Ser Met Val Ser Lys Gly Glu Glu Leu Phe Thr
385                 390                 395                 400

Gly Val Val Pro Ile Leu Val Glu Leu Asp Gly Asp Val Asn Gly His
                405                 410                 415

Lys Phe Ser Val Ser Gly Glu Gly Glu Gly Asp Ala Thr Tyr Gly Lys
            420                 425                 430

Leu Thr Leu Lys Phe Ile Cys Thr Thr Gly Lys Leu Pro Val Pro Trp
        435                 440                 445

Pro Thr Leu Val Thr Thr Leu Thr Tyr Gly Val Gln Cys Phe Ser Arg
450                 455                 460

Tyr Pro Asp His Met Lys Gln His Asp Phe Phe Lys Ser Ala Met Pro
465                 470                 475                 480

Glu Gly Tyr Val Gln Glu Arg Thr Ile Phe Phe Lys Asp Asp Gly Asn
                485                 490                 495

Tyr Lys Thr Arg Ala Glu Val Lys Phe Glu Gly Asp Thr Leu Val Asn
            500                 505                 510

Arg Ile Glu Leu Lys Gly Ile Asp Phe Lys Glu Asp Gly Asn Ile Leu
        515                 520                 525

Gly His Lys Leu Glu Tyr Asn Tyr Asn Ser His Asn Val Tyr Ile Met
    530                 535                 540

Ala Asp Lys Gln Lys Asn Gly Ile Lys Ala Asn Phe Lys Ile Arg His
545                 550                 555                 560

Asn Ile Glu Asp Gly Ser Val Gln Leu Ala Asp His Tyr Gln Gln Asn
                565                 570                 575

Thr Pro Ile Gly Asp Gly Pro Val Leu Leu Pro Asp Asn His Tyr Leu
            580                 585                 590

Ser Thr Gln Ser Ala Leu Ser Lys Asp Pro Asn Glu Lys Arg Asp His
        595                 600                 605

Met Val Leu Leu Glu Phe Val Thr Ala Ala Gly Ile Thr Leu Gly Met
    610                 615                 620

Asp Glu Leu Tyr Lys
625

<210> SEQ ID NO 152
<211> LENGTH: 1887
<212> TYPE: DNA
<213> ORGANISM: Artificial sequence
<220> FEATURE:
<223> OTHER INFORMATION: Synthetic polynucleotide, encoding
      NKG2D.wt_CD8hingeTM_4-1BB_CD3zeta_EGFP complete chimeric antigen
      receptor

<400> SEQUENCE: 152
atggcattgc tgttacagc tctgctgctg ccctggctc tgcttctgca tgctgccaga      60
cctctgttca atcaagaggt gcagatccct ctgaccgaga gctactgtgg ccctgtcct   120 aagaactgga tctgctacaa gaacaactgc taccagttct tcgacgagag caagaattgg   180
tacgagagcc aggccagctg catgagccag aatgccagcc tgctgaaggt gtacagcaaa   240
gaggaccagg atctgctgaa gctggtcaag agctaccact ggatgggact cgtgcacatc   300
cctacaaacg gcagctggca gtgggaggac ggctctatcc tgtctcctaa cctgctgacc   360

```
atcatcgaga tgcagaaggg cgactgcgcc ctgtacgcca gcagctttaa gggctacatc    420
gagaactgca gcacccctaa cacctacatc tgtatgcagc ggaccgtgac caccacacca    480
gctcctagac ctccaactcc tgctcctaca atcgccagcc agcctctgtc tctgaggcca    540
gaagcttgta gacctgctgc aggcggagcc gtgcatacaa gaggactgga tttcgcctgc    600
gacatctaca tctgggcccc tctggctgga acatgtggcg tgctgctgct gagcctggtc    660
atcaccctgt actgcagcct gaagcggggc agaaagaagc tgctgtacat ctttaagcag    720
cccttcatgc ggcccgtgca gaccacacaa gaggaagatg gctgctcctg cagattcccc    780
gaggaagaag aaggcggctg cgagctgaga gtgaagttca gccgttctgc cgacgctccc    840
gcctataagc agggacagaa ccagctgtac aacgagctga acctggggag aagagaagag    900
tacgacgtgc tggacaagcg agaggcagaa gatcctgaga tgggcggcaa gcccagacgg    960
aagaatcctc aagagggcct gtataatgag ctgcagaaag acaagatggc cgaggcctac   1020
agcgagatcg gaatgaaggg cgagcgcaga gaggcaagg acacgatgg actgtaccag   1080 ggcctgagca ccgccaccaa ggataccttat gatgccctgc acatgcaggc cctgcctcca   1140
agatcaggct ctggttctgg cagcggcagc atggtgtcta aaggcgagga actgttcacc   1200
ggcgtggtgc ccattctggt ggaactggac ggggatgtga acggccacaa gtttagcgtt   1260
agcggcgaag gcgaagggga tgccacatac ggaaagctga ccctgaagtt catctgcacc   1320
accggcaagc tgcctgtgcc ttggcctaca ctggtcacca cactgacata cggcgtgcag   1380
tgctttagca gataccccga ccatatgaag cagcacgact tcttcaagtc cgccatgcct   1440
gagggctacg tgcaagagcg gaccatcttc tttaaggacg acggcaacta caagaccagg   1500
gccgaagtga agtttgaggg cgacaccctg gtcaaccgga tcgagctgaa gggcatcgac   1560
ttcaaagagg atggcaacat cctgggccac aagctcgagt acaactacaa cagccacaac   1620
gtgtacatca tggccgacaa gcagaagaac ggcatcaagg ccaacttcaa gatccggcac   1680
aacatcgagg acggcagcgt tcagctggcc gatcactacc agcagaacac ccctatcgga   1740
gatggccctg tgctgctccc cgacaatcac tacctgagca cacagagcgc cctgagcaag   1800
gaccccaacg agaagaggga tcacatggtg ctgctggaat ttgtgaccgc cgcaggcatc   1860
accctcggca tggacgaact gtacaaa                                       1887
```

<210> SEQ ID NO 153
<211> LENGTH: 629
<212> TYPE: PRT
<213> ORGANISM: Artificial sequence
<220> FEATURE:
<223> OTHER INFORMATION: Synthetic peptide
      NKG2D.YA_CD8hingeTM_4-1BB_CD3zeta_EGFP complete chimeric antigen
      receptor

<400> SEQUENCE: 153

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80
```

-continued

```
Glu Asp Gln Asp Leu Leu Lys Leu Val Lys Ser Ala His Trp Met Gly
                85                  90                  95
Leu Val His Ile Pro Thr Asn Gly Ser Trp Gln Trp Glu Asp Gly Ser
            100                 105                 110
Ile Leu Ser Pro Asn Leu Leu Thr Ile Ile Glu Met Gln Lys Gly Asp
        115                 120                 125
Cys Ala Leu Tyr Ala Ser Ser Phe Lys Gly Tyr Ile Glu Asn Cys Ser
    130                 135                 140
Thr Pro Asn Thr Tyr Ile Cys Met Gln Arg Thr Val Thr Thr Thr Pro
145                 150                 155                 160
Ala Pro Arg Pro Thr Pro Ala Pro Thr Ile Ala Ser Gln Pro Leu
                165                 170                 175
Ser Leu Arg Pro Glu Ala Cys Arg Pro Ala Ala Gly Gly Ala Val His
            180                 185                 190
Thr Arg Gly Leu Asp Phe Ala Cys Asp Ile Tyr Ile Trp Ala Pro Leu
        195                 200                 205
Ala Gly Thr Cys Gly Val Leu Leu Leu Ser Leu Val Ile Thr Leu Tyr
    210                 215                 220
Cys Ser Leu Lys Arg Gly Arg Lys Lys Leu Leu Tyr Ile Phe Lys Gln
225                 230                 235                 240
Pro Phe Met Arg Pro Val Gln Thr Thr Gln Glu Glu Asp Gly Cys Ser
                245                 250                 255
Cys Arg Phe Pro Glu Glu Glu Gly Gly Cys Glu Leu Arg Val Lys
            260                 265                 270
Phe Ser Arg Ser Ala Asp Ala Pro Ala Tyr Lys Gln Gly Gln Asn Gln
        275                 280                 285
Leu Tyr Asn Glu Leu Asn Leu Gly Arg Arg Glu Glu Tyr Asp Val Leu
    290                 295                 300
Asp Lys Arg Arg Gly Arg Asp Pro Glu Met Gly Gly Lys Pro Arg Arg
305                 310                 315                 320
Lys Asn Pro Gln Glu Gly Leu Tyr Asn Glu Leu Gln Lys Asp Lys Met
                325                 330                 335
Ala Glu Ala Tyr Ser Glu Ile Gly Met Lys Gly Glu Arg Arg Arg Gly
            340                 345                 350
Lys Gly His Asp Gly Leu Tyr Gln Gly Leu Ser Thr Ala Thr Lys Asp
        355                 360                 365
Thr Tyr Asp Ala Leu His Met Gln Ala Leu Pro Pro Arg Ser Gly Ser
    370                 375                 380
Gly Ser Gly Ser Gly Ser Met Val Ser Lys Gly Glu Glu Leu Phe Thr
385                 390                 395                 400
Gly Val Val Pro Ile Leu Val Glu Leu Asp Gly Asp Val Asn Gly His
                405                 410                 415
Lys Phe Ser Val Ser Gly Glu Gly Glu Gly Asp Ala Thr Tyr Gly Lys
            420                 425                 430
Leu Thr Leu Lys Phe Ile Cys Thr Thr Gly Lys Leu Pro Val Pro Trp
        435                 440                 445
Pro Thr Leu Val Thr Thr Leu Thr Tyr Gly Val Gln Cys Phe Ser Arg
    450                 455                 460
Tyr Pro Asp His Met Lys Gln His Asp Phe Phe Lys Ser Ala Met Pro
465                 470                 475                 480
Glu Gly Tyr Val Gln Glu Arg Thr Ile Phe Phe Lys Asp Asp Gly Asn
                485                 490                 495
Tyr Lys Thr Arg Ala Glu Val Lys Phe Glu Gly Asp Thr Leu Val Asn
```

```
               500            505              510
Arg Ile Glu Leu Lys Gly Ile Asp Phe Lys Glu Asp Gly Asn Ile Leu
            515                 520                 525

Gly His Lys Leu Glu Tyr Asn Tyr Asn Ser His Asn Val Tyr Ile Met
        530                 535             540

Ala Asp Lys Gln Lys Asn Gly Ile Lys Ala Asn Phe Lys Ile Arg His
545                 550                 555                 560

Asn Ile Glu Asp Gly Ser Val Gln Leu Ala Asp His Tyr Gln Gln Asn
                565                 570                 575

Thr Pro Ile Gly Asp Gly Pro Val Leu Leu Pro Asp Asn His Tyr Leu
            580                 585                 590

Ser Thr Gln Ser Ala Leu Ser Lys Asp Pro Asn Glu Lys Arg Asp His
        595                 600                 605

Met Val Leu Leu Glu Phe Val Thr Ala Ala Gly Ile Thr Leu Gly Met
    610                 615                 620

Asp Glu Leu Tyr Lys
625

<210> SEQ ID NO 154
<211> LENGTH: 1887
<212> TYPE: DNA
<213> ORGANISM: Artificial sequence
<220> FEATURE:
<223> OTHER INFORMATION: Synthetic polynucleotide, encoding
      NKG2D.YA_CD8hingeTM_4-1BB_CD3zeta_EGFP complete chimeric antigen
      receptor

<400> SEQUENCE: 154
atggcattgc ctgttacagc tctgctgctg ccctggctc tgcttctgca tgctgccaga      60
cctctgttca tcaagaggt gcagatccct ctgaccgaga gctactgtgg ccctgtcct     120 aagaactgga tctgctacaa gaacaactgc taccagttct tcgacgagag caagaattgg    180
tacgagagcc aggccagctg catgagccag aatgccagcc tgctgaaggt gtacagcaaa    240
gaggaccagg atctgctgaa gctggtcaag agcgcccact ggatgggact cgtgcacatc    300
cctacaaacg gcagctggca gtgggaggac ggctctatcc tgtctcctaa cctgctgacc    360
atcatcgaga tgcagaaggg cgactgcgcc ctgtacgcca gcagctttaa gggctacatc    420
gagaactgca gcacccctaa cacctacatc tgtatgcagc ggaccgtgac caccacacca    480
gctcctagac ctccaactcc tgctcctaca atcgccagcc agcctctgtc tctgaggcca    540
gaagcttgta gacctgctgc aggcggagcc gtgcatacaa gaggactgga tttcgcctgc    600
gacatctaca tctgggcccc tctggctgga acatgtggcg tgctgctgct gagcctggtc    660 atcccctgt actgcagcct gaagcggggc agaaagaagc tgctgtacat ctttaagcag    720
cccttcatgc ggcccgtgca gaccacacaa gaggaagatg gctgctcctg cagattcccc    780
gaggaagaag aaggcggctg cgagctgaga gtgaagttca gccgttctgc cgacgctccc    840
gcctataagc agggacagaa ccagctgtac aacgagctga acctggggag aagagaagag    900
tacgacgtgc tggacaagcg cgagaggcaga gatcctgaga tgggcggcaa gcccagacgg    960
aagaatcctc aagagggcct gtataatgag ctgcagaaag acaagatggc cgaggcctac   1020
agcgagatcg gaatgaaggg cgagcgcaga gaggcaagg acacgatgg actgtaccag   1080 ggcctgagca ccgccaccaa ggataccat gatgccctgc acatgcaggc cctgcctcca   1140
agatcaggct ctggttctgg cagcggcagc atggtgtcta aaggcgagga actgttcacc   1200
ggcgtggtgc ccattctggt ggaactggac ggggatgtga acggccacaa gtttagcgtt   1260
```

```
agcggcgaag gcgaagggga tgccacatac ggaaagctga ccctgaagtt catctgcacc    1320
accggcaagc tgcctgtgcc ttggcctaca ctggtcacca cactgacata cggcgtgcag    1380
tgctttagca gatacccega ccatatgaag cagcacgact tcttcaagtc cgccatgcct    1440
gagggctacg tgcaagagcg gaccatcttc tttaaggacg acggcaacta caagaccagg    1500
gccgaagtga agtttgaggg cgacaccctg gtcaaccgga tcgagctgaa gggcatcgac    1560
ttcaaagagg atggcaacat cctgggccac aagctcgagt acaactacaa cagccacaac    1620
gtgtacatca tggccgacaa gcagaagaac ggcatcaagg ccaacttcaa gatccggcac    1680
aacatcgagg acggcagcgt tcagctggcc gatcactacc agcagaacac ccctatcgga    1740
gatggccctg tgctgctccc cgacaatcac tacctgagca cacagagcgc cctgagcaag    1800
gaccccaacg agaagaggga tcacatggtg ctgctggaat tgtgaccgc cgcaggcatc    1860 accctcggca tggacgaact gtacaaa    1887
```

<210> SEQ ID NO 155
<211> LENGTH: 629
<212> TYPE: PRT
<213> ORGANISM: Artificial sequence
<220> FEATURE:
<223> OTHER INFORMATION: Synthetic peptide
      NKG2D.AF_CD8hingeTM_4-1BB_CD3zeta_EGFP complete chimeric antigen
      receptor

<400> SEQUENCE: 155

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Ala His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Phe Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
    210                 215                 220

Cys Ser Leu Lys Arg Gly Arg Lys Lys Leu Leu Tyr Ile Phe Lys Gln
225                 230                 235                 240
```

```
Pro Phe Met Arg Pro Val Gln Thr Thr Gln Glu Asp Gly Cys Ser
            245                 250                 255

Cys Arg Phe Pro Glu Glu Glu Gly Gly Cys Glu Leu Arg Val Lys
            260                 265                 270

Phe Ser Arg Ser Ala Asp Ala Pro Ala Tyr Lys Gln Gly Gln Asn Gln
            275                 280                 285

Leu Tyr Asn Glu Leu Asn Leu Gly Arg Arg Glu Glu Tyr Asp Val Leu
            290                 295                 300

Asp Lys Arg Arg Gly Arg Asp Pro Glu Met Gly Gly Lys Pro Arg Arg
305                 310                 315                 320

Lys Asn Pro Gln Glu Gly Leu Tyr Asn Glu Leu Gln Lys Asp Lys Met
                325                 330                 335

Ala Glu Ala Tyr Ser Glu Ile Gly Met Lys Gly Glu Arg Arg Arg Gly
            340                 345                 350

Lys Gly His Asp Gly Leu Tyr Gln Gly Leu Ser Thr Ala Thr Lys Asp
            355                 360                 365

Thr Tyr Asp Ala Leu His Met Gln Ala Leu Pro Pro Arg Ser Gly Ser
            370                 375                 380

Gly Ser Gly Ser Gly Ser Met Val Ser Lys Gly Glu Glu Leu Phe Thr
385                 390                 395                 400

Gly Val Val Pro Ile Leu Val Glu Leu Asp Gly Asp Val Asn Gly His
            405                 410                 415

Lys Phe Ser Val Ser Gly Glu Gly Glu Gly Asp Ala Thr Tyr Gly Lys
            420                 425                 430

Leu Thr Leu Lys Phe Ile Cys Thr Thr Gly Lys Leu Pro Val Pro Trp
            435                 440                 445

Pro Thr Leu Val Thr Thr Leu Thr Tyr Gly Val Gln Cys Phe Ser Arg
            450                 455                 460

Tyr Pro Asp His Met Lys Gln His Asp Phe Phe Lys Ser Ala Met Pro
465                 470                 475                 480

Glu Gly Tyr Val Gln Glu Arg Thr Ile Phe Phe Lys Asp Asp Gly Asn
                485                 490                 495

Tyr Lys Thr Arg Ala Glu Val Lys Phe Glu Gly Asp Thr Leu Val Asn
            500                 505                 510

Arg Ile Glu Leu Lys Gly Ile Asp Phe Lys Glu Asp Gly Asn Ile Leu
            515                 520                 525

Gly His Lys Leu Glu Tyr Asn Tyr Asn Ser His Asn Val Tyr Ile Met
            530                 535                 540

Ala Asp Lys Gln Lys Asn Gly Ile Lys Ala Asn Phe Lys Ile Arg His
545                 550                 555                 560

Asn Ile Glu Asp Gly Ser Val Gln Leu Ala Asp His Tyr Gln Gln Asn
                565                 570                 575

Thr Pro Ile Gly Asp Gly Pro Val Leu Leu Pro Asp Asn His Tyr Leu
            580                 585                 590

Ser Thr Gln Ser Ala Leu Ser Lys Asp Pro Asn Glu Lys Arg Asp His
            595                 600                 605

Met Val Leu Leu Glu Phe Val Thr Ala Ala Gly Ile Thr Leu Gly Met
            610                 615                 620

Asp Glu Leu Tyr Lys
625

<210> SEQ ID NO 156
<211> LENGTH: 1887
```

<212> TYPE: DNA
<213> ORGANISM: Artificial sequence
<220> FEATURE:
<223> OTHER INFORMATION: Synthetic polynucleotide, encoding
      NKG2D.AF_CD8hingeTM_4-1BB_CD3zeta_EGFP complete chimeric antigen
      receptor

<400> SEQUENCE: 156

```
atggcattgc ctgttacagc tctgctgctg cccctggctc tgcttctgca tgctgccaga      60
cctctgttca atcaagaggt gcagatccct ctgaccgaga gctactgtgg ccctgtcct     120
aagaactgga tctgctacaa gaacaactgc taccagttct tcgacgagag caagaattgg    180
tacgagagcc aggccagctg catgagccag aatgccagcc tgctgaaggt gtacagcaaa    240
gaggaccagg atctgctgaa gctggtcaag agcgcccact ggatgggact cgtgcacatc    300
cctacaaacg gcagctggca gtgggaggac ggctctatcc tgtctcctaa cctgctgacc    360
atcatcgaga tgcagaaggg cgactgcgcc ctgtacgcca gcagctttaa gggcttcatc    420
gagaactgca gcaccccta cacctacatc tgtatgcagc ggaccgtgac caccacacca    480
gctcctagac ctccaactcc tgctcctaca atcgccagcc agcctctgtc tctgaggcca    540
gaagcttgta gacctgctgc aggcggagcc gtgcatacaa gaggactgga tttcgcctgc    600
gacatctaca tctgggcccc tctggctgga acatgtggcg tgctgctgct gagcctggtc    660
atcaccctgt actgcagcct gaagcggggc agaaagaagc tgctgtacat ctttaagcag    720
cccttcatgc ggcccgtgca gaccacacaa gaggaagatg gctgctcctg cagattcccc    780
gaggaagaag aaggcggctg cgagctgaga gtgaagttca gccgttctgc cgacgctccc    840
gcctataagc agggacagaa ccagctgtac aacgagctga acctggggag aagagaagag    900
tacgacgtgc tggacaagcg agaggcagaa gatcctgaga tgggcggcaa gcccagacgg    960
aagaatcctc aagagggcct gtataatgag ctgcagaaag acaagatggc cgaggcctac   1020
agcgagatcg gaatgaaggg cgagcgcaga gaggcaaggg acacgatgg actgtaccag    1080
ggcctgagca ccgccaccaa ggatacctat gatgccctgc acatgcaggc cctgcctcca   1140
agatcaggct ctggttctgg cagcggcagc atggtgtcta aaggcgagga actgttcacc   1200
ggcgtggtgc ccattctggt ggaactggac ggggatgtga acggccacaa gtttagcgtt   1260
agcggcgaag gcgaagggga tgccacatac ggaaagctga ccctgaagtt catctgcacc   1320
accggcaagc tgcctgtgcc ttggcctaca ctggtcacca cactgacata cggcgtgcag   1380
tgctttagca gataccccga ccatatgaag cagcacgact tcttcaagtc cgccatgcct   1440
gagggctacg tgcaagagcg gaccatcttc tttaaggacg acggcaacta caagaccagg   1500
gccgaagtga gtttgaggg cgacacccctg gtcaaccgga tcgagctgaa gggcatcgac   1560
ttcaaagagg atggcaacat cctgggccac aagctcgagt acaactacaa cagccacaac   1620
gtgtacatca tggccgacaa gcagaagaac ggcatcaagg ccaacttcaa gatccggcac   1680
aacatcgagg acggcagcgt tcagctggcc gatcactacc agcagaacac ccctatcgga   1740
gatggccctg tgctgctccc cgacaatcac tacctgagca cacagagcgc cctgagcaag   1800
gaccccaacg agaagaggga tcacatggtg ctgctggaat ttgtgaccgc cgcaggcatc   1860
accctcggca tggacgaact gtacaaa                                       1887
```

<210> SEQ ID NO 157
<211> LENGTH: 11
<212> TYPE: PRT
<213> ORGANISM: Artficial sequence
<220> FEATURE:

```
<223> OTHER INFORMATION: Synthetic

<400> SEQUENCE: 157

Ala Pro Thr Ser Ser Ser Gly Gly Gly Gly Ser
1               5                   10

<210> SEQ ID NO 158
<211> LENGTH: 4
<212> TYPE: PRT
<213> ORGANISM: Artificial sequence
<220> FEATURE:
<223> OTHER INFORMATION: Synthetic

<400> SEQUENCE: 158

Gly Gly Gly Ser
1
```

MODIFIED A1-A2 DOMAINS OF NON-NATURAL NKG2D LIGANDS THAT BIND NON-NATURAL NKG2D RECEPTORS

BACKGROUND OF THE INVENTION

Field of the Invention

This application relates generally to the production of polypeptides comprised of modified α1-α2 domains of NKG2D ligands which bind specifically to a non-natural ectodomain of a non-natural NKG2D receptor and wherein heterologous molecules are attached to the modified α1-α2 domains of NKG2D ligands.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named "50003_seq_ST25.txt", 306,954 bytes, created on Apr. 17, 2023.

Background Information

NKG2D is an activating receptor expressed as a type II homodimeric integral protein on the surface of Natural Killer (NK) cells and certain T cells. When bound to one of its eight natural ligands expressed primarily on the surfaces of distressed cells, the NKG2D activates the NK cell to kill the stressed cell, or when on T cells, the ligand-occupied NKG2D co-stimulates the T cell to carry out its effector function. The three-dimensional structures have been solved for the ectodomain of human natural NKG2D, several of its soluble natural ligands and, in some cases, the bound complex of soluble ligand and receptor ectodomain. The monomeric α1-α2 domains of NKG2D ligands bind specifically to the two ectodomains of the natural NKG2D homodimer.

SUMMARY OF THE INVENTION

The present disclosure relates to modified α1-α2 domains of NKG2D ligands attached to heterologous molecules including polypeptides, in some embodiments antibodies or fragments of antibodies. The invention also relates to modified forms of the NKG2D receptor engineered to provide a combination of enhanced and diminished binding to non-natural and natural versions of NKG2D ligands, respectively.

BRIEF DESCRIPTION OF THE DRAWINGS

FIG. 1A. Alignment of the natural NKG2D.wt ectodomain (SEQ ID NO: 17) along with the NKG2D.YA (SEQ ID NO: 18) and NKG2D.AF (SEQ ID NO: 25) non-natural variants. Indicated are the locations of Y152 and Y199 and highlighted in gray are the mutated residues present in the non-natural variants.

FIG. 1B. Alignment of the α1-α2 domain of natural/wild-type ULBP2 (SEQ ID NO: 4) and non-natural variants of ULBP2 including ULBP2.R80W (SEQ ID NO: 108). Highlighted in gray are the residues critical for binding of non-natural ULBP2 variants to the non-natural NKG2D.YA or NKG2D.AF receptors. Indicated are the locations of residue R80 as well as the M154-F159 region that was explored for orthogonal variants binding to NKG2D.YA (ULBP2.S3, SEQ ID NO.: 127) or NKG2D.AF (ULBP2.C, SEQ ID NO.: 111; ULBP2.R, SEQ ID NO.: 113; ULPB2.AA, SEQ ID NO.: 115; and ULBP2.AB, SEQ ID NO.: 117).

FIG. 2. Summary of candidate, non-natural Fc-eNKG2D variant mutations and protein aggregation properties determined by Size-Exclusion Chromatography (SEC), as depicted in FIGS. 3 and 4.

FIG. 5. Percent saturation (Rmax) of eNKG2D variants normalized to wild-type NKG2D binding by either MICwed-MicAbody or to MIC25-MicAbody. Wild-type Fc-NKG2D and each Fc-eNKG2D receptor were captured on AHC biosensors then exposed to trastuzumab-specific MicAbodies at 20 nM. Dissociation kinetics were monitored and the Rmax values of the Fc-eNKG2D fusions ranked. Those samples not tested (nt) were due to either severe aggregation or inadequate amount of material expressed or recovered after SEC fractionation.

FIG. 7. EC50 values (nM) for Fc-eNKG2D ELISAs shown in FIG. 4. nt=not tested; nb=no binding or very low binding even at 300 nM so EC50 value not calculated.

FIG. 8. Binding of eNKG2D variants to wild-type ligands. Wild-type ligands (all in Fc-fusion format) were captured onto Octet® AHC biosensors, and each natural NKG2D, NKG2D.Y152A, or eNKG2D5 (Y152A/Y199F) as an Fc-fusion was titrated from 300 nM to 0.41 nM. Maximal binding responses were quantified by Octet®. (Note the different ordinates for each graph).

FIG. 9. Subset of combinatorial mutations within ULBP2 that resulted in phage clones with selective binding to NKG2D.AF versus natural NKG2D.wt as verified by spot ELISA. Mutants were ranked by frequency of appearance among the selected phages.

FIG. 11. Specificity of NKG2D.AF-selected ULBP2 variants in rituximab-MicAbody format retained their binding to NKG2D.AF by quantitative ELISA. The specific amino acid modifications of each ULBP2 variant are shown as are the ratios of their binding to Fc-NKG2D.wt fusion versus Fc-NKG2D.AF fusion. The amino acid residue locations of ULBP2 are those of FIG. 1B.

FIG. 12. Selected mutations at the indicated amino acid locations of ULBP2.R80W (FIG. 1B; SEQ ID NO: 108) that resulted in Y152A-specific phage clones.

Figure 3:
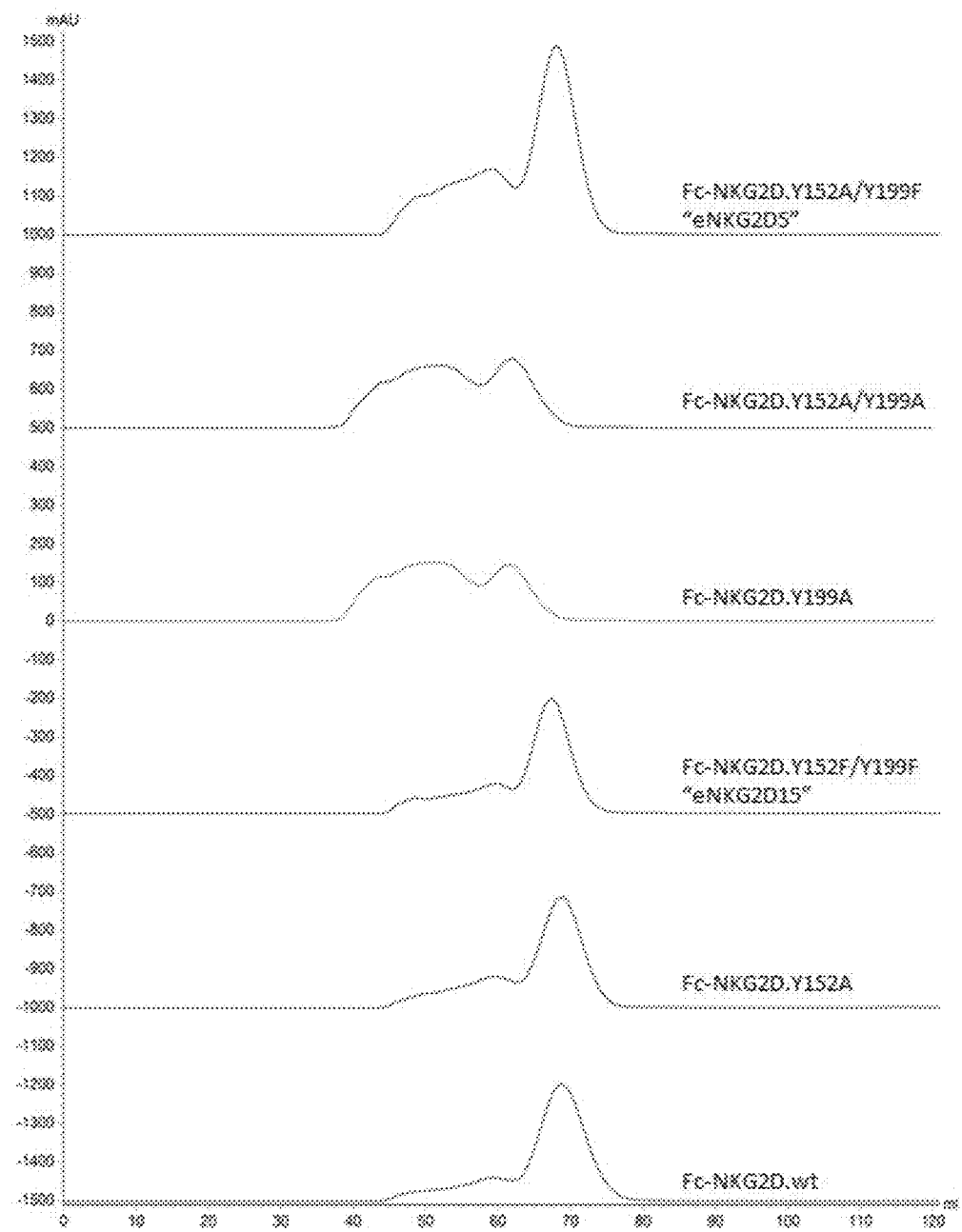
FIG. 3. Size-exclusion chromatography comparison of non-natural Fc-NKG2D fusion proteins analyzed on an Akta HiLoad® 16/600 Superdex® 200 column. Migration of correctly assembled material was exemplified by a discrete, symmetrical peak that eluted at higher volumes while aggregated material eluted sooner at lower volumes. The site and nature of the modifications are indicated by the amino acid numbers Y152, Y199, or both (SEQ ID NOS: 48, 43, 42, 58, 41, and 40 starting from the top of the figure).

Viral infection is a common inducer of MIC protein expression and identifies the viral-infected cell for NK or T cell attack (Groh et al. 1998; Groh et al. 2001. Co-stimulation of CD8+ αβT cells by NKG2D via engagement by MIC induced on virus-infected cells. *Nat. Immunol.* 2: 255-260; Cerwenka, A., and L. L. Lanier. 2001). In fact, to avoid such an attack on its host cell, cytomegalovirus and other viruses have evolved mechanisms that prevent the expression of MIC proteins on the surface of the cell they infect in order to escape targeting by the innate immunity system (Lodoen, M., K. Ogasawara, J. A. Hamerman, H. Arase, J. P. Houchins, E. S. Mocarski, and L. L. Lanier. 2003. NKG2D-mediated NK cell protection against cytomegalovirus is impaired by gp40 modulation of RAE-1 molecules. *J. Exp. Med.* 197:1245-1253; Stern-Ginossar et al., (2007) Host immune system gene targeting by viral miRNA. *Science* 317: 376-381; Stern-Ginossar et al., (2008) Human microRNAs regulate stress-induced immune responses mediated by the receptor NKG2D. *Nature Immunology* 9: 1065-73; Slavuljica, I A Busche, M Babic, M Mitrovic, I Gašparovic, D Cekinovic, E Markova Car, E P Pugel, A Cikovic, V J Lisnic, W J Britt, U Koszinowski, M Messerle, A Krmpotic and S Jonjic. 2010. Recombinant mouse cytomegalovirus expressing a ligand for the NKG2D receptor is attenuated and has improved vaccine properties. *J. Clin. Invest.* 120: 4532-4545).

The expression of MIC proteins is also induced on many tumor cells where their presence can render them sensitive to targeting and lysis by NK cells. Not surprisingly, a failure to express MIC protein constitutes one means by which many malignant cells, such as those of lung cancer and glioblastoma brain cancer, can escape the innate immune system (Busche, A et al. 2006, NK cell mediated rejection of experimental human lung cancer by genetic over expression of MHC class I chain-related gene A. *Human Gene Therapy* 17: 135-146; Doubrovina, E S, M M Doubrovin, E Vider, R B Sisson, R J O'Reilly, B Dupont, and Y M Vyas, 2003. Evasion from NK Cell Immunity by MHC Class I Chain-Related Molecules Expressing Colon Adenocarcinoma (2003) *J. Immunology* 6891-99; Friese, M. et al. 2003. MICA/NKG2D-mediated immunogene therapy of experimental gliomas. *Cancer Research* 63: 8996-9006; Fuertes, M B, M V Girart, L L Molinero, C I Domaica, L E Rossi, M M Barrio, J Mordoh, G A Rabinovich and N W Zwirner. (2008) Intracellular Retention of the NKG2D Ligand MHC Class I Chain-Related Gene A in Human Melanomas Confers Immune Privilege and Prevents NK Cell-Mediated Cytotoxicity. *J. Immunology*, 180: 4606-4614).

The high resolution structure of human MICA bound to NKG2D has been solved and demonstrates that the α3 domain of MICA has no direct interaction with the NKG2D (Li et al. 2001. Complex structure of the activating immunoreceptor NKG2D and its MHC class I-like ligand MICA. *Nature Immunol.* 2: 443-451; Protein Data Bank accession code 1HYR). The α3 domain of MICA, like that of MICB, is connected to the α1-α2 platform domain by a short, flexible linker peptide, and itself is positioned naturally as "spacer" between the platform and the surface of the MIC expressing cell. The three-dimensional structures of the human MICA and MICB α3 domains are nearly identical (root-mean square distance <1 Å on 94 C-αα's) and functionally interchangeable (Holmes et al. 2001. Structural Studies of Allelic Diversity of the MHC Class I Homolog MICB, a Stress-Inducible Ligand for the Activating Immunoreceptor NKG2D. *J Immunol.* 169: 1395-1400).

Certain non-natural α1-α2 domains of NKG2D ligands modified to bind natural human NKG2D receptors with higher affinities than do natural α1-α2 domains have been described (Candice S. E. Lengyel, Lindsey J. Willis, Patrick Mann, David Baker, Tanja Kortemme, Roland K. Strong and Benjamin J. McFarland. Mutations Designed to Destabilize the Receptor-Bound Conformation Increase MICA-NKG2D Association Rate and Affinity. *Journal of Biological Chemistry* Vol. 282, no. 42, pp. 30658-30666, 2007; Samuel H. Henager, Melissa A. Hale, Nicholas J. Maurice, Erin C. Dunnington, Carter J. Swanson, Megan J. Peterson, Joseph J. Ban, David J. Culpepper, Luke D. Davies, Lisa K. Sanders, and Benjamin J. McFarland. Combining different design strategies for rational affinity maturation of the MICA-NKG2D interface. *Protein Science* 2012 VOL 21:1396-1402. Herein we describe non-natural α1-α2 domains of NKG2D ligands that have been modified to bind non-natural NKG2D receptors, themselves mutated at two specific sites, each of which alone results in compromised or loss of binding to all currently known natural α1-α2 domains of human NKG2D ligands (David J. Culpepper, Michael K. Maddox, Andrew B. Caldwell, and Benjamin J. McFarland. Systematic mutation and thermodynamic analysis of central tyrosine pairs in polyspecific NKG2D receptor interactions. (*Mol Immunol.* 2011 January; 48(4): 516-523).

The instant invention created bispecific molecules comprised of (a) the specifically modified non-natural α1-α2 domains and (b) specifically targeting heterologous molecules, including but not limited to heterologous peptides or polypeptides. The bispecific molecules can bind Chimeric Antigen Receptors (CARs) wherein the Receptor of the CAR is comprised of the non-natural NKG2D receptor ectodomain that binds its cognate modified α1-α2 domains with greater affinity than it does natural α1-α2 domains. The second specificity of the bispecific molecule is comprised of a heterologous component that binds specifically its own respective target molecule. Genetically engineered cells of the immunity system comprised of such CARs and the cognate bispecific molecules can then overcome many of the disadvantages, including known severe systemic toxicities, antigen escape, and limited and uncontrolled persistence of current CAR-T and CAR-NK cell therapeutics (Kalos M, Levine, BL, Porter, D L, Katz, S, Grupp, S A, Bagg, A and June, C. T Cells with chimeric antigen receptors have potent antitumor effects and can establish memory in patients with advanced leukemia. *Sci Transl Med* 2011; 3:95ra73; Morgan R A, Yang J C, Kitano M, Dudley M E, Laurencot C M, Rosenberg S A. Case report of a serious adverse event following the administration of T cells transduced with a chimeric antigen receptor recognizing ERBB2. *Mol Ther* 2010, 18:843-851).

T cells and NK-cells can be modified using gene transfer technologies to directly and stably express on their surface transmembrane signaling receptors that confer novel antigen specificities on the T cell by virtue of binding domains taken from antibodies (Saar Gill & Carl H. June. Going viral: chimeric antigen receptor T cell therapy for hematological malignancies. *Immunological Reviews* 2015. Vol. 263: 68-89; Wolfgang Glienke, Ruth Esser, Christoph Priesner, Julia D. Suerth, Axel Schambach, Winfried S. Wels, Manuel Grez, Stephan Kloess, Lubomir Arseniev and Ulrike Koehl. 2015. Advantages and applications of CAR-expressing natural killer cells. *Front. Pharmacol.* doi: 10.3389/fphar.2015.00021). Such chimeric antigen receptor-expressing T cells (CAR-T cells) are applications of this approach that combines an antigen recognition domain of a specific antibody with an intracellular domain of the CD3-7 chain, which is the primary transmitter of signals from endogenous T cell antigen Receptors (TCRs), into a single chimeric protein along with a cytoplasmic polypeptide sequence from a co-stimulatory molecule such as CD27, CD28, ICOS, 4-1BB, or OX40. CARs so constructed can trigger T cell activation upon binding the targeted antigen in a manner similar to an endogenous T cell receptor but independent of the major histocompatibility complex (MHC).

As used herein, a "soluble MIC protein", "soluble MICA" and "soluble MICB" refer to a MIC protein containing the $\alpha1$, $\alpha2$, and $\alpha3$ domains of the MIC protein but without the transmembrane or intracellular domains. The NKG2D ligands, ULBP1-6, do not naturally possess an $\alpha3$ domain (Cerwenka A, Lanier L L. 2004. NKG2D ligands: unconventional MHC class I-like molecules exploited by viruses and cancer. *Tissue Antigens* 61 (5): 335-43. doi:10.1034/j.1399-0039.2003.00070.x. PMID 12753652). An "$\alpha1$-$\alpha2$ domain" of an NKG2D ligand refers to the protein domain of the ligand that binds an NKG2D receptor.

In some embodiments, the $\alpha1$-$\alpha2$ domains of the non-natural NKG2D ligand proteins of the invention are at least 80% identical or homologous to the native or natural $\alpha1$-$\alpha2$ domain of an NKG2D ligand (SEQ ID NOs: 1-9 for MICA, MICB, ULBP1, ULBP2, ULBP3, ULBP4, ULBP5, ULBP6, and OMCP, respectively). In other embodiments, the modified $\alpha1$-$\alpha2$ domain is at least 85% identical to a native or natural $\alpha1$-$\alpha2$ domain of an NKG2D ligand. In yet other embodiments, the modified $\alpha1$-$\alpha2$ domain is at least 90% identical to a native or natural $\alpha1$-$\alpha2$ domain of a natural NKG2D ligand protein and binds non-natural NKG2D.

Preferably the modified or non-natural $\alpha1$-$\alpha2$ domains of the non-natural MIC proteins of the invention are at least 80% identical or homologous to the native or natural $\alpha1$-$\alpha2$ domain of OMPC (SEQ ID NO.: 9) or to one of the eight known human NKG2D ligand proteins (SEQ ID NOs: 1-8) and bind the non-natural NKG2D ectodomain. In some embodiments, the non-natural α1-α2 domain is at least 85% identical to a native or natural α1-α2 domain of an NKG2D ligand protein and binds the non-natural NKG2D. In other embodiments, the non-natural α1-α2 platform domain is at least 90%, 95%, 96%, 97%, 98%, or 99% identical to a native or natural α1-α2 platform of a human natural α1-α2 domain protein and binds the non-natural NKG2D.

In some embodiments, a heterologous molecular tag may be fused to the N-terminus or C-terminus of a non-natural α1-α2 domain of a soluble MIC protein to aid in the purification of the soluble MIC protein. Tag sequences include peptides such as a poly-histidine, myc-peptide, a FLAG tag, streptavidin-like tag, or a small molecule such as biotin. Such tags may be removed after isolation of the MIC molecule by methods known to one skilled in the art.

In other embodiments of the invention, specific mutations in α1-α2 domains of NKG2D ligands can be made to create non-natural α1-α2 domains that bind non-natural NKG2D receptors, themselves engineered so as to have reduced affinity for natural NKG2D ligands. This can be done, for example, through genetic engineering. A non-natural NKG2D receptor so modified can be used to create on the surface of NK-cells, T cells, or other cells of the immune system an NKG2D-based Chimeric Antigen Receptor (CAR) that can preferentially bind to and be activated by molecules comprised of the invented non-natural α1-α2 domains. These pairs of non-natural NKG2D receptors and their invented cognate non-natural NKG2D ligands will provide important safety, efficacy, and manufacturing advantages for treating cancer and viral infections as compared to the current CAR-T cells and CAR-NK cells, as described below.

Engineering T cells with CARs has emerged as a promising approach to adoptive T cell therapy for cancer, and CARs targeting many different molecules have been tested in CAR-T cells as therapeutics for malignancies (Porter D L, Levine B L, Kalos M, Bagg A, June C H., 2011. Chimeric antigen receptor-modified T cells in chronic lymphoid leukemia. *N Engl J Med.* 365:725-733). While remarkable clinical efficacy has been observed in hundreds of patients receiving adoptive transfer of T cells expressing CD19-specific chimeric antigen receptors, the processes of custom engineering a CAR to target a specific antigen, isolating autologous T cells from the patient, genetically engineering the autologous T cells to express the personalized CAR, expanding the modified cells in vitro, and controlling the quality their production have all been onerous and expensive.

Once the autologous CAR-T cells are infused back into the donor patient, their expansion in vivo cannot be controlled, creating what has been dubbed a "living therapy" which does not demonstrate a dose-response relationship with efficacy (Gill & June 2015). Furthermore, tumor escape from the CAR-T cell can occur through antigen loss on tumor cells (Stephan A. Grupp, M.D., Ph.D., Michael Kalos, Ph.D., David Barrett, M.D., Ph.D., Richard Aplenc, M.D., Ph.D., David L. Porter, M.D., Susan R. Rheingold, M.D., David T. Teachey, M.D., Anne Chew, Ph.D., Bernd Hauck, Ph.D., J. Fraser Wright, Ph.D., Michael C. Milone, M.D., Ph.D., Bruce L. Levine, Ph.D., and Carl H. June, M.D. Chimeric Antigen Receptor-Modified T Cells for Acute Lymphoid Leukemia. N Engl J Med 2013; 368:1509-1518). While this escape pathway can be addressed by sequential therapy with a differently targeted CAR-T cell or by an initial infusion of a T cell product containing CARs of two or more specificities, such steps represent a significant additional expansion in the manufacturing processes, quality control, and costs.

In addition to CAR-T cells targeting tumors with single chain antibody binding domains (scFv), CAR-T cells that employ the ligand-binding domain of the NKG2D receptor have been studied in animals and recently in humans (Sentman C L, Meehan K R. NKG2D CARs as cell therapy for cancer. *Cancer J.* 2014 March-April; 20(2):156-9. doi: 10.1097/PPO.0000000000000029; Manfred Lehner, Gabriel Götz, Julia Proff, Niels Schaft, Jan Dörrie, Florian Full, Armin Ensser, Yves A. Muller, Adelheid Cerwenka, Hinrich Abken, Ornella Parolini, Peter F. Ambros, Heinrich Kovar, Wolfgang Holter. Redirecting T Cells to Ewing's Sarcoma Family of Tumors by a Chimeric NKG2D Receptor Expressed by Lentiviral Transduction or mRNA Transfection. Research Article|published 15 Feb. 2012|*PLOS ONE* 10.1371/journal.pone.0031210; www.clinicaltrials.gov NCT02203825). Since NKG2D ligand expression is increased on the surface of stressed cells, such as tumor cells, this family of natural NKG2D ligands is of significant interest as targets for cancer immunotherapies (Spear P, Wu M R, Sentman M L, Sentman C L. NKG2D ligands as therapeutic targets. *Cancer Immun.* 2013 May 1; 13:8; Song D G, Ye Q, Santoro S, Fang C, Best A, Powell D J Jr., Chimeric NKG2D CAR-expressing T cell-mediated attack of human ovarian cancer is enhanced by histone deacetylase inhibition. *Hum Gene Ther.* 2013 March; 24(3): 295-305). One NKG2D CAR was a fusion of the full-length NKG2D receptor and CD3ζ (NKG2Dζ); another was with only the ectodomain of NKG2D fused to a second-generation CAR scaffold composed of transmembrane and intracellular domains from CD28 and the signaling domain of CD3ζ (NKG2D28γ). Since activation of NKG2D is dependent upon the presence of DAP10, a CAR-T cell was also constructed wherein DAP10 was co-expressed with NKG2Dζ (NKG2Dζ10). T cells expressing any of the above NKG2D CARs produced IFNγ and TNFα in response to NKG2D ligand stimulation and in vitro efficiently killed tumor targets expressing NKG2D ligands (Heather VanSeggelen, Joanne A. Hammill, Anna Dvorkin-Gheva, Daniela G. M. Tantalo, Jacek M. Kwiecien, Galina F. Denisova, Brian Rabinovich, Yonghong Wan, Jonathan L. Bramson, T cells engineered with chimeric antigen receptors targeting NKG2D ligands display lethal toxicity in mice, *Molecular Therapy* 2015 October; 23(20):1600-10; doi:10.1038/mt.2015.119). The cytotoxic potential of NK cells against a wide spectrum of tumor subtypes could also be markedly enhanced by expression of a CAR based on NKG2D-DAP10-CD3ζ (Yu-Hsiang Chang, John Connolly, Noriko Shimasaki, Kousaku Mimura, Koji Kono, and Dario Campana. Chimeric Receptor with NKG2D Specificity Enhances Natural Killer Cell Activation and Killing of Tumor Cells. *Cancer Res;* 73(6) Mar. 15, 2013).

However, following infusion into syngeneic murine hosts, significant toxicity occurred with these CAR-T constructs that bind and are activated by natural ligands of the natural NKG2D receptor. Signs of toxicity, including poor body condition, hunched posture, labored breathing, and decreased core body temperature were observed in tumor-bearing and tumor-free mice treated with NKG2D-based CAR-T cells as compared to untreated control mice. The severity of NKG2D CAR-T cell toxicity varied, with NKG2Dζ10 being severely toxic, NKG2D28ζ showing intermediate toxicity, and NKG2Dζ being tolerable. Clinical symptoms of toxicity and mortality rates were exacerbated when mice received chemotherapy prior to adoptive transfer of T cells expressing any of the NKG2D CARs (VanSeggelen et al. 2015). Chemotherapy and radiation are known to induce NKG2D ligands on otherwise healthy tissues (Xiulong Xu, Geetha S Rao, Veronika Groh, Thomas Spies, Paolo Gattuso, Howard L Kaufman, Janet Plate and Richard A Prinz. Major histocompatibility complex class I-related chain A/B (MICA/B) expression in tumor tissue and serum of pancreatic cancer: Role of uric acid accumulation in gemcitabine-induced MICA/B expression. *BMC Cancer* 2011, 11:194 doi:10.1186/1471-2407-11-194; Gannagé M, Buzyn A, Bogiatzi S I, Lambert M, Soumelis V, Dal Cortivo L, Cavazzana-Calvo M, Brousse N, Caillat-Zucman Induction of NKG2D ligands by gamma radiation and tumor necrosis factor-alpha may participate in the tissue damage during acute graft-versus-host disease. *Transplantation.* 2008 Mar. 27; 85(6):911-5. doi: 10.1097/TP.0b013e31816691ef.). Further characterization revealed that the toxicity coincided with a systemic cytokine storm and lethal levels of inflammation within the lungs. These data warn that extreme caution must be taken when using natural NKG2D ligands for targeted immunotherapy and demonstrate that T cell expression of CARs targeting such ligands—especially strongly activating CARs—can be detrimental in vivo (VanSeggelen et al. 2015).

CAR-T or CAR-NK cells comprised of ectodomains of non-natural NKG2D receptors that do not or only poorly bind natural NKG2D ligands will not be subject to the above form of activation and thus will not be as toxigenic as cells expressing a CAR based on a natural NKG2D receptor. Furthermore, ectodomains of non-natural NKG2D receptors on cells will not be subject to down-regulation by natural NKG2D ligands in a soluble format or on Myeloid Derived Suppressor Cells (MDSC) (Deng W, Gowen B G, Zhang L, Wang L, Lau S, Iannello A, Xu J, Rovis T L, Xiong N, Raulet D H, 2015. Antitumor immunity. A shed NKG2D ligand that promotes natural killer cell activation and tumor rejection. *Science.* 2015 Apr. 3; 348(6230):136-9. doi: 10.1126/science.1258867. Epub 2015 Mar. 5). However, when such CAR cells bearing ectodomains of the non-natural NKG2D receptors are engaged by bispecific molecules with the cognate non-natural α1-α2 domains of the instant invention and its heterologous targeting motif which has found and bound its intended target, the CAR will be activated and the CAR-cell's effector functions expressed.

Because the cytokine release and cytolytic activities of CAR-T or CAR-NK cells comprised of non-natural NKG2D receptor ectodomains are not initiated except in the presence of an engaged bispecific molecule comprised of a cognate non-natural α1-α2 domain wherein the bispecific molecule has also engaged an array of its target, their activation can be controlled by the administered bispecific molecules, which as biopharmaceuticals will exhibit pharmacokinetics and pharmacodynamics well known in the field. In the event that an adverse event develops, the physician can simply modify the dosing regimen of the administered bispecific molecule rather than having to deploy an induced suicide mechanism to destroy the infused CAR cells as currently done (Monica Casucci and Attilio Bondanza. Suicide Gene Therapy to Increase the Safety of Chimeric Antigen Receptor-Redirected T Lymphocytes. *J Cancer.* 2011; 2: 378-382). Furthermore, such bispecific molecules with different specific targeting motifs can be administered simultaneously or sequentially to help address tumor resistance and escape as a results of target antigen loss without having to create, expand and infuse multiple different autologous CAR cells (Gill & June 2015). Since all CAR constructions can be identical for all CAR cells and the targeting specificity determined simply by the targeting motif of the administered bispecific molecule of the instant invention, CAR-cell manufacturing processes will be simplified and less expensive.

Examples of parent or recipient proteins or polypeptides that are candidates for attachment to non-natural α1-α2 domains of NKG2D ligands include but are not limited to antibodies, proteins comprised of Ig folds or Ig domains, including modified Fc domains that recruit natural molecules or fail to recruit or bind natural molecules, globulins, albumens, fibronectins and fibronectin domains, integrins, fluorescent proteins, enzymes, outer membrane proteins, receptor proteins, T cell receptors, chimeric antigen receptors, viral antigens, virus capsids, viral ligands for cell receptors, histones, hormones, cytokines and modified cytokines such as interleukins, knottins, cyclic peptides or polypeptides, major histocompatibility (MHC) family proteins, MIC proteins, lectins, and ligands for lectins. It is also possible to attach non-protein molecules such a polysaccharides, dendrimers, polyglycols, peptidoglycans, antibiotics, and polyketides to the modified α1-α2 domains of NKG2D ligands.

Thus, the instant invention expands the diversity and practicality of this remarkable, very promising immunologic approach to managing cancer with CAR-T cells, CAR-NK cells, and CAR-macrophage-like cells while overcoming many of these current, recognized difficulties.

As used herein "peptide", "polypeptide", and "protein" are used interchangeably; and a "heterologous molecule", "heterologous peptide", "heterologous sequence" or "heterologous atom" is a molecule, peptide, nucleic acid or amino acid sequence, or atom, respectively, that is not naturally or normally found in physical conjunction with the subject molecule. As used herein, "non-natural" and "modified" are used interchangeably. As used herein, "natural", "native", and "wild-type" are used interchangeably and "NKG2D" and "NKG2D receptor" are used interchangeably. The term "antibody" herein is used in the broadest sense and specifically covers monoclonal antibodies, multispecific antibodies (e.g. bispecific antibodies), and antibody fragments, so long as they exhibit the desired biological activity. "Antibody fragments" comprise a portion of an antibody, preferably comprising the antigen binding region thereof. Examples of antibody fragments include Fab, Fab', F(ab')$_2$, Fv fragments and insertable Fv's; diabodies; linear antibodies; single-chain antibody molecules; and multi-specific antibodies formed from antibody fragment(s). "Antibody fragments" can also comprise the Fc portion of an antibody.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

All references cited herein are hereby incorporated by reference in their entireties, whether previously specifically incorporated or not. As used herein, the terms "a", "an", and "any" are each intended to include both the singular and plural forms.

Having now fully described the invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and may be applied to the essential features hereinbefore set forth.

EXAMPLES

Modified NKG2D Receptor Ectodomain and Modified α1-α2 Domains of NKG2D Ligands

Figure 4:
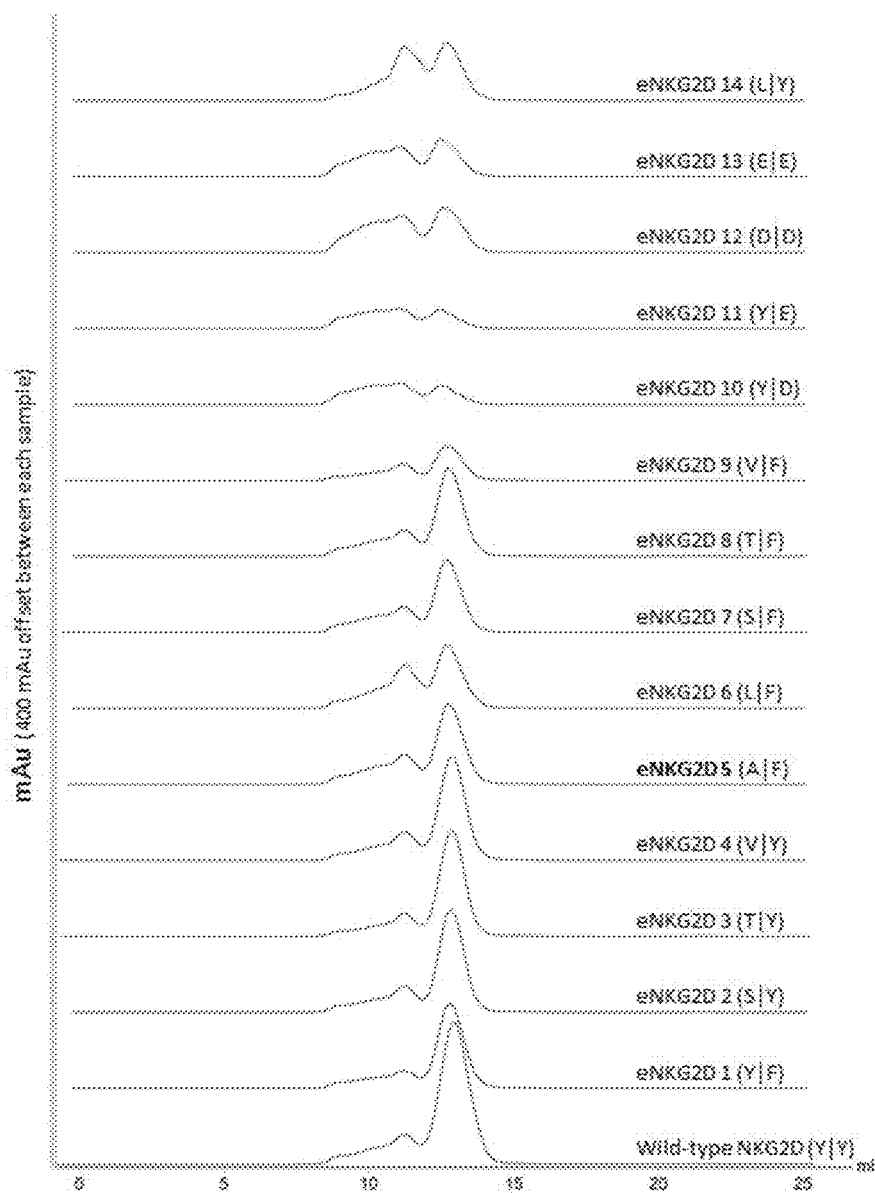
FIG. 4. Size-exclusion chromatography profiles of non-natural Fc-eNKG2D variants with one or two amino acid changes were analyzed on an Akta Superdex® 200 Increase 10/300 GL column. Migration of correctly assembled material is exemplified by a discrete, symmetrical peak eluting at higher volumes while aggregated material-characterized by a low amplitude broad peak or series of peaks-eluted at lower volumes. The letters in parentheses represent the amino acids at positions 152 and 199 (SEQ ID NOs: 57, 56, 55, 54, 53, 52, 51, 50, 49, 48, 47, 46, 45, 44, and 40 in order from the top), respectively.

Example 1. Modification of Tyrosine 152 to Alanine (Y152A) and Tyrosine 199 to Phenylalanine (Y199F) of the Human NKG2D Receptor to Create an Inert NKG2D Ectodomain It had been demonstrated by others that mutations at tyrosine 152 or at tyrosine 199 in human NKG2D, the equivalent of positions 75 and 122 of the NKG2D ectodomain (FIG. 1A, SEQ ID NO.: 17) can greatly reduce binding to the natural ligand, MICA (David J. Culpepper, Michael K. Maddox, Andrew B. Caldwell, and Benjamin J. McFarland. Systematic mutation and thermodynamic analysis of central tyrosine pairs in polyspecific NKG2D receptor interactions. *Mol Immunol.* 2011 January; 48(4): 516-523). We reasoned that while mutation of either tyrosine residue greatly affected the ability of NKG2D to bind to its natural ligands, simultaneous mutation at both tyrosine 152 (Y152) and tyrosine 199 (Y199) would virtually eliminate the receptor's ability to engage with all native ligands. We therefore sought to explore individual and combinatorial Y152 and Y199 substitutions and characterize them with regard to their biochemical behavior with the objective of identifying both single and double-mutant variants incapable of engaging any natural ligands. Those variants that also expressed and assembled well were of particular interest as these signified inert ligands that could be more easily produced for analysis.

Natural NKG2D (wild-type) ectodomain (NKG2D.wt, SEQ ID NO: 17) and candidate non-natural NKG2D variant ectodomains (SEQ ID NOs: 18-35)—also termed "engineered NKG2D" or "eNKG2D" were cloned as fusions to the C-terminus of human IgG1 Fc (without Fab domains), via a short factor Xa recognizable Ile-Glu-Gly-Arg linker (SEQ ID NO: 38) and are interchangeably referred to as Fc-NKG2D.wt or NKG2D.wt and Fc-eNKG2D or eNKG2D (SEQ ID NOs: 40-58). gBlocks® DNA Fragments (Integrated DNA Technologies, San Diego, CA), corresponding to the MHCI signal sequence (SEQ ID NOs: 36 and 37), human IgG1 Fc with linker (SEQ ID NO: 39), and NKG2D ectodomain variants (SEQ ID NOs: 59-77) were synthesized and inserted into pD2610-V12 (ATUM, Newark, CA). DNA constructs exploring substitutions at Y152, Y199, or a combination of Y152/Y199 mutations (FIG. 2) were expressed transiently in Expi293™ cells (ThermoFisher Scientific, Waltham, MA) and secreted protein purified by Protein A affinity chromatography (cat. no. 20334, Pierce Biotechnology, Rockford, IL). Eluted material was characterized by size-exclusion chromatography (SEC) on Akta Pur Superdex® columns and correctly assembled, size-appropriate material was fractionated and isolated from aggregate peaks prior to inclusion in assays.

SEC characterization of purified NKG2D.Y199A-Fc fusion revealed a composition of predominantly aggregated material (FIG. 3). In comparison, both the natural Fc-NKG2D fusion and Fc-NKG2D.Y152A fusion material were distinguished by a discrete, non-aggregated peak that was readily differentiated from more rapidly migrating aggregate. The effect of the Y199A mutation on aggregation was also apparent in the Y152A/Y199A double-mutant Fc-NKG2D fusion variant, indicating that it had an overriding influence on protein misfolding (FIG. 3). This aspect of including Y199A with any combination of Y152 mutations in NKG2D variants therefore presented a challenge for the production of material necessary for subsequent engineering efforts and raised a concern about assembly and presentation on a cell surface. As a consequence, an effort was made to explore other substitutions at Y152 and Y199 that could be combined to yield a more robust molecule. eNKG2D combinatorial Y152 and Y199 mutant candidates were examined as Fc fusions and detailed in (FIG. 2). In addition, all purified and expressed Fc-eNKG2D fusion candidates were profiled by SEC and their chromatograms revealed varying levels of aggregate formation (FIGS. 2-4). Of the single amino acid substitutions explored at residue 152 alanine, serine, threonine, and valine all did not impact assembly of the Fc-NKG2D molecule although Y152-leucine (Y152L) resulted in highly aggregated material. Similar to alanine, neither glutamate nor aspartate were tolerated at position 199, although phenylalanine only modestly increased aggregate formation. Of the combinations of mutations that were explored, Y152A/Y199F, Y152S/Y199F, Y152T/Y199F, and Y152F/Y199F did not negatively impact the desired dimer formation, whereas other combinations resulted in increased aggregation (FIGS. 2-4).

Example 2: Generation of Antibody-Based Bispecific Molecules, "MicAbodies", with Non-Natural NKG2D Ligand Variants To generate non-natural MicA variants fused to human IgG1, the DNA polynucleotides encoding the α1-α2 domains of, for example, MICwed (SEQ ID NO: 79) and MIC25 (SEQ ID NO: 81), were PCR amplified using primers that also introduced the polynucleotide encoding either an APTSSSGGGGS (SEQ ID NO: 157) linker for fusion to C-terminal kappa light chain (SEQ ID NO: 84) or for a GGGS (SEQ ID NO: 158) linker for fusion to C-terminal heavy chain of human IgG1 (SEQ ID NO: 82). Furthermore, two mutations were introduced into the CH2 domain of the heavy chain-D265A/N297A (Kabat numbering)—that reduce binding to all FcγR receptors thus eliminating antibody-dependent cell cytotoxicity (ADCC) function (Shields et al., 2001 *JBC*, 276:6591-6604]. The polynucleotide encoding the α1-α2 domain of wild-type ULBP2 (ULBP2.wt) without its GPI-linkage (SEQ ID NO: 12) was similarly cloned and fused to the DNA polynucleotides encoding the linkers and the IgG1 heavy chain or light chain. These bispecific antibodies—termed "MicAbody™" in the singular, "MicAbodies" in the plural—are bivalent for the fused α1-α2 domain. Examples of antibodies used to generate MicAbodies for the purposes of exploring eNKG2D engineering include but were not limited to trastuzumab (SEQ ID NOs: 94 and 96) and ritixumab (SEQ ID NOs: 98 and 100) and subsequently termed "trastuzumab-MicAbody" (e.g. SEQ ID NOs: 102 and 104) and "rituximab-MicAbody" (e.g. SEQ ID NO: 106), respectively. The fusion constructs were inserted individually into pD2610-V12 (ATUM, Newark, CA) via Gibson cloning (New England Biolabs Inc., Ipswich, MA). For a given antibody recognizing a specific antigen, the plasmid encoding the heavy chain and the plasmid encoding the light chain fused to either natural or non-natural NKG2D ligand were co-transfected for transient expression in Expi293™ cells (ThermoFisher Scientific, Waltham, MA). Alternatively, the plasmid encoding the heavy chain fused to either natural or non-natural NKG2D ligand and the plasmid for light chain were co-transfected. Secreted bispecific antibodies were purified by Protein A affinity chromatography (cat. no. 20334, Pierce Biotechnology, Rockford, IL), eluted material was characterized by size-exclusion chromatography (SEC) on Akta Pur Superdex® columns, and fractionation performed as needed. In addition, SDS-PAGE analysis was performed on purified samples to verify the expected molecular weights of the fused heavy chain and fused light chain species.

Example 3: Identifying Modified NK2GD Variants Incapable of Binding to Either Natural NKG2D-Binding Ligands or to Non-Natural Ligands that have Enhanced Binding to Wild-Type NKG2D The binding affinities of α1-α2 variants to the extracellular domains of natural (wild-type) NKG2D and non-natural eNKG2D proteins were analyzed using a plate-based ELISA method. Each of the SEC fractionated natural Fc-NKG2D and non-natural Fc-eNKG2D fusions were coated overnight at 4° C. onto separate wells of Nunc Maxisorp 96 well plates (Thermo Fisher Scientific, Waltham, MA) using a coating concentration of 1 μg/mL in phosphate-buffered saline (PBS). The plates were washed three times in PBS/0.05% Tween-20 (PBS-T) at 20-22° C., and blocked with 0.5% bovine serum albumin in PBS (PBS-B) for 2 hours at 20-22° C. MicAbodies were titrated against the plate-bound natural or non-natural Fc-NKG2D fusions for 60 minutes at 20-22° C. in PBS/0.5% bovine serum albumin (BSA)/0.05% Tween-20 (PBS-BT), washed 3 times with PBS-T at 20-22° C., and the bound bispecific proteins detected using an HRP-conjugated anti-human kappa in PBS-BT (Abcam, Cambridge MA) and developed with 1-Step™ Ultra TMB ELISA Substrate Solution (Thermo Fisher Scientific, Waltham, MA). The binding of the ULBP2.wt rituximab-MicAbody (SEQ ID NOs: 98 and 106) discriminated between wild-type NKG2D and eNKG2D variants with reduced binding to the latter, and ligand variants—MICwed (SEQ ID NOs: 96 and 102) and MIC25 (SEQ ID NOs: 96 and 104)—were more stringent at identifying eNKG2D variants with abolished ligand binding. The binding behaviors for each eNKG2D variant against all three bispecific ligands revealed the combinations of NKG2D modifications that led to the greatest reduction in binding of wild-type and variant ligands and enabled the selection of lead inert NKG2D variants.

Additional biophysical analysis of eNKG2D variant binding to ligands was also performed with Bio-Layer Interferometry (BLI) using the ForteBio Octet® system (all FortéBio LLC, Fremont, CA). For these experiments human NKG2D ligands MICA-Fc, MICB-Fc, ULBP1-Fc, ULBP2-Fc, ULBP3-Fc, and ULBP4-Fc were purchased from R&D Systems, Inc. (Minneapolis, MN). Ligands in the MicAbody format were captured on anti-human IgG Fc capture (AHC) biosensor tips. After a baselines were established, tips were exposed to a titration series of Fc-eNKG2D fusion proteins ranging from 300 nM to 0.41 nM and association/dissociation kinetics monitored with all steps performed in PBS-BT. Subsequently, Fc-eNKG2D fusion proteins were captured onto AHC tips and MicAbodies were titrated to characterize binding kinetics.

To determine the maximum response as defined by binding of natural NKG2D to either MICwed or MIC25, natural Fc-NKG2D fusions were captured onto AHC biosensors and 20 nM trastuzumab-MICwed or 20 nM trastuzumab-MIC25 MicAbodies were incubated for two minutes and then dissociation kinetics observed for 30 seconds. Binding analysis under the same conditions was then performed with Fc-eNKG2D fusion receptors as the capture agent, and the level of binding for each eNKG2D ranked as a percentage of the maximal binding response established by Fc-NKG2D.wt (FIG. 5). For MICwed, the responses of all single mutant Fc-eNKG2D variants, except for Y199F, were diminished to 50%. Y199F maintained 100% binding response. However, all double-mutant Fc-eNKG2D variants had completely abolished binding to MICwed. For MIC25, all single mutant Fc-eNKG2D variants and Y152V/Y199F maintained 100% binding response relative to wild-type Fc-NKG2D binding. However, binding was reduced to 50% with several of the double-mutant Fc-eNKG2D variants including Y152A/Y199F, Y152S/Y199F, and Y152T/Y199F.

Figure 6:
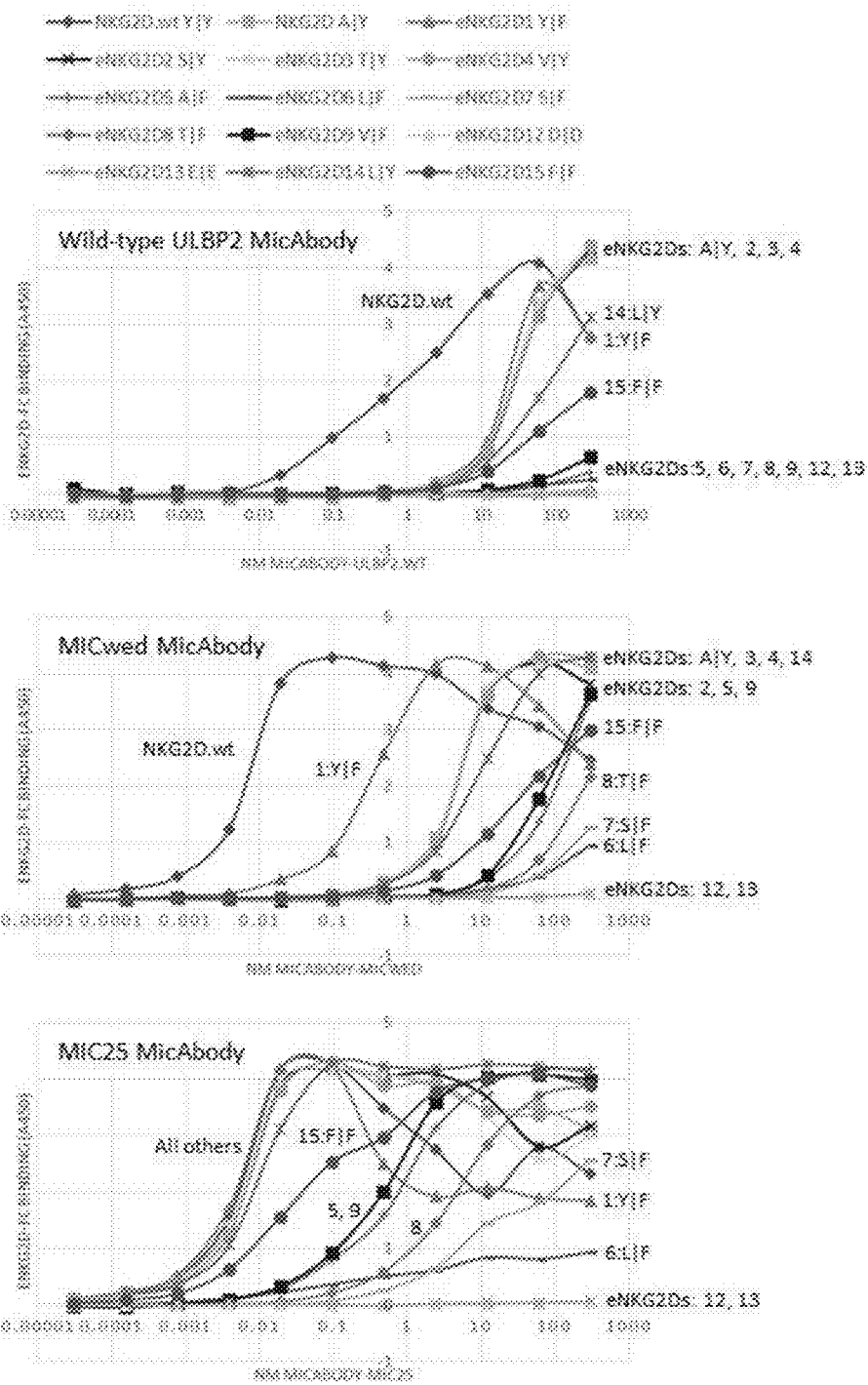
FIG. 6. ELISA binding of ULBP2 wild-type, MICwed- and MIC25-rituximab MicAbodies to Fc-eNKG2D candidates. Key is indicated at the top of the figure, but since many of the curves overlapped, individual curves were also labeled in each graph.
Figure 10:
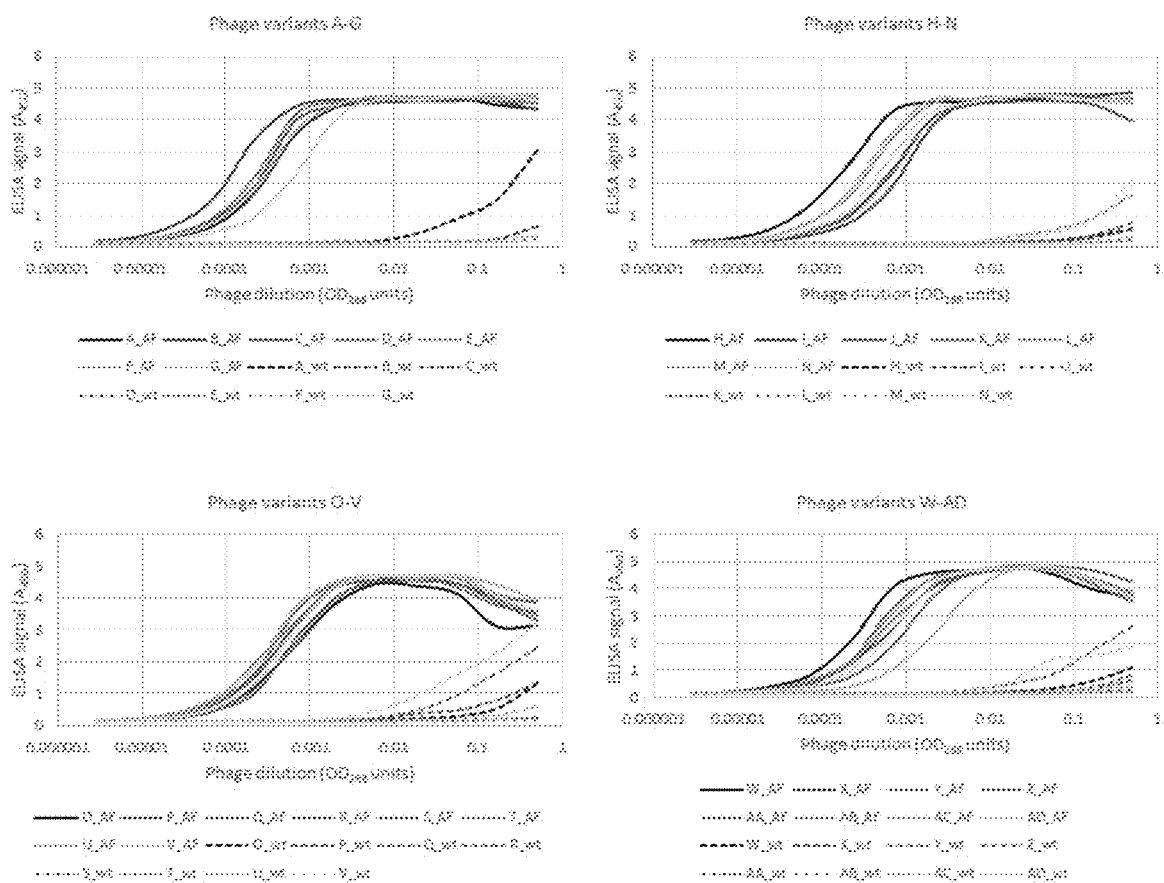
FIG. 10. Titration ELISA of individual phage variants to confirm selective binding to Fc-NKG2D.AF and reduced or eliminated binding to Fc-NKG2D.wt. Mutations are detailed in FIG. 11.

ELISA assays with Fc-eNKG2D fusions as capture agents were performed with ULBP2.wt, MICwed, MIC25 MicAbodies titrated starting at 300 nM (FIG. 6). $EC_{50}$ values were calculated when possible using GraphPad Prism (FIG. 7). Natural NKG2D bound to ULBP2, MICwed, and MIC25-based MicAbodies with affinities calculated as Kds values of 1.4, 0.007, and 0.005 nM, respectively. While affinity was diminished for ULBP2 and MICwed MicAbodies with all single mutant eNKG2D candidates, binding of MIC25 to eNKG2D candidates was retained. However, all double-mutant eNKG2D candidates had eliminated or significantly reduced binding to all three ligands-ULBP2, MICwed, and MIC25—in Micabody formats.

eNKG2D variants eNKG2D5 (Y152A/Y199F), eNKG2D7 (Y152S/Y199F), eNKG2D8 (Y152T/Y199F), and eNKG2D9 (Y152V/Y199F) had reduced or abolished binding to ULBP2, MICwed, and MIC25-based MicAbodies by both Octet® analysis and ELISA (FIGS. 5 and 7). Furthermore, eNKG2Ds 5, 7, and 8 had the least amount of aggregation, suggestive of more robust protein assembly upon 293T expression (FIG. 2). eNKG2D5 (SEQ ID NO: 48) was examined more closely for binding to wild-type ligands as MicAbodies captured on Octet® AHC tips. Single mutant Fc-NKG2D.Y152A (SEQ ID NO: 41) had reduced binding to all natural ligands relative to natural (SEQ ID NO: 40) NKG2D (FIG. 8). The response curve for binding of eNKG2D5 (Y152A/Y199F) was reduced even further relative to Y152A eNKG2D. eNKG2D5 (Y152A/Y199F, henceforth referred to as "AF" or "NKG2D.AF") was chosen as the lead NKG2D variant for which to engineer cognate selective, orthogonal, non-natural ligands.

Example 4: Constructing Orthogonal Non-Natural α1-α2 Domains with Selective Binding to Non-Natural NKG2D.AF Ectodomain We employed phage display to engineer orthogonal non-natural α1-α2 domains that exhibit selective binding to the Fc-NKG2D AF (SEQ ID NO: 48) receptor. As a starting point, the non-natural ULBP2.R80W α1-α2 domain (FIG. 1B; SEQ ID NO: 108) with high affinity for natural, wild-type NKG2D (NKG2D.wt) ectodomain was selected as the parent domain for further mutagenesis and screening by phage display. Synthetic DNA libraries were generated for the α1-α2 domain of ULBP2.R80W (SEQ ID NO: 108) which additionally has a C8S mutation to eliminate the potential for disulfide linkages. Codons of amino acid residues of the ligand that in the bound state are positioned in close proximity to the Y152 and Y199 positions on the natural NKG2D receptor were replaced with NNK codons; the libraries consisted of NNK codons at positions 154-159 (FIG. 1B; SEQ ID NO: 110). Libraries were cloned as fusions to the pill minor coat protein of M13 phage, and phage particles displaying the mutagenized α1-α2 domain variants were produced in SS320 *E. coli* cells according to standard methodologies (Andris-Widhopf, J., Steinberger, P., Fuller, R., Rader, C., and Barbas, C. F., 3rd. (2011). These α1-α2 phage display libraries were sorted for high binding affinity to the non-natural NKG2D.AF receptor by selectively capturing phage clones bound to biotinylated Fc-NKG2D.AF protein in the presence of non-biotinylated natural Fc-NKG2D.wt competitor protein. Selective clones were enriched by cycling through multiple rounds of competitive selection with increasing concentrations of the non-biotinylated natural Fc-NKG2D.

After four rounds of selection, phage clones were individually arrayed in 96-well format, spot ELISAs were performed to verify preferred differential binding to plate-bound non-natural NKG2D.AF versus NKG2D.wt. Bound phages were detected with biotinylated M13 phage coat protein monoclonal antibody E1 (ThermoFisher Scientific, Waltham, MA), streptavidin-HRP detection (R&D Systems, Minneapolis, MN), and 1-Step Ultra TMB ELISA development (ThermoFisher Scientific, Waltham, MA). The spot ELISA signal for each clone was expressed as a ratio of phage binding NKG2D.AF to phage binding NKG2D.wt. Those phages with a ratio greater than or equal to 14 were sequenced to identify the specific mutations within the NNK mutagenized regions. FIG. 9 shows the selected amino acid residues for each α1-α2 phage variant that selectively bound NKG2D.AF. In instances where multiple clones representing the same sequence were identified, the ratio of ELISA signals was plotted, and consistency of phage clones was verified by the clustering of data points (data not shown).

Thirty of the variants identified in ELISAs were expanded in individual monocultures to generate high titer micro-batches of phage. Purified phage concentrations were normalized to an $OD_{268}$=0.5 then subject to 1:3 dilution series against plate-bound Fc-NKG2D.AF or Fc-NKG2D.wt with phage detection and ELISA development performed as described above. All thirty variants assayed in this manner consistently demonstrated selective binding to NKG2D.AF with little to no binding to NKG2D.wt (FIG. 10) even at the highest concentrations of phage assayed. The selected phages also exhibited a shift of two or more logs of phage concentration to achieve half-maximal binding between NKG2D.AF and NKG2D.wt.

To confirm that the NKG2D.AF-selective α1-α2 domain variants retained specific binding properties in the context of antibody fusions, 21 variants (FIG. 11; e.g. SEQ ID NOs: 111-118) were cloned as C-terminal fusions with an APTSSSGGGGS linker (SEQ ID NO: 157) to the light chain of the rituximab antibody (SEQ ID NOs: 119-126). The resulting fusions were cloned into the mammalian expression vector pD2610-V12 (ATUM, Newark, CA) via Gibson cloning (New England Biolabs Inc., Ipswich, MA) and co-expressed with the heavy chain of the parent antibody (SEQ ID NO: 99) as paired full IgG antibodies. Transient expressions were carried out in Expi293™ cells (ThermoFisher Scientific, Waltham, MA) according to the manufacturer's protocol, and purified using standard protein-A affinity chromatography (cat. no. 20334, Pierce Biotechnology, Rockford, IL). ELISAs measuring the binding of each variant ULBP2 α1-α2 antibody fusions to non-natural Fc-NKG2D.AF and to natural Fc-NKG2D.wt demonstrated their significantly greater binding affinity toward NKG2D.AF relative to the natural NKG2D.wt (FIG. 11). Collectively, these data demonstrated the invention of non-natural, orthogonal α1-α2 domains that possessed high affinity binding to the non-natural NKG2D.AF receptor and significantly reduced binding affinity to the natural NKG2D receptor. Furthermore, fusions of these orthogonal α1-α2 domains to antibody polypeptides retained their selective binding properties and were used, for example, in the context of chimeric antigen receptor (CAR) T cells, to redirect non-natural NKG2D.AF receptors toward specific antigens.

Example 5: Identifying Non-Natural NKG2D Ligands that can Discriminate Between Non-Natural NKG2D Receptor Variants by Selectively Binding One or the Other Phage display to engineer orthogonal non-natural α1-α2 domains with selective binding to NKG2D.Y152A (henceforth referred to as NKG2D.YA, receptor was performed with non-natural ULBP2.R80W α1-α2 domain (SEQ ID NO: 108) as the starting point as described above. The α1-α2 phage display libraries were panned for high binding affinity to the non-natural Fc-NKG2D.YA receptor by selectively capturing phage clones bound to biotinylated Fc-NKG2D.YA (SEQ ID NO: 41) protein in the presence of non-biotinylated natural Fc-NKG2D.wt (SEQ ID NO: 40) competitor protein. Additional phage clone validation work resulted in the identification of variants with preferential binding to Fc-NKG2D.YA versus Fc-NKG2D.wt (FIG. 12). ULBP2.S3 (SEQ ID NO: 127), for example, consistently demonstrated selective binding by ELISA and Octet® analysis (both in monomeric His-tagged and bispecific antibody fused format) to non-natural NKG2D.YA relative to natural NKG2D.wt. This represented a distinct form of the invention of non-natural orthogonal α1-α2 domains possessing high affinity binding to non-natural NKG2D receptors (in this case NKG2D.YA as opposed to NKG2D.AF as in Example 4). Furthermore, fusions of orthogonal α1-α2 domains to antibody polypeptides retained their selective binding properties and were used to selectively redirect non-natural NKG2D receptors towards specific molecules determined by fused heterologous peptides such as antibodies.

Figure 13:
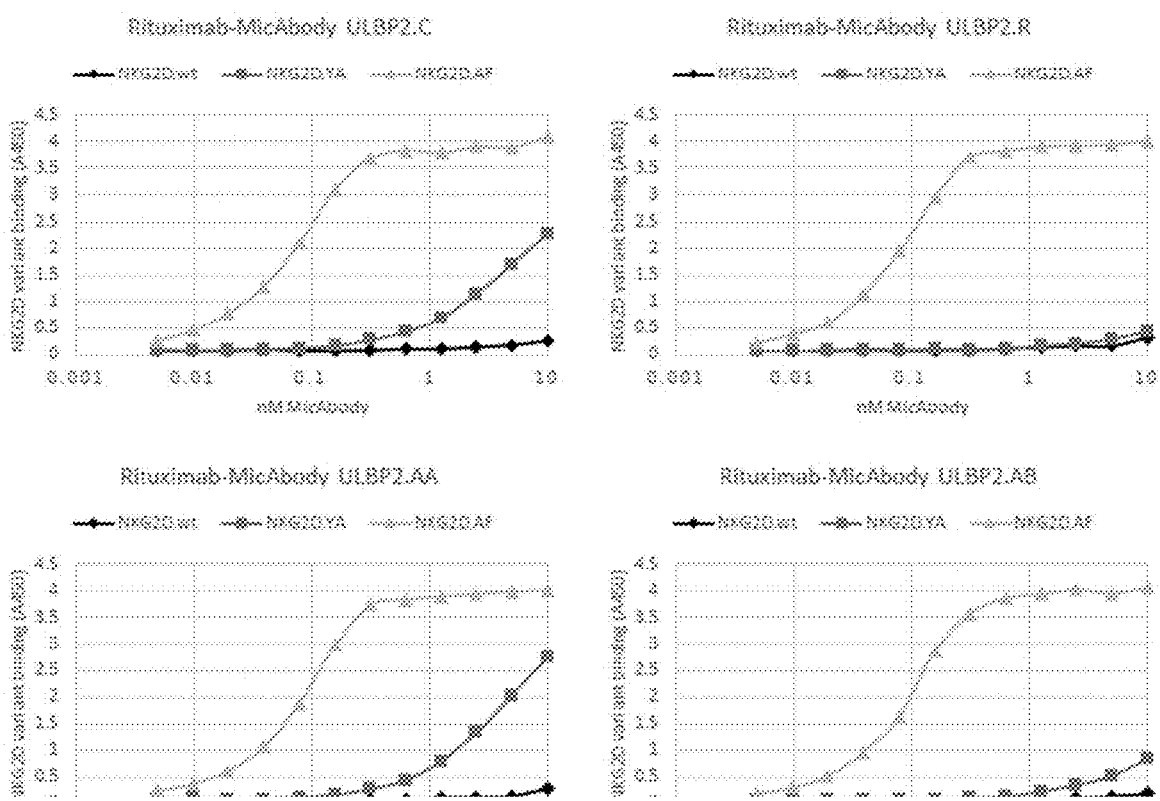
FIG. 13. ELISA data of four non-natural α1-α2 ULBP2 variant MicAbodies binding to NKG2D.wt, NKG2D.YA, and NKG2D.AF. The Fc-NKG2D variants were used as The differential regulation of NKG2D ligands, such as the polymorphic MICA and MICB, is important to provide the immunity system with a means to identify and respond to a broad range of emergency cues while still protecting healthy cells from unwanted attack (Stephens H A, (2001) MICA and MICB genes: can the enigma of their polymorphism be resolved? *Trends Immunol.* 22: 378-85; Spies, T. 2008. Regulation of NKG2D ligands: a purposeful but delicate affair. *Nature Immunol.* 9: 1013-1015).
Figure 14:
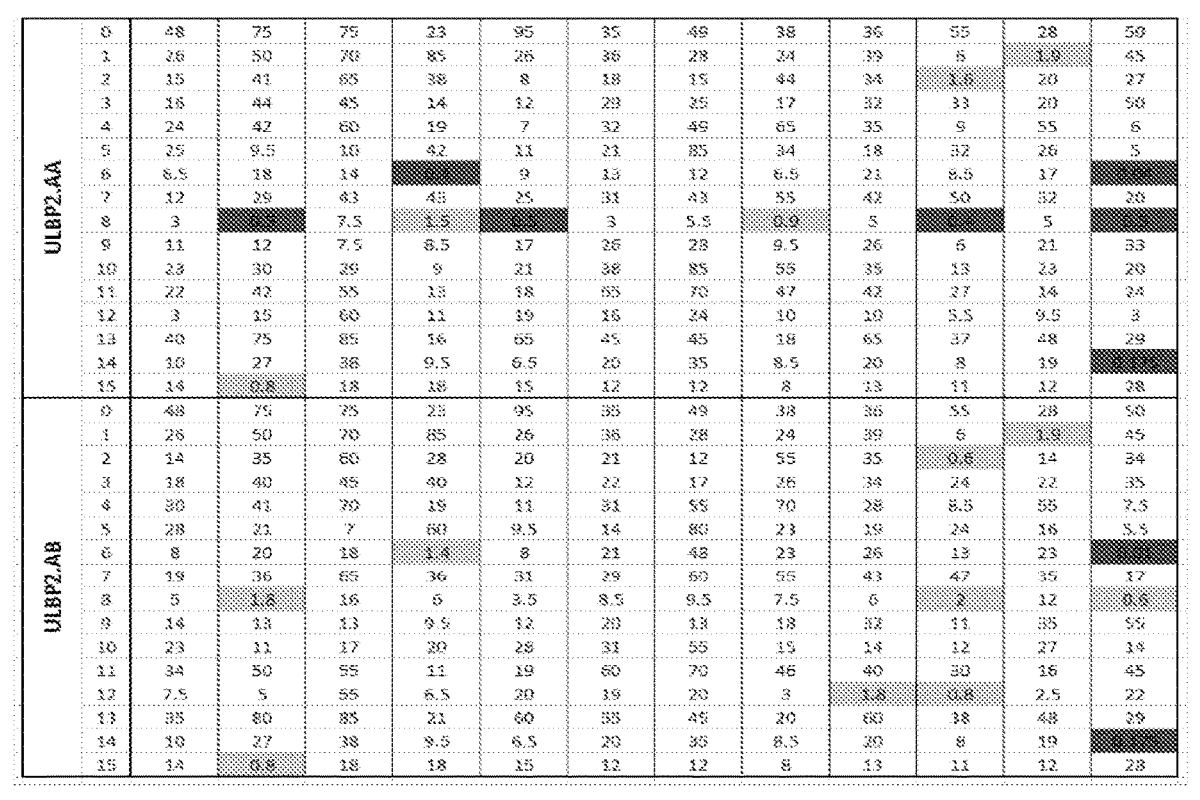
Figure 15:
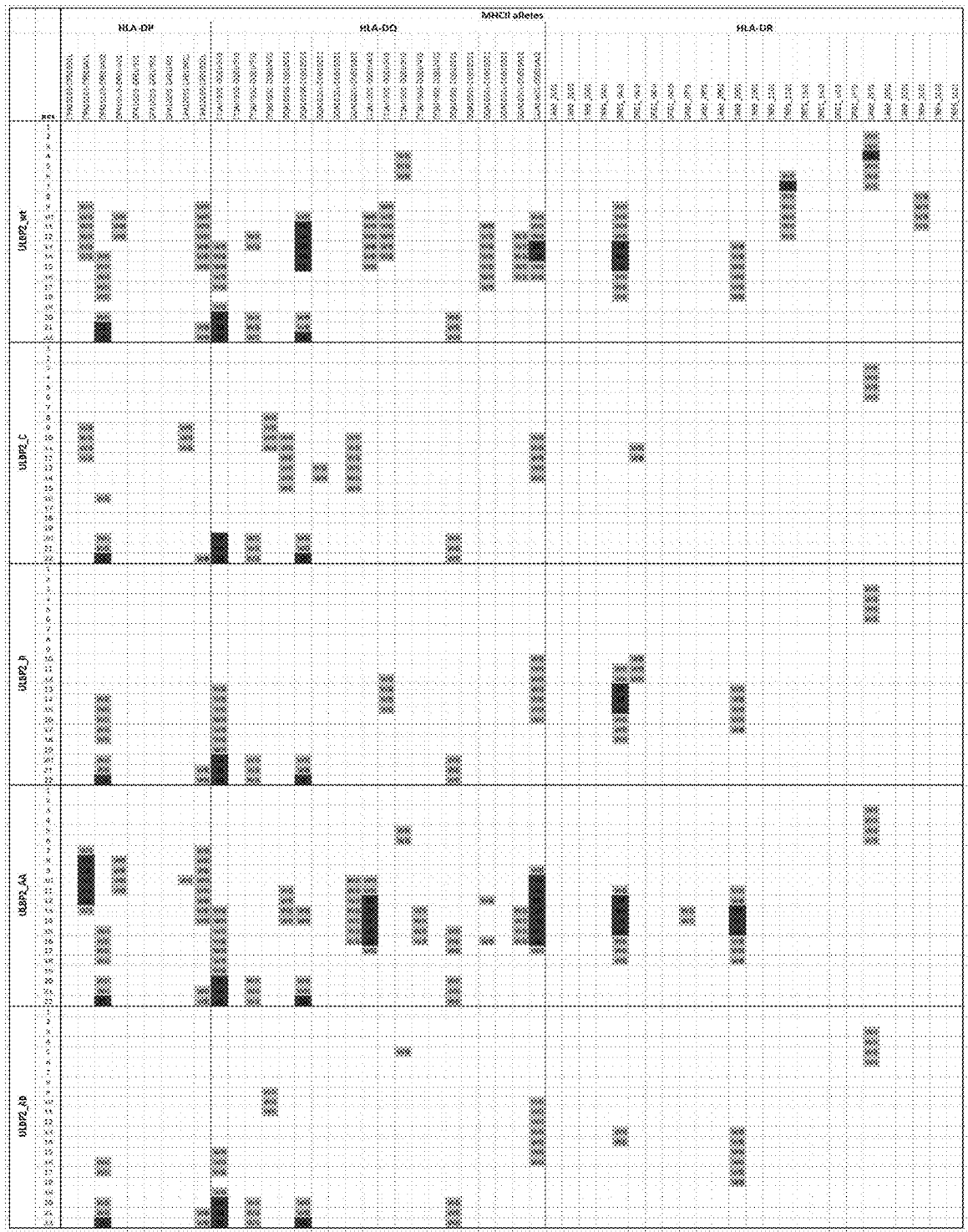
Figures 16A, 16B:
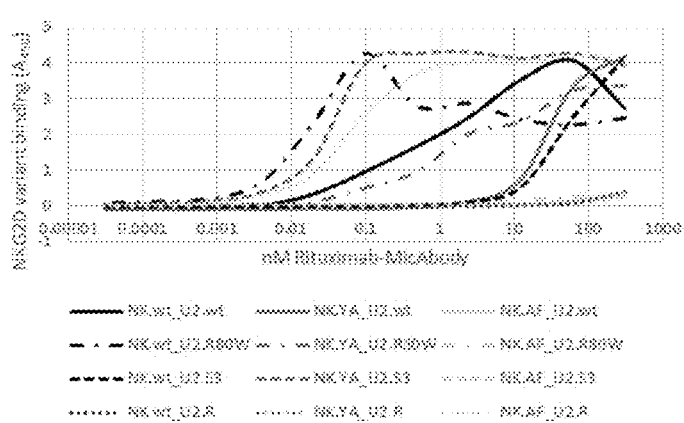

In order to determine whether a non-natural α1-α2 domain with selective binding to NKG2D.YA (ULBP2.S3, SEQ ID NO: 127) and the non-natural α1-α2 domains with selective binding to NKG2D.AF could discriminate between these two non-natural receptor variants, titration ELISAs were performed. All 21 of the selected α1-α2 variants that bound NKG2D.AF were directly compared for binding to NKG2D.AF versus NKG2D.YA. Of these, four demonstrated the properties of inability to bind NKG2D.wt, strong affinity for NKG2D.AF, and greatly reduced (15-20 fold) or eliminated binding to NKG2D.YA relative to NKG2D.AF (FIG. 13). These four non-natural ULBP2 α1-α2 variants— ULBP2.C, ULBP2.R, ULBP2.AA, and ULBP2.AB (SEQ ID NOs: 111, 113, 115, and 117)—were also examined for alterations in predicted immunogenicity profile relative to the wild-type ULBP2 peptide sequence (SEQ ID NO: 4) using the NetMHC4.0 Server (for peptide-MHC class I binding querying against all the HLA supertype representatives with 9-mer peptide analysis; cbs.dtu.dk/services/NetMHC/) and NetMHCII 2.3 Server (for peptide-MHC class II binding querying against HLA-DR, HLA-DQ, HLA-DP haplotypes with 15-mer peptide analysis; cbs.dtu.dk/services/NetMHCII/), both algorithms which were developed by the Technical University of Denmark (bioinformatics.dtu.dk/; Andreatta M and Nielsen M, Gapped sequence alignment using artificial neural networks: application to the MHC class I system, 2016 *Bioinformatics*, 32:511, PMID: 26515819; Jensen K K, Andreatta M, Marcatili P, Buus S, Greenbaum J A, Yan Z, Sette A, Peters B, and Nielsen M, Improved methods for predicting peptide binding affinity to MHC class I molecules, 2018 *Immunology*, PMID: 29315598). The mutations incorporated into ULBP2.C, ULBP2.R, and ULBP2.AB did not increase predicted immunogenicity while that of ULPB2.AA was increased slightly for a few haplotypes (FIGS. 14 and 15). As a consequence of the specificity of ULBP2.R for NKG2D.AF and its lack of predictable immunogenicity, ULBP2.R was selected for further ELISA analysis to directly compare its binding behavior with that of ULBP2.S3 (the NKG2D.YA-selected, non-natural, orthogonal ligand), ULBP2.R80W (non-natural ligand with enhanced affinity for wild-type NKG2D), and wild-type ULBP2 (ULBP2.wt). Binding of the four rituximab-MicAbody reagents (SEQ ID NOs: 98 and 121, 98 and 129, 131 and 100, and 98 and 106 as heavy chain and light chain for ULBP2.R, ULBP2.S3, ULBP2.R80W, and ULBP2.wt, respectively) was assayed against wild-type NKG2D (NKG2D.wt) and the two inert, non-natural variants NKG2D.YA and NKG2D.AF (FIGS. 16A and 16B). The data demonstrated that NKG2D.YA-selected variant ULBP2.S3 as a MicAbody bound with high affinity to NKG2D.YA but did not engage NKG2D.AF or natural NKG2D. Furthermore, the NKG2D.AF-selected variant ULBP2.R in MicAbody format bound with high affinity to NKG2D.AF but did not engage NKG2D.YA or natural NKG2D. These results demonstrated the tremendous potential of exploring the NKG2D-MIC ligand axis and for developing unique pairs of novel, selective non-natural NKG2D receptors and their respective, cognate non-natural MIC ligand binding partners.

Example 6: The Targeting and Killing Activity of CAR-T Cells Expressing the Non-Natural NKG2D.AF Ectodomain are Controlled by Orthogonal α1-α2 Domains Fused to Heterologous Targeting Polypeptides Means to selectively control CAR-T cell therapies are highly sought after to mitigate toxicity and improve efficacy against tumors (Gill and June, op cit). Previous attempts have been made to develop CARs using the ectodomain of CD16 which can then be engaged through the Fc domain of therapeutic monoclonal antibodies, allowing for antibody-based control of CAR-T targeting (Chang et al., op cit). However, CD16-based CAR-T cells can recognize nearly all endogenous antibody molecules in blood and tissues, and the therapeutic antibodies used to control these cells will encounter competition from endogenous CD16 receptors on NK cells, PMN's, monocytes and macrophages. Both of these features contribute problems of off-tumor toxicity and poor pharmacokinetics, respectively.

Natural NKG2D ligands are present on certain healthy tissues and many stressed tissues, creating an extreme risk for toxicity using current NKG2D CAR approaches (Van-Seggelen et al. 2015). The Y152A non-natural NKG2D receptor specifically bound to non-natural α1-α2 domain NKG2D ligands constituting an example of a means by which the activity of a non-natural NKG2D CAR could be selectively controlled using bispecific proteins comprised of the invented non-natural α1-α2 domain of NKG2D ligands.

We engineered CAR-T cells with a Receptor comprised of a modified Y152A/Y199F ("AF") ectodomain of NKG2D which lacks binding to all natural NKG2D ligands or previously described non-natural α1-α2 domains orthogonal and cognate to Y152A modified NKG2D (NKG2D.YA). The invented cognate non-natural α1-α2 domains bound with high affinity to the non-natural NKG2D.AF ectodomain and avoided binding to natural NKG2D ectodomains and to the NKG2D.YA ectodomain. Thus, engineered α1-α2 domains that exhibited strong selectivity for non-natural NKG2D.AF ectodomain over natural NKG2D and non-natural NKG2D.YA represent an ideal system for selective control of non-natural NKG2D CAR receptors, or any receptor or protein fused to non-natural NKG2D ectodomains that can be selectively engaged by the non-natural α1-α2 domains of the instant invention. The instant invention further enables single cells expressing two distinct CARs-one comprised of NKG2D.YA and the other of NKG2D.AF—each signaling with distinctly different intracellular domains. These distinct CARs would possess independent, dual controls of the cell's activities by extracellular exposure to the respective, cognate orthogonal MicAbody or another non-antibody fusion polypeptide.

Figure 17A:
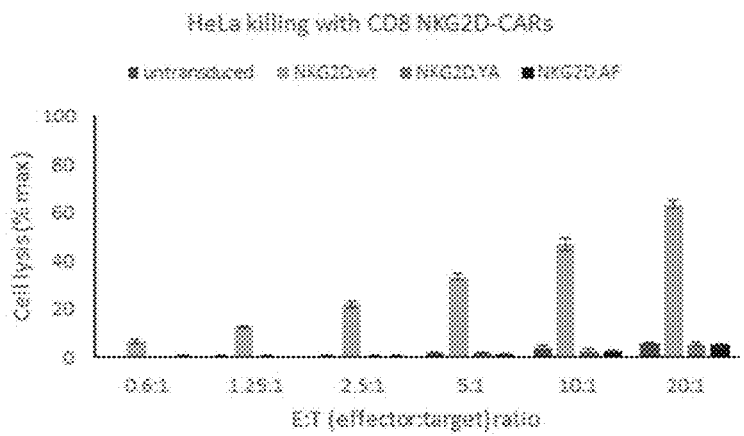
Figure 17B:
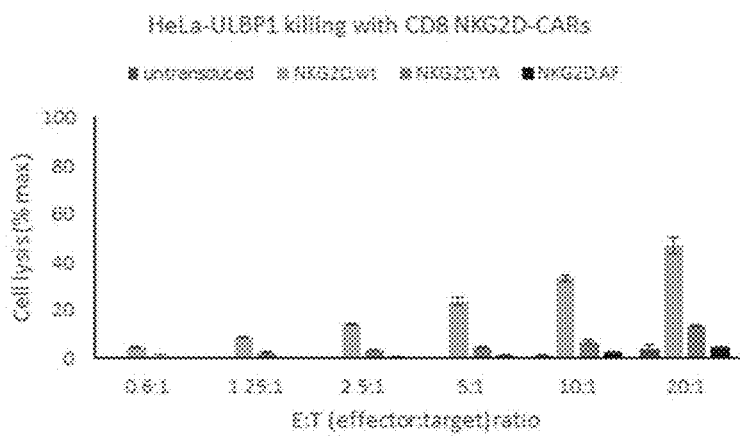
Figure 17C:
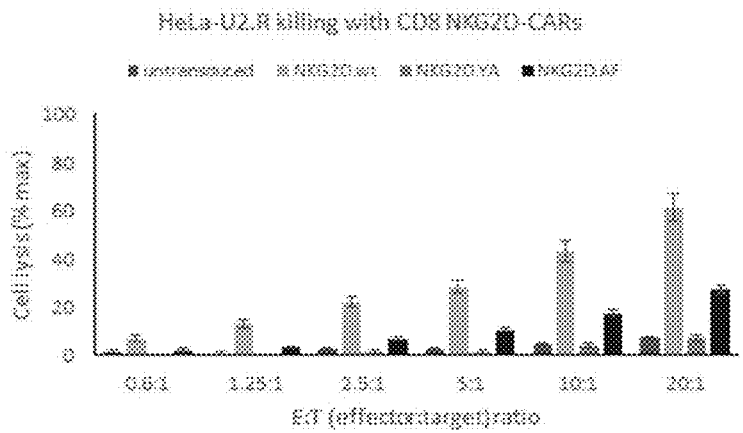

To demonstrate selective control of CAR-T cells constructed with a chimeric receptor deploying the non-natural NKG2D.AF ectodomain, we constructed CARs with either the natural NKG2D.wt (SEQ ID NO: 135), non-natural NKG2D.YA (SEQ ID NO: 137), or the non-natural NKG2D.AF (SEQ ID NO: 139) ectodomains based on previous work using 4-1BB/CD3zeta CAR constructs (Campana U.S. Pat. No. 8,399,645) fusing the respective NKG2D ectodomains to the CD8 hinge region of CARs (SEQ ID NOs: 151, 153, 155). These constructs (SEQ ID NOs: 152, 154, 156) were cloned into a lentiviral vector and expressed in primary human CD8-positive T cells using lentiviral transduction. Hela cells have constitutively upregulated levels of MIC ligands on their surface including MICA, MICB, ULBP3, and ULBP2/5/6 (the antibody used to ascertain this cannot distinguish between these three ULBPs; Human ULBP-2/5/6 Antibody, R&D Systems, Minneapolis, MN). Hela cells were transfected to also over-express either natural ULBP1 or the NKG2D.AF-selected variant ULBP2.R on their surface, and these cells were used as a target for in vitro killing assays. HeLa target cells were pre-loaded with calcein and exposed to NKG2D.wt-CAR, NKG2D.YA-CAR, or NKG2D.AF-CAR CD8 cells at increasing effector to target (E:T) ratios for five hours, after which the amount of calcein released into the supernatant was quantified and normalized to the total calcein released upon detergent treatment (FIGS. 17A-17C). Due to the elevated levels of MIC ligands naturally expressed on the surface of Hela cells, the CD8 cells expressing natural NKG2D (NKG2D.wt) as the CAR engaged the Hela cells via this over-expressed natural ligand and effected cytolysis. However, both the NKG2D.YA- and NKG2D.AF-CAR transduced CD8 cells demonstrated very little lysis of natural Hela cells even at high E:T ratios, a level of activity that is on par with untransduced CD8 T cells. When ULBP1 is overexpressed on the surface of Hela cells, only the NKG2D.wt-CAR CD8 T cells significantly lysed them. There is some additional killing at high E:T ratio with NKG2D.YA-CAR cells, but this is non-existent with NKG2D.AF-CAR cells showing that the double mutation Y152A/Y199F renders NKG2D even more inert than the single Y152A mutation. In Hela cells over-expressing the NKG2D.AF-selective non-natural ULBP2.R, NKG2D.wt-CAR cells direct lysis (due to recognition of endogenous MIC ligands) while NKG2D.AF-CAR cells directed significant levels of lysis consistent with engagement of the receptor and its selective ligand.

Figure 18A:
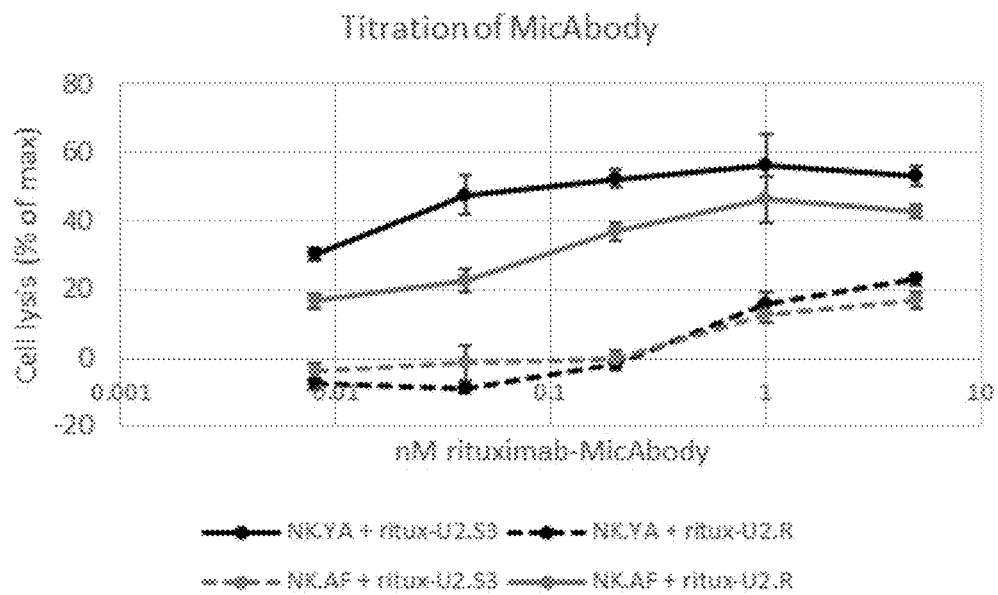
Figure 18B:
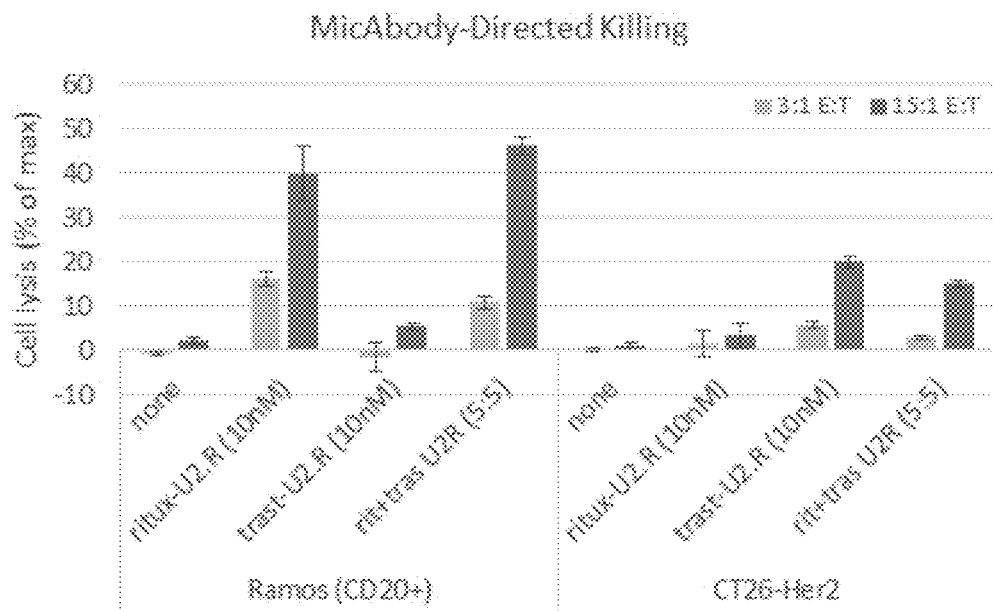

In order to demonstrate that lysis of either NKG2D.YA- or NKG2D.AF-CAR cells could only be directed by the appropriate, cognate targeting MicAbody, Ramos cells were used as a target for cytolysis in combination with rituximab-based MicAbodies linked to either non-natural ULBP2.S3 or ULBP2.R orthogonal ligands. As demonstrated in FIG. 18A, the rituximab-ULBP2.S3 MicAbody could direct the cell killing activity of NKG2D.YA-CAR CD8 cells but not NKG2D.AF-CAR cells, while the rituximab-ULBP2.R MicAbody could direct the activity of NKG2D.AF-CAR but not NKG2D.YA-CAR cells. This further demonstrates the selectivity of the two non-natural ULBP2 variants for their cognate non-natural NKG2D variants for which they were engineered as preferred partners. In order to demonstrate the specificity of the antibody portion of the MicAbody, in vitro killing assays were performed with NKG2D.AF-CAR CD8 cells that were pre-armed by incubation with either rituximab-ULBP2.R, trastuzumab-ULPB2.R (SEQ ID NOs: 95 and 133, heavy and light chain, respectively), or an equimolar combination of the two at a saturating total concentration of MicAbody. After unbound MicAbody was removed by washing, the CD8 cells were applied to either Ramos cells (expressing CD20, the target of rituximab) or to CT26-Her2 (a mouse cell line transfected to express human Her2) that had been pre-loaded with calcein. After a two hour incubation at two different E:T ratios, the amount of calcein released was quantified. As shown in FIG. 18B, when cells were pre-armed with rituximab-MicAbody, only Ramos cells were lysed while trastuzumab-MicAbody directed cytolytic activity only against CT26-Her2 cells. However, when NKG2D.AF-CAR CD8 cells were simultaneously pre-armed with both rituximab- and trastuzumab-ULBP2.R MicAbodies, both target cells lines were lysed demonstrating that these CAR cells—by virtue of the selective, privileged partnering that has been engineered between receptor and ligand—were readily multiplexed and thereby directed to engage different tumor targets simultaneously.

What is claimed is:

1. A non-natural, modified α1-α2 domain of a natural NKG2D ligand molecule, wherein said modified α1-α2 domain comprises an amino acid sequence having at least 90% identity to SEQ ID NO: 4, and wherein in said amino acid sequence having at least 90% identity to SEQ ID NO: 4, the positions corresponding to positions 80, 154, 155, 157, 158 and 159 of SEQ ID NO: 4 are substituted as compared to SEQ ID NO: 4, and
wherein said amino acid sequence having at least 90% identity to SEQ ID NO: 4 has at least one of the following features:
the amino acid at the position corresponding to position 157 of SEQ ID NO: 4 is W; or
the amino acid at the position corresponding to position 158 of SEQ ID NO: 4 is Q, G, or S.

2. The non-natural, modified α1-α2 domain of claim 1, wherein said amino acid sequence having at least 90% identity to SEQ ID NO: 4 has all of the following features:
the amino acid at the position corresponding to position 80 of SEQ ID NO: 4 is W;
the amino acid at the position corresponding to position 154 of SEQ ID NO: 4 is T;
the amino acid at the position corresponding to position 155 of SEQ ID NO: 4 is I, L, or M;
the amino acid at the position corresponding to position 157 of SEQ ID NO: 4 is W;
the amino acid at the position corresponding to position 158 of SEQ ID NO: 4 is Q, G, or S; and
the amino acid at the position corresponding to position 159 of SEQ ID NO: 4 is T or W.

3. The non-natural, modified α1-α2 domain of claim 1, wherein in said amino acid sequence having at least 90% identity to SEQ ID NO: 4, one or more of the positions corresponding to positions 8 and 156 of SEQ ID NO: 4 is substituted as compared to SEQ ID NO: 4.

4. The non-natural, modified α1-α2 domain of claim 1, which comprises an amino acid sequence selected from the group consisting of SEQ ID NOs: 111, 113, 115 and 117.

5. The non-natural, modified α1-α2 domain of claim 3, wherein in said amino acid sequence having at least 90% identity to SEQ ID NO: 4, the amino acid at the position corresponding to position 8 of SEQ ID NO: 4 is S.

6. The non-natural, modified α1-α2 domain of claim 3, wherein in said amino acid sequence having at least 90% identity to SEQ ID NO: 4, the amino acid at the position corresponding to position 156 of SEQ ID NO: 4 is L or M.

7. The non-natural, modified α1-α2 domain of claim 1, further comprising an attached heterologous molecule thereby creating a bispecific molecule.

8. The non-natural, modified α1-α2 domain of claim 7, wherein the heterologous molecule is a peptide or a polypeptide.

9. The non-natural, modified α1-α2 domain of claim 8, wherein the polypeptide is an antibody, antibody fragment, cytokine, lymphokine, or hormone.

10. The non-natural, modified α1-α2 domain of claim 7, wherein the heterologous molecule is an oligosaccharide, dendrimer, knottin, hormone, nucleic acid, or lipid.

* * * * *